(12) United States Patent
White

(10) Patent No.: US 10,352,846 B2
(45) Date of Patent: Jul. 16, 2019

(54) CALIBRATION DEVICE AND USES THEREOF

(71) Applicant: Applied Photophysics Ltd., Leatherhead (GB)

(72) Inventor: Nigel Thornton Hopley White, Dorking (GB)

(73) Assignee: APPLIED PHOTOPHYSICS LTD., Leatherhead (GB)

( * ) Notice: Subject to any disclaimer, the term of this patent is extended or adjusted under 35 U.S.C. 154(b) by 0 days.

(21) Appl. No.: 15/474,122

(22) Filed: Mar. 30, 2017

(65) Prior Publication Data
US 2018/0052098 A1   Feb. 22, 2018

Related U.S. Application Data

(63) Continuation of application No. PCT/US2015/054151, filed on Oct. 6, 2015.

(60) Provisional application No. 62/060,293, filed on Oct. 6, 2014.

(51) Int. Cl.
| | | |
|---|---|---|
| *G01N 21/19* | (2006.01) | |
| *G01N 21/27* | (2006.01) | |
| *G01N 21/17* | (2006.01) | |
| *G01N 21/21* | (2006.01) | |

(52) U.S. Cl.
CPC ........... *G01N 21/19* (2013.01); *G01N 21/274* (2013.01); *G01N 21/17* (2013.01); *G01N 21/21* (2013.01)

(58) Field of Classification Search
CPC ...... G01N 21/19; G01N 21/17; G01N 21/274; G01N 21/21

USPC ...................................................... 359/489.07
See application file for complete search history.

(56) References Cited

U.S. PATENT DOCUMENTS

| | | | |
|---|---|---|---|
| 3,637,311 A * | 1/1972 | Tipotsch | G01N 21/19 250/225 |
| 4,003,663 A † | 1/1977 | Steinberg | |
| 4,991,924 A * | 2/1991 | Shankar | G02B 5/3016 349/117 |
| 5,231,521 A * | 7/1993 | Johnson | G02F 1/13473 349/117 |

(Continued)

OTHER PUBLICATIONS

Lo et al., Measuring the Optical Rotation Angle and Circular Dichroism of Anisotropic Optical Media Using a Heterodyne Polarimeter. Journal of Lightwave Technology. Apr. 15, 2013;31(8):1255-1262.

(Continued)

*Primary Examiner* — William R Alexander
(74) *Attorney, Agent, or Firm* — McCarter & English, LLP; Jonathan M. Sparks

(57) ABSTRACT

This invention relates to a device for calibrating circular or linear dichroism spectrometers, or other photoelastic modulator (PEM) based devices or instruments. In preferred embodiments, the present invention features a device for calibrating circular dichroism or linear dichroism spectrometers comprising at least one waveplate (Q) providing ($n \pm \frac{1}{4}$) waves of retardation at a defined set of wavelengths, and at least one isotropic plate (P). The invention also features methods for using the device, for example, for calibrating circular dichroism spectrometers or linear dichroism spectrometers.

23 Claims, 63 Drawing Sheets

(56) References Cited

U.S. PATENT DOCUMENTS

| | | | | |
|---|---|---|---|---|
| 5,247,176 | A | * | 9/1993 | Goldstein ................ G01J 4/00 250/338.1 |
| 6,175,412 | B1 | | 1/2001 | Drevillon et al. |
| 6,396,575 | B1 | * | 5/2002 | Holland ............ G01M 11/3181 356/73.1 |
| 8,618,470 | B2 | * | 12/2013 | Dantus .................. G01N 21/21 250/252.1 |
| 9,297,744 | B2 | * | 3/2016 | Zeng ......................... G01J 9/00 |
| 9,995,850 | B2 | * | 6/2018 | Maleev ............... G02B 27/286 |
| 2005/0018117 | A1 | * | 1/2005 | Kewitsch ........... G02F 1/13363 349/119 |
| 2005/0213089 | A1 | * | 9/2005 | Margalith ................ G01J 3/10 356/300 |
| 2006/0023987 | A1 | * | 2/2006 | Yao .......................... G01J 4/00 385/11 |
| 2007/0019262 | A1 | * | 1/2007 | Lipson ...................... G01J 3/02 359/15 |
| 2007/0285601 | A1 | * | 12/2007 | Hendrix ............... G02B 5/3016 349/117 |
| 2008/0049584 | A1 | * | 2/2008 | Tan ........................ G02B 5/305 369/112.16 |
| 2008/0100842 | A1 | | 5/2008 | Johs et al. |
| 2009/0245304 | A1 | * | 10/2009 | Peng ..................... H01S 3/2333 372/29.02 |
| 2012/0092669 | A1 | | 4/2012 | Fiolka et al. |

OTHER PUBLICATIONS

Norden et al., Critical Aspects of Measurement of Circular and Linear Dichroism: A Device for Absolute Calibration. Applied Spectroscopy. Jun. 30, 1985;39(4):647-655.

International Search Report for Application No. PCT/US2015/054151, dated Jan. 29, 2016. 3 pages.

International Preliminary Report on Patentability for Application No. PCT/US2015/054151, dated Apr. 20, 2017. 6 pages.

Supplementary European Search Report for Application No. 15848546.6, dated May 11, 2018. 10 pages.

Yu-Lung Lo et al., Measuring the Optical Rotation Angle and Circular Dichroism of . . . , pp. 1255-1262, Pub. Apr. 15, 2013, Journal of Lightwave Technology, vol. 31, No. 8.†

Norden B., et al., Critical Aspects of Measurement of Circular and Linear Dichroism: . . . , pp. 647-655, Pub. Sep. 1, 1985, Journal of Society for Applied Spectroscopy, vol. 39, No. 5.†

\* cited by examiner
† cited by third party waveplate    tilted isoplate waveplate 1    isoplates    waveplate 2

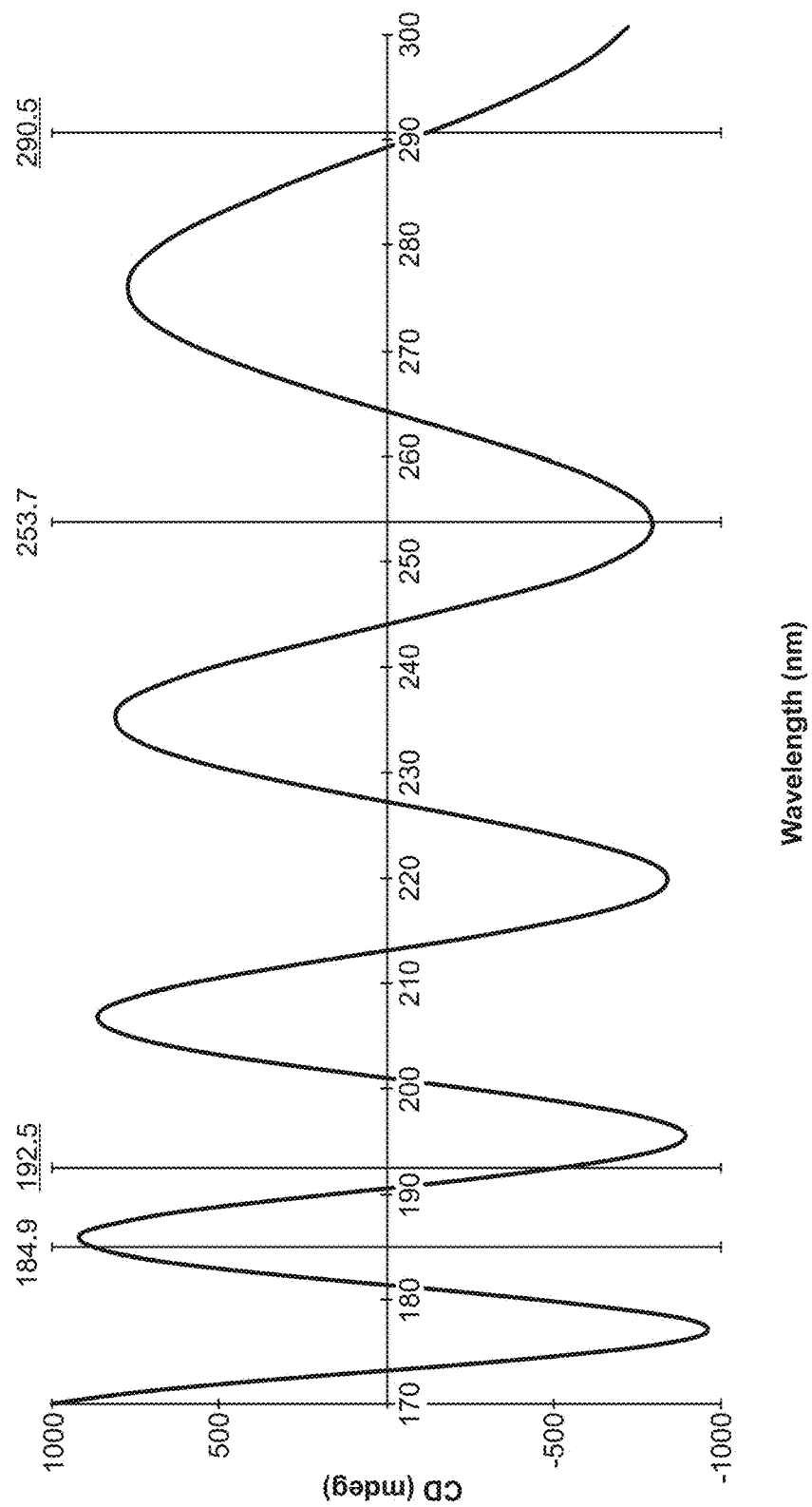

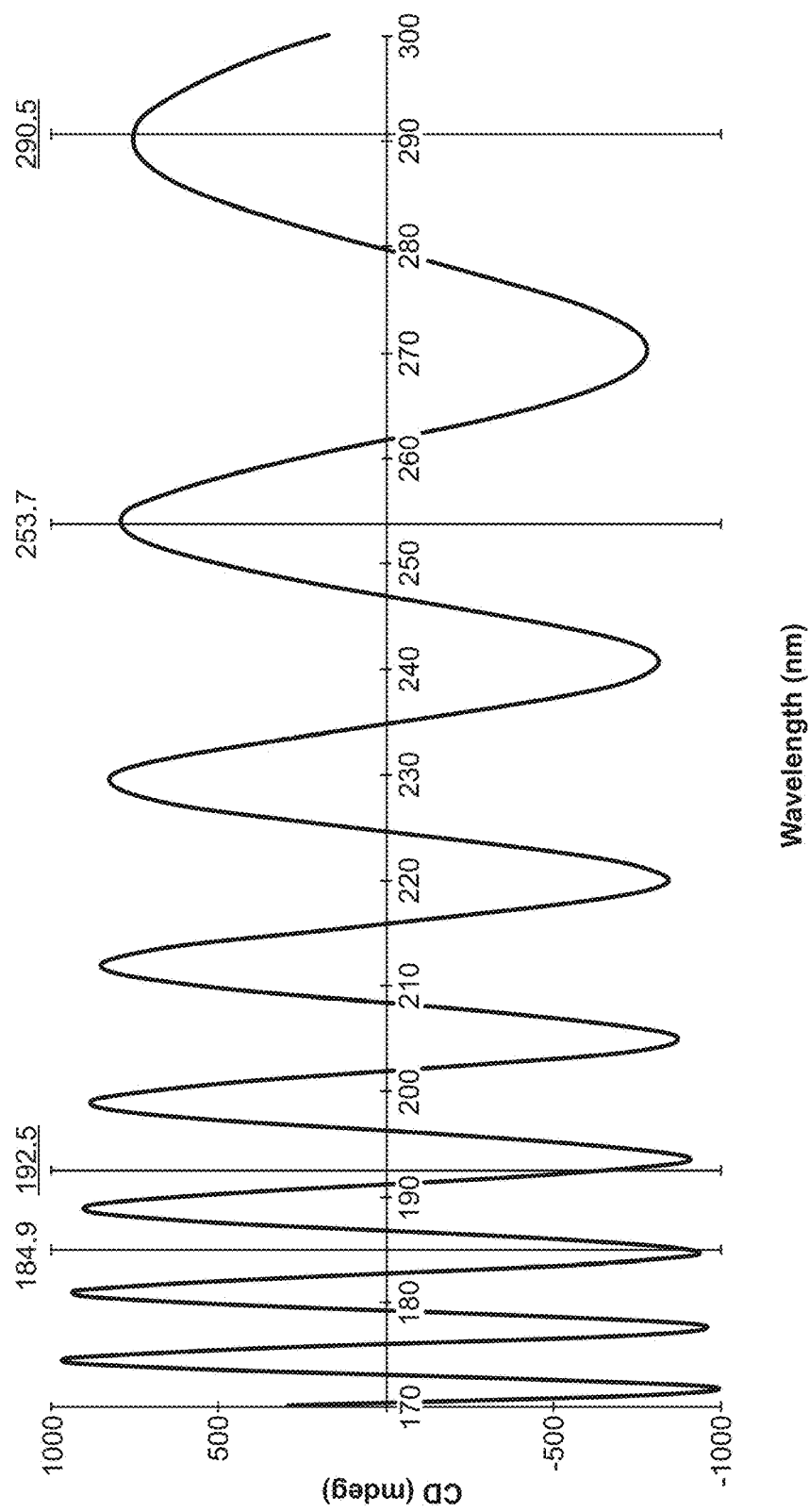

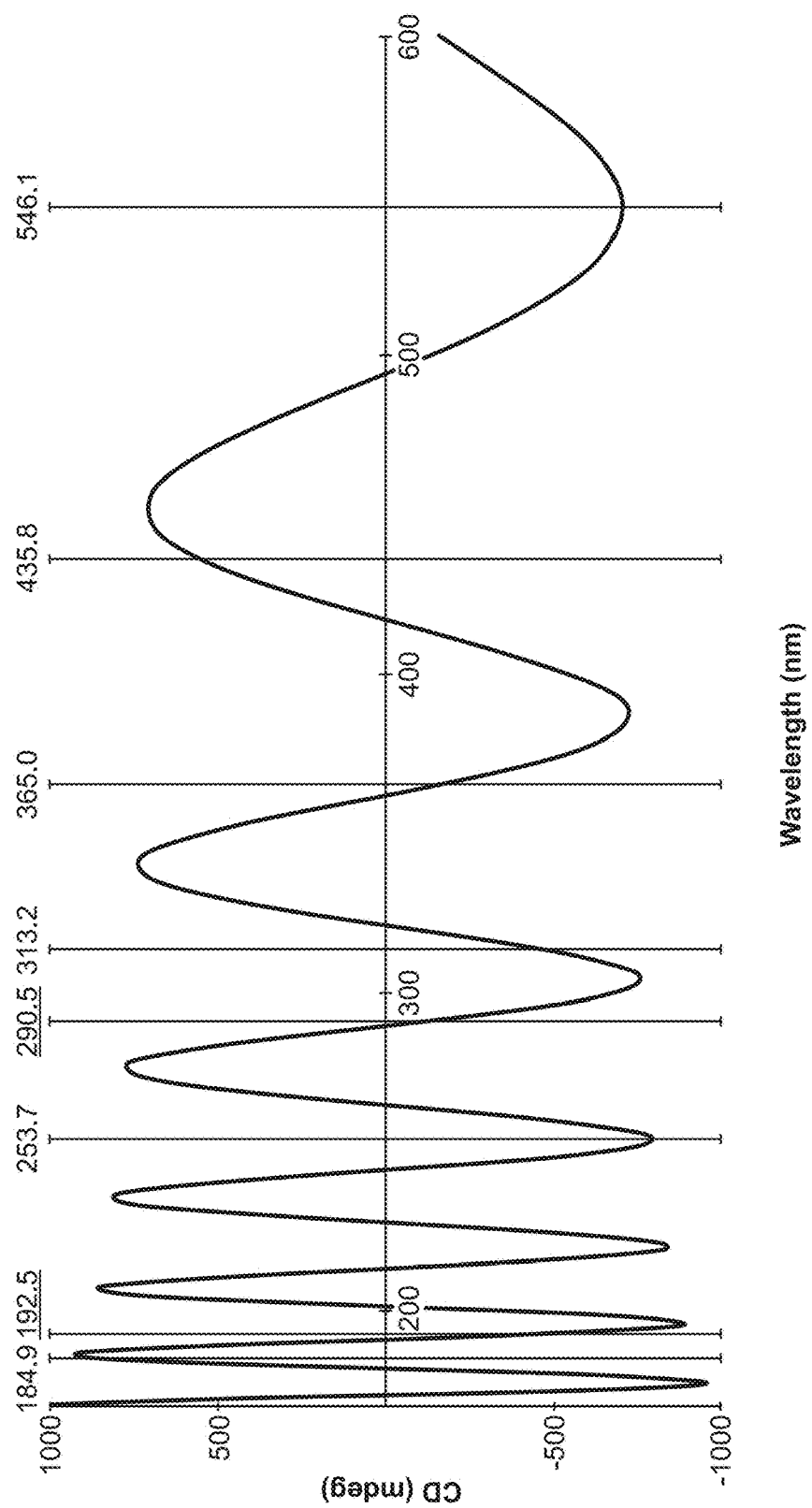

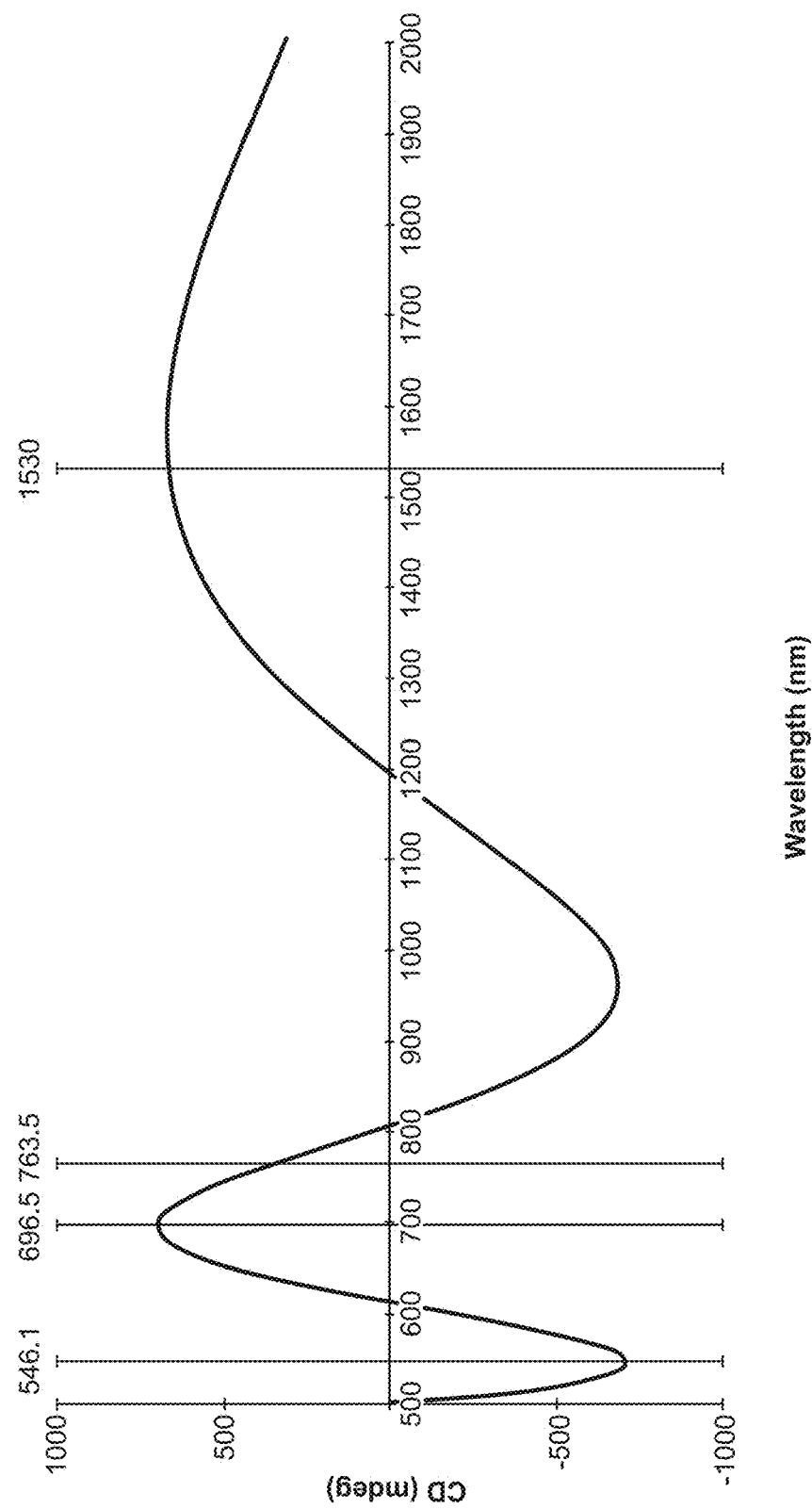

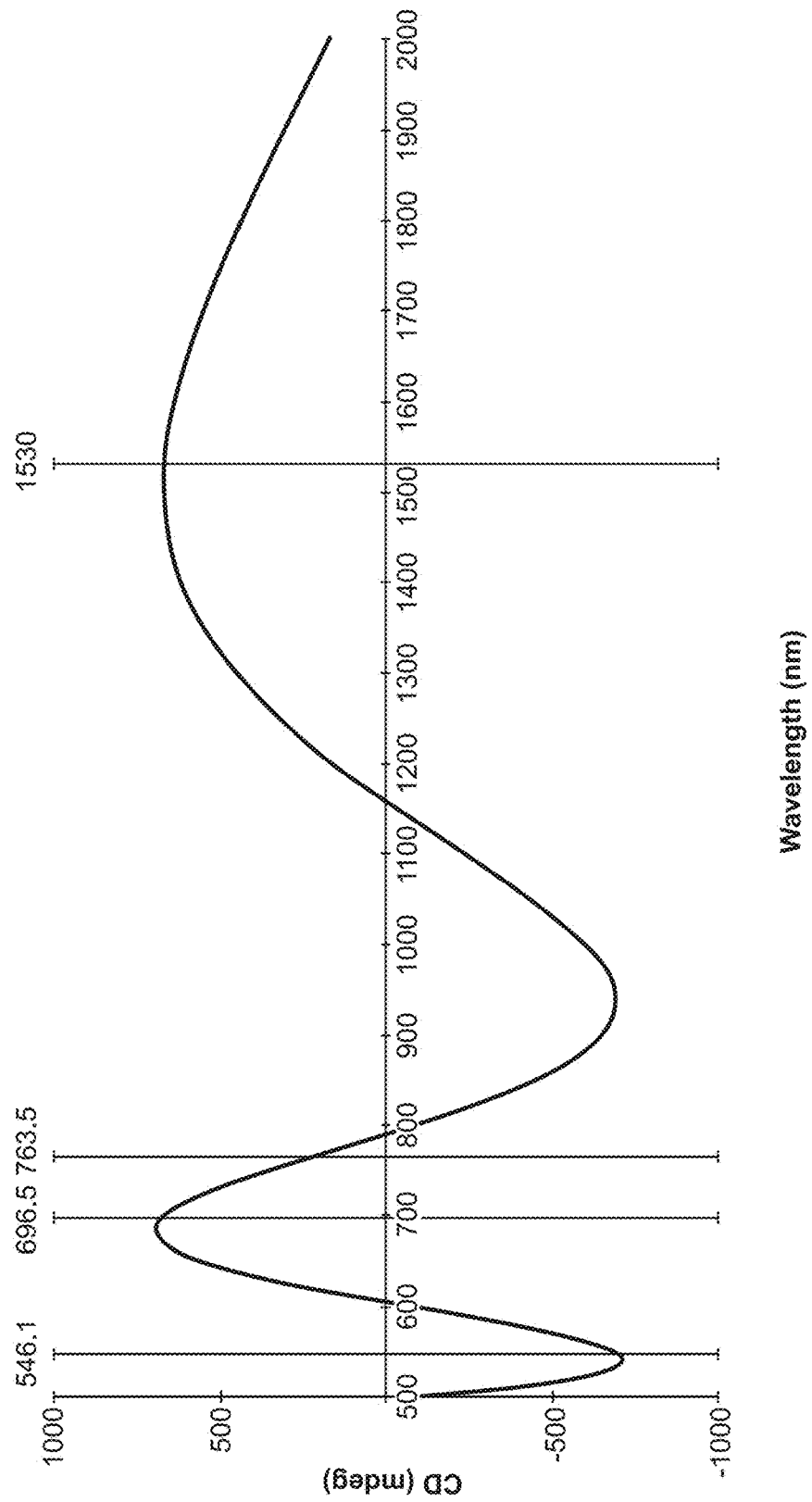

FIG. 13

| Variant Name | Schematic | Classification | Design Principle | Tilt Angle $\theta_{IP}$ | Rot&Av Angle | Pol State Restored |
|---|---|---|---|---|---|---|
| DichOS-1 | 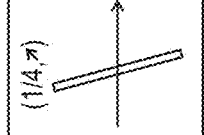 (1/4,π) | $Q_Y$ | Waveplate converts CPL to linear pol LD at second interface. Tilt of waveplate creates LD at second interface | 34.5° | 180° | No |
| DichOS-2 | 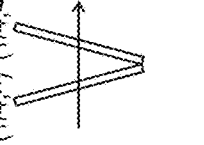 (1/4,π) (1/4,π) | $Q_{+Y}Q_{-Y}$ | Pol conversion in first waveplate LD at two inner WP interfaces Input pol state roughly restored by second waveplate at peak positions V arrangement reduces beam sensitivity | 24.5° | 90° | Poorly |
| DichOS-3 | 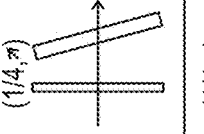 (1/4,π) | $Q_N P_Y$ | Pol conversion in first waveplate LD occurs at tilted iso-plate (both interfaces) | 28° | 180° | No |
| DichOS-4 | 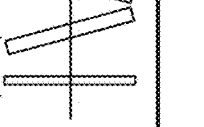 (1/4,π) | $Q_N P_{+Y} P_{-Y}$ | Based on Dichos-3 with V-plate arrangement of iso-plates to reduce beam sensitivity | 20° | 90° | No |

FIG. 13 (cont.)

| | | | | | |
|---|---|---|---|---|---|
| DichOS-5 | 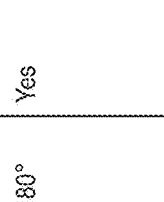 (1/4, π) (1/4, π) | $Q_N P_Y Q_N$ | Based on Dichos-3 with second waveplate added to restore input polarisation state at peak positions | 28° | 180° | Yes |
| DichOS-6 | 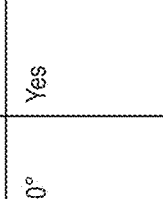 (1/4, π) (1/4, π) | $Q_N P_{+Y} P_{-Y} Q_N$ | Based on Dichos-3 with V-plate arrangement for reduced beam sensitivity and second waveplate to restore input polarisation state at peak positions | 20° | 90° | Yes |
| DichOS-7 | 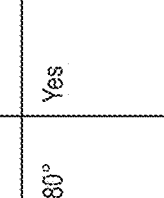 (1/4, π) (1/2, π) (1/4, π) | $Q_N P_Y H_N P_X Q_N$ | Based on Dichos-6 with second half rotated 90°. Middle 1/2 waveplate rotates polarisation state 90° at peaks. An attempt to balance and reduce beam errors | 20° | 180° | Yes |
| DichOS-8 | 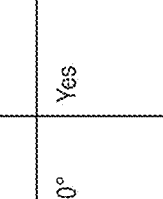 (1/4, π) (1/2, π) (1/4, π) | $Q_N P_{+Y} P_{-Y} H_N P_N P_N Q_N$ | Based on Dichos-6 with N-plate corrector integrated into device. Middle 1/2 waveplate ensures error signal is subtracted rather than added | 20° | 90° | Yes |
| DichOS-9 | 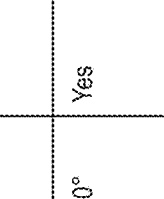 (1/4, π) (1/2, π) (1/4, π) | $Q_N P_{+Y} P_{-Y} H_N P_{+X} P_{-X} Q_N$ | Based on Dichos-6 with 'rotate and average' correction integrated. Middle 1/2 waveplate ensures signals from each half add rather than cancel | 14.5° | 90° | Yes |

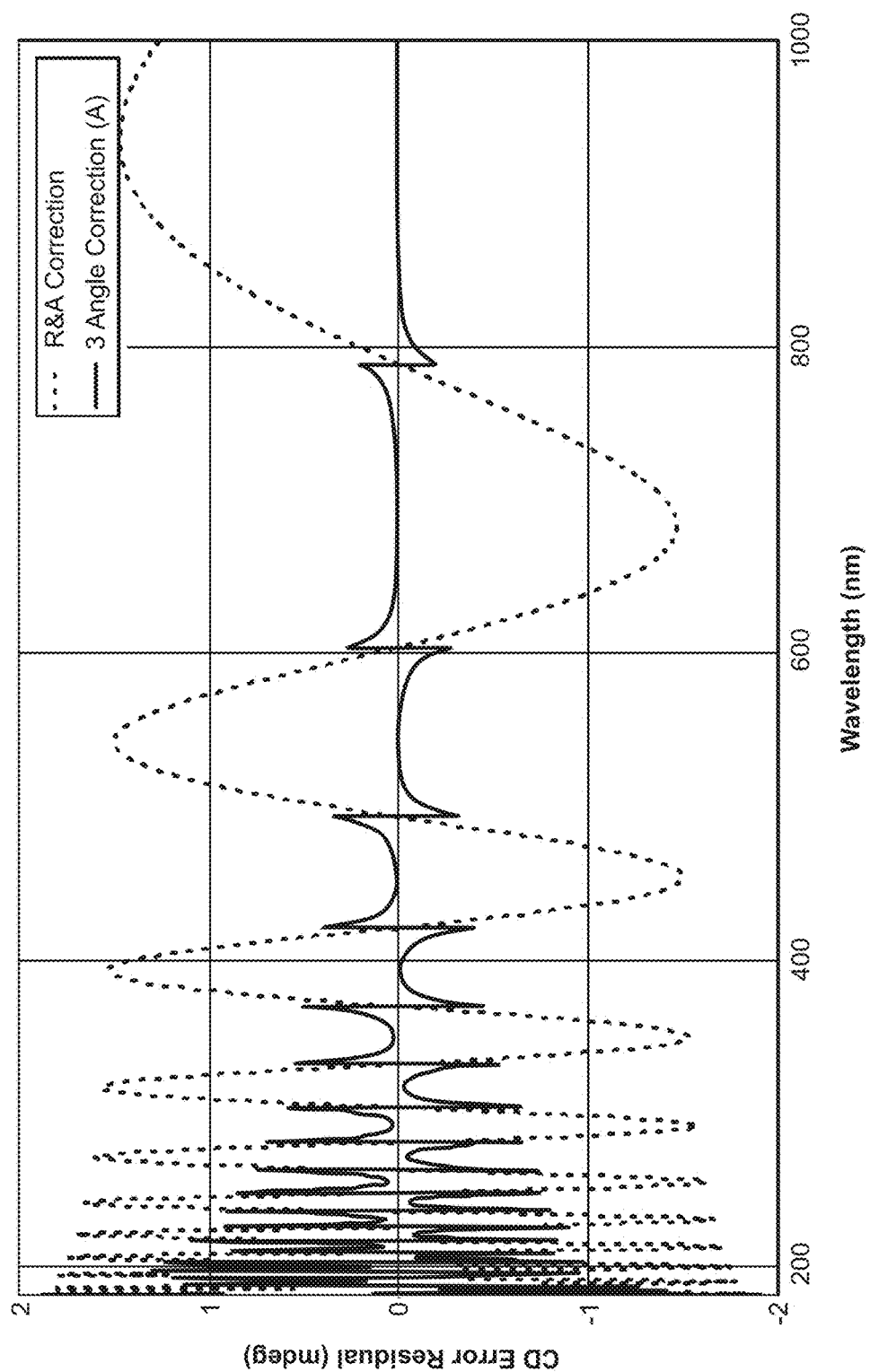

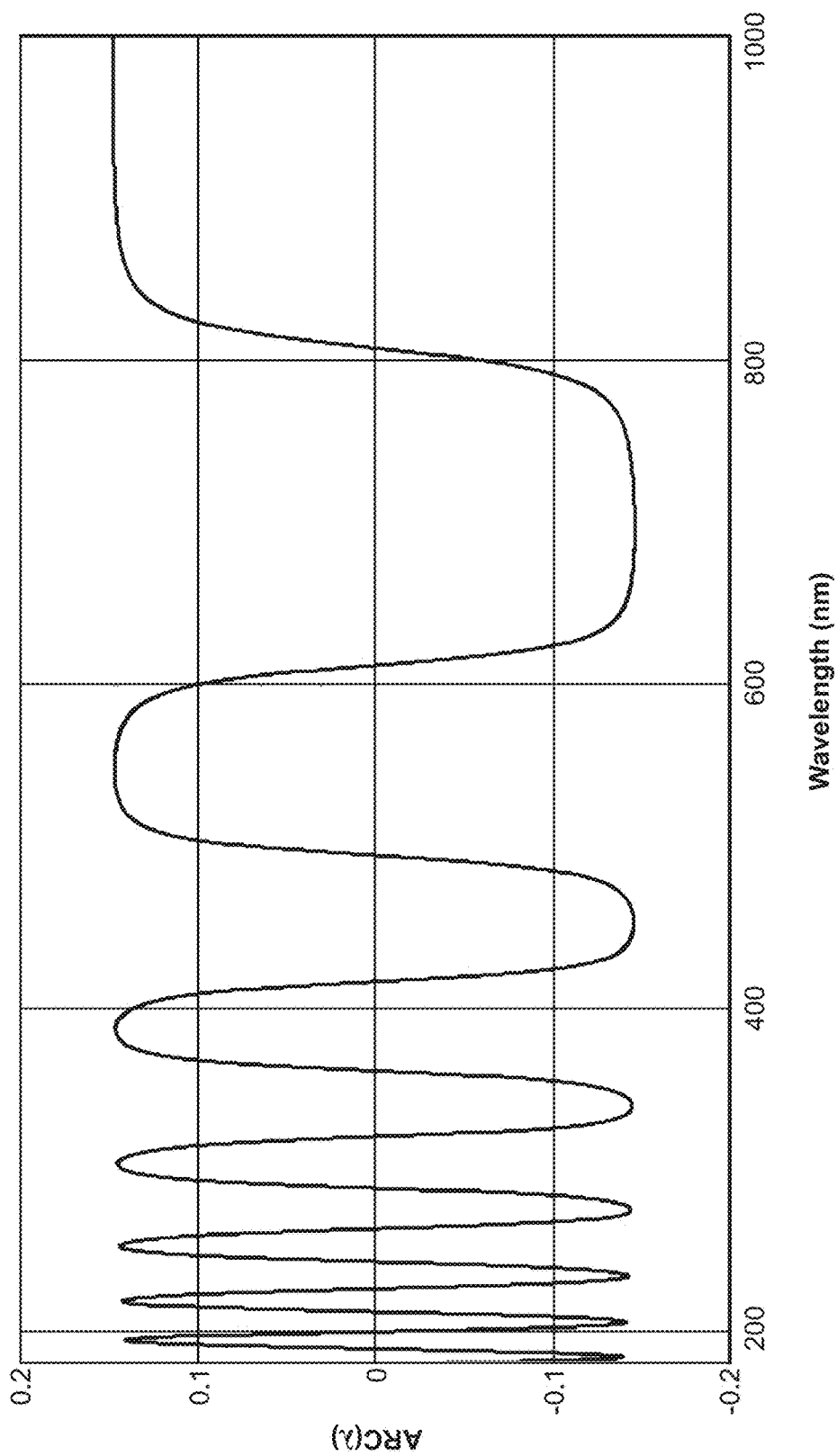

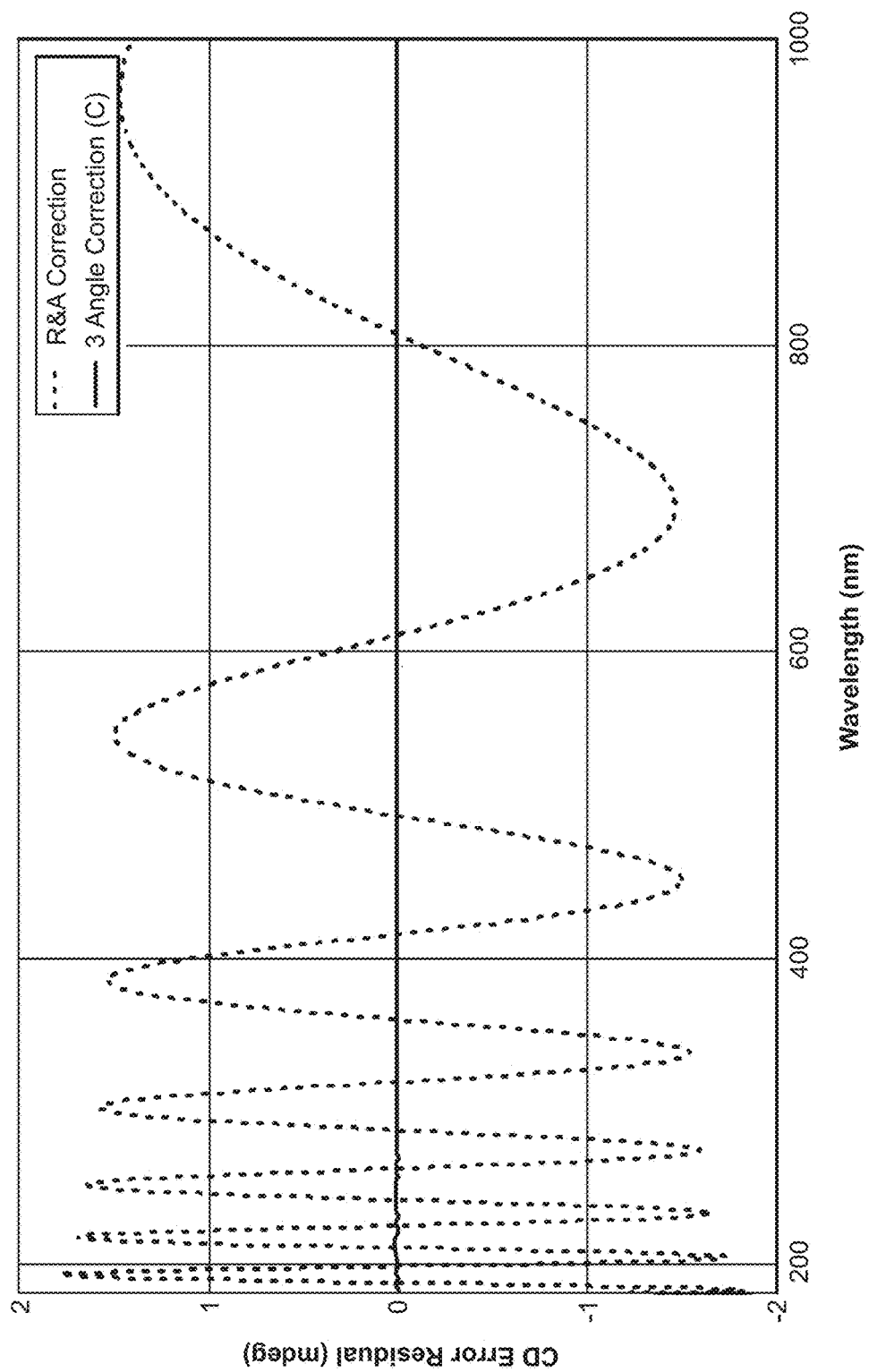

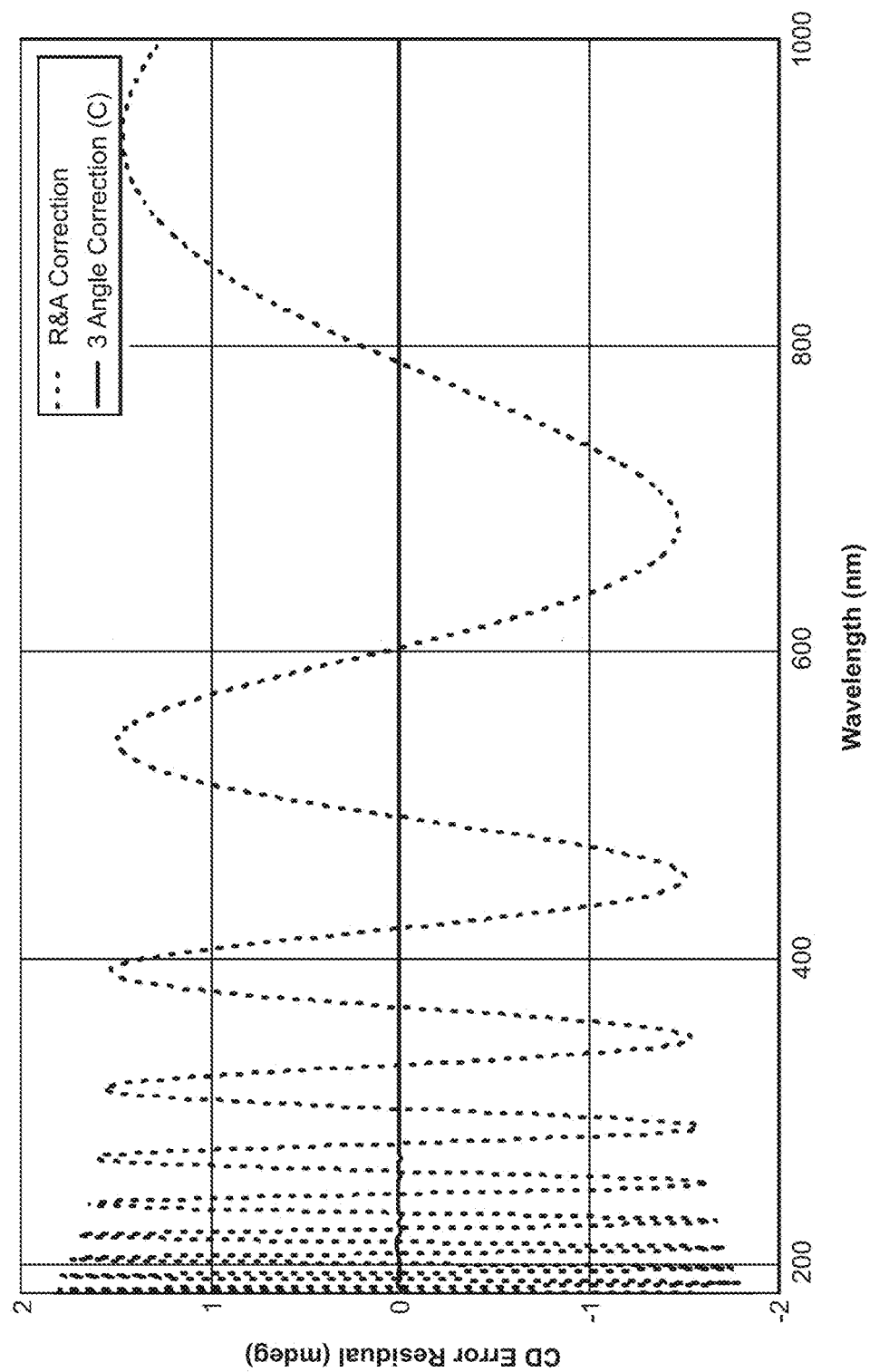

| Wavelength | Mean ΔCD% | 95% Confidence Interval | | Yield (±1%) |
|---|---|---|---|---|
| 185nm | -0.148% | -0.45% | +0.15% | 100% |
| 254nm | -0.123% | -0.45% | +0.15% | 100% |
| 542nm | -0.112% | -0.45% | +0.15% | 100% |
| 1500nm | -0.11% | -0.45% | +0.15% | 100% |

| Wavelength | Mean ΔCD% | 95% Confidence Interval | | Yield (±1%) |
| --- | --- | --- | --- | --- |
| 185nm | -0.221% | -1.95% | 1.75% | 71% |
| 254nm | -0.126% | -1.85% | 1.65% | 74% |
| 542nm | -0.068% | -1.65% | -1.65% | 77% |
| 1500nm | -0.079% | -1.75% | 1.55% | 77% |

| Wavelength | Mean ΔCD% | 95% Confidence Interval | | Yield (±1%) |
|---|---|---|---|---|
| 185nm | 0.244% | -0.45% | 0.95% | 97% |
| 254nm | 0.338% | -0.25% | 1.05% | 97% |
| 542nm | 0.381% | -0.15% | 0.95% | 98% |
| 1500nm | 0.397% | -0.15% | 0.95% | 98% |

| Wavelength | Mean ΔCD% | 95% Confidence Interval | | Yield (±1%) |
|---|---|---|---|---|
| 185nm | 0.077% | -0.65% | 0.75% | 99% |
| 254nm | 0.176% | -0.45% | 0.85% | 99% |
| 542nm | 0.22% | -0.35% | 0.75% | 100% |
| 1500nm | 0.235% | -0.35% | 0.75% | 100% |

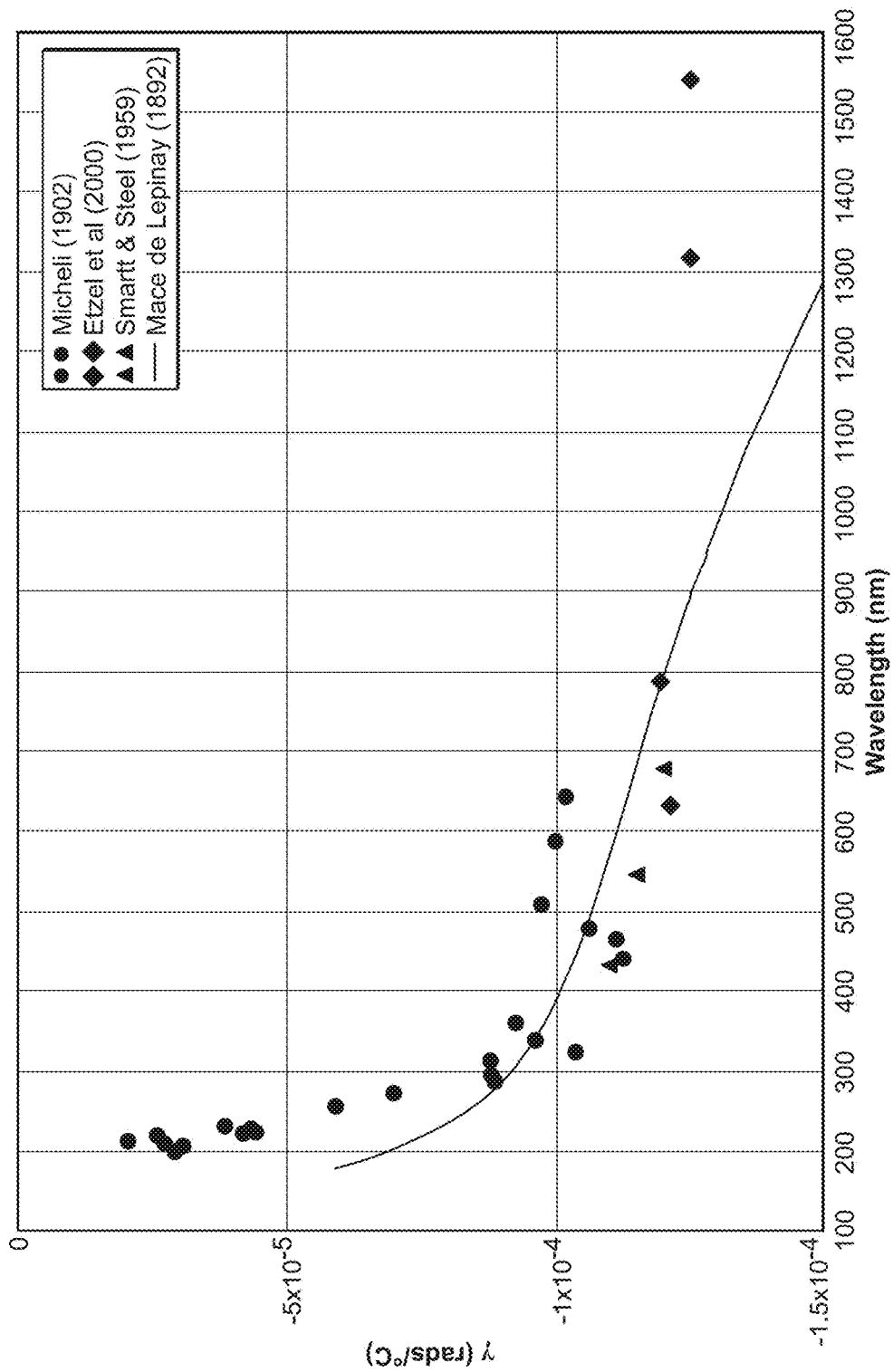

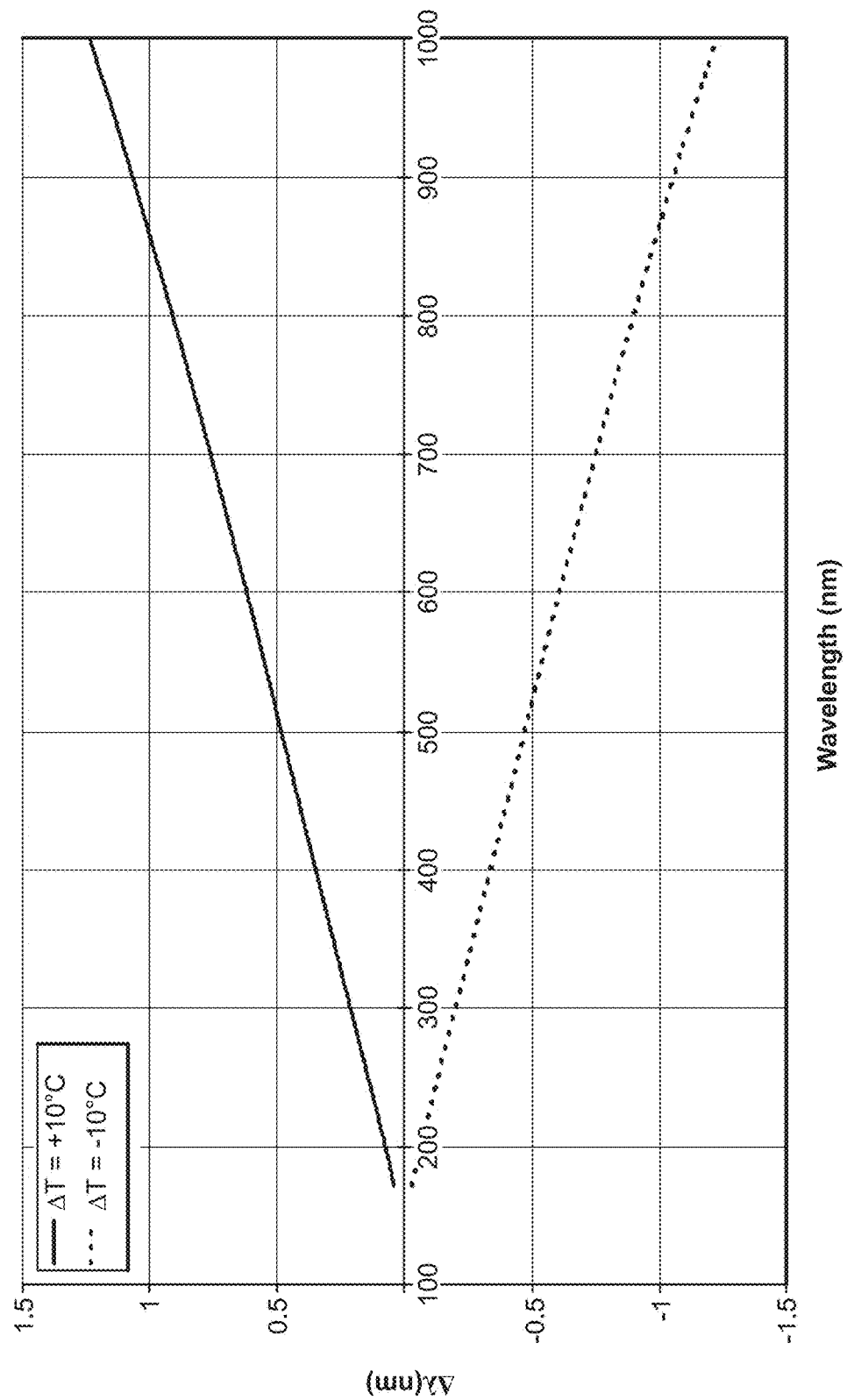

FIG. 44

| | No Correction ||| Rotate and Average Correction |||||| N-Plate Correction ||||
|---|---|---|---|---|---|---|---|---|---|---|---|---|---|
| | Beam Angle (H,V) || Beam Div (H,V) || Beam Angle (H,V) ||| Beam Div (H,V) || Beam Angle (H,V) ||| Beam Div (H,V) ||
| | (2°,0°) | (0°,2°) | (2°,2°) | (3°,3°) | (3°,5°) | (2°,0°) | (0°,2°) | (2°,2°) | (3°,3°) | (3°,5°) | (2°,0°) | (0°,2°) | (2°,2°) | (3°,3°) | (3°,5°) |
| DichOS-1 | 13% | 2% | 13% | -0.53% | -2.18% | 0.55% | 1.24% | 1% | -0.55% | -2.20% | | | | | |
| DichOS-2 | 1.5% | 1.3% | 1.5% | 0.11% | -0.85% | 0.1% | 0.7% | 1% | 0.14% | 0.26% | | | | | |
| DichOS-3 | 16% | 0.6% | 15.3% | 0.52% | -0.39% | 1.05% | -0.64% | 0.42% | 0.29% | -0.62% | | | | | |
| DichOS-4 | 1.54% | -1.13% | 0.42% | 0.31% | -1.20% | 0.21% | 0.21% | 0.21% | 0.31% | 0.59% | | | | | |
| DichOS-5 | 16% | 0.93% | 15% | 0.33% | -0.91% | 1.34% | -0.91% | 0.42% | 0.30% | -0.94% | | | | | |
| DichOS-6 | 1.85% | -1.43% | 0.42% | 0.31% | -1.62% | 0.21% | 0.21% | 0.42% | 0.31% | 0.59% | 0.51% | -0.10% | 0.42% | 0.31% | 0.18% |
| DichOS-7 | -10.2% | 10.6% | 0.40% | 0.48% | 0.78% | 0.21% | 0.21% | 0.42% | 0.32% | 0.61% | | | | | |
| DichOS-8 | 0.50% | -0.08% | 0.42% | 0.30% | -0.17% | 0.21% | 0.21% | 0.42% | 0.30% | 0.15% | | | | | |
| DichOS-9 | 0.21% | 0.21% | 0.41% | 0.30% | 0.57% | 0.21% | 0.21% | 0.42% | 0.30% | 0.54% | | | | | |

CALIBRATION DEVICE AND USES THEREOF

RELATED APPLICATIONS

This application is a continuation of International Patent Application No. PCT/US2015/054151, filed on Oct. 6, 2015, which claims priority to U.S. Provisional Application No. 62/060,293, filed on Oct. 6, 2014, the contents of which are incorporated by reference in their entireties herein.

FIELD OF THE INVENTION

This invention relates to a device for calibrating circular or linear dichroism spectrometers, or other photoelastic modulator (PEM) based devices or instruments. The invention also relates to methods of calibrating circular or linear dichroism spectrometers using said device.

BACKGROUND OF THE INVENTION

Circular dichroism (CD) spectroscopy is a spectroscopic technique where the CD of molecules is measured over a range of wavelengths. CD spectroscopy is used extensively to study chiral molecules of all types and sizes, and finds important applications in the study of large biological molecules. A primary use is in analyzing the higher order structure or conformation of macromolecules, particularly proteins. As higher order structure, for example secondary structure, is sensitive to its environment, temperature or pH, circular dichroism can be used to observe how the structure changes with environmental conditions or on interaction with other molecules. Structural, kinetic and thermodynamic information about macromolecules can be derived from circular dichroism spectroscopy.

CD calibration is required to ensure that measured CD spectra have the correct magnitude. Various factors affect measured CD magnitude, including optical imperfections in the instrument, detector non-linearity, detector polarization bias response, gains (AC and DC) in the electronic detection chain and photoelastic modulator (PEM) calibration. Ideally, CD calibration should correct for all of these error contributions across the entire wavelength range of the instrument. Calibration of CD instruments currently depends upon the use of chemical samples prepared to a prescribed concentration and measured in a cell of defined pathlength. There are several drawbacks to the use of standards such as these, including issues with accurate preparation, degradation over time, limited number or range of wavelengths over which the standard is applicable, and probably most importantly, the fact that, to qualify as a standard, the CD spectrum of the chemical sample itself has to initially be determined independently by some 'absolute' method. At present, no chemical CD standards exist which are traceable to a standards laboratory such as NIST or NPL.

It would be highly desirable if a solid optical CD calibration device could be developed whose theoretical CD spectrum could be computed accurately from the known configuration and optical constants of the materials comprising the device. The advantage of such an approach is that the refractive indices (including ordinary and extraordinary indices for birefringent materials) for a large number of optical materials have been determined to very high accuracy and can be modeled using well established dispersion formulae. Furthermore, materials exist, both birefringent and isotropic, which have transparency over the entire wavelength range of interest (170 nm to 1000 nm+), offering the potential for a truly wideband CD magnitude reference standard.

Several optical CD calibration devices have been described in the literature, however these suffer from certain drawbacks. For example, certain optical CD calibration devices described by the prior art are not applicable to the UV-VIS region. Moreover, a further drawback of the devices described in the prior art is that they fail to adequately take account of the effect of beam geometry (incident angle and especially divergence) on the CD signals produced. There remains a need in the art for a device that will provide more accurate calibration.

Accordingly, the present invention provides improved devices for dichroism measurements.

SUMMARY OF THE INVENTION

The present inventors have found that by combining one or more tilted isotropic plates (isoplates) with one or more waveplates of known retardance, it is possible to produce a device which presents an effective differential transmission to left and right circularly polarized states, rather than to linear polarized states.

Accordingly, in a first aspect the present invention features a device for calibrating circular dichroism or linear dichroism spectrometers, or other photoelastic modulator based devices or instruments, comprising at least one waveplate (Q) providing (n±¼) waves of retardation at a defined set of wavelengths; and at least one isotropic plate (P).

In a related embodiment, the device further comprises at least one waveplate (H) providing (N±½) waves of retardation at the same wavelengths where Q provides (n±¼) waves of retardation.

In another aspect, the present invention features a device for calibrating circular dichroism or linear dichroism spectrometers, or other photoelastic modulator based devices or instruments, comprising at least one waveplate (Q) providing (n±¼) wave of retardation; at least one waveplate (H) providing (N±½) wave of retardation; and at least one isotropic plate (P).

In one embodiment of any one of the above aspects, the waveplate (Q) has a thickness (t). In another embodiment of any one of the above aspects, the waveplate (H) has a thickness (2+4m)t. In another further embodiment of any one of the above aspects, the waveplate (H) has a thickness (2t).

In another embodiment of the above aspects t is between 0.01 mm to 5 mm, between 0.01 mm to 4.5 mm, between 0.01 mm to 4.0 mm, between 0.01 mm to 3.5 mm, between 0.01 mm to 3.0 mm, between 0.01 mm to 2.5 mm, between 0.01 mm to 2.0 mm, between 0.01 mm to 1.5 mm, between 0.01 mm to 1.0 mm, between 0.01 mm to 0.5 mm, between 0.01 mm to 0.4 mm, between 0.01 mm to 0.3 mm, between 0.01 mm to 0.2 mm or between 0.01 mm to 0.10 mm.

In another further embodiment, t is between 0.10 mm to 1.0 mm, for example 0.10 mm, 0.2 mm, 0.3 mm, 0.4 mm, 0.5 mm, 0.6 mm, 0.7 mm, 0.8 mm, 0.9 mm or 1.0 mm. In further embodiments, t is between 0.10 mm to 0.20 mm, for example 0.10 mm, 0.12 mm, 0.13 mm, 0.14 mm, 0.15 mm, 0.16 mm, 0.17 mm, 0.18 mm, 0.19 mm or 0.20 mm. In still further embodiments, t is between 0.100 mm to 0.150 mm, for example 0.100 mm, 0.101 mm, 0.102 mm, 0.103 mm, 0.104 mm, 0.105 mm, 0.106 mm, 0.107 mm, 0.108 mm, 0.109 mm, 0.110 mm, 0.111 mm, 0.112 mm, 0.113 mm, 0.114 mm, 0.115 mm, 0.116 mm, 0.117 mm, 0.118 mm, 0.119 mm, 0.120 mm, 0.121 mm, 0.122 mm, 0.123 mm, 0.124 mm, 0.125 mm, 0.126 mm, 0.127 mm, 0.128 mm, 0.129 mm, 0.130 mm, 0.131 mm, 0.132 mm, 0.133 mm, 0.134 mm, 0.135 mm, 0.136 mm, 0.137 mm, 0.138 mm, 0.139 mm, 0.140 mm, 0.141 mm, 0.142 mm, 0.143 mm, 0.144 mm, 0.145 mm, 0.146 mm, 0.147 mm, 0.148 mm, 0.149 mm or 0.150 mm.

In other further embodiments, t is between 0.1000 mm to 0.1050 mm, for example 0.1000 mm, 0.1001 mm, 0.1002 mm, 0.1003 mm, 0.1004 mm, 0.1005 mm, 0.1006 mm, 0.1007 mm, 0.0108 mm, 0.1009, 0.1010 mm, 0.1011 mm, 0.1012 mm, 0.1013 mm, 0.1014 mm, 0.1015 mm, 0.1016 mm, 0.0117 mm, 0.1018 mm, 0.1019 mm, 0.1020 mm, 0.1021 mm, 0.1022 mm, 0.1023 mm, 0.1024 mm, 0.1025 mm, 0.1026 mm, 0.0127 mm, 0.1028 mm, 0.1029 mm, 0.1030 mm, 0.1031 mm, 0.1032 mm, 0.1033 mm, 0.1034 mm, 0.1035 mm, 0.1036 mm, 0.0137 mm, 0.1038 mm, 0.1039 mm, 0.1040 mm, 0.1041 mm, 0.1042 mm, 0.1043 mm, 0.1044 mm, 0.1045 mm, 0.1046 mm, 0.0147 mm, 0.1048 mm, 0.1049 mm or 0.1050 mm.

In preferred exemplary embodiments, t is between 0.1027 to 0.1047, for example 0.0127 mm, 0.1028 mm, 0.1029 mm, 0.1030 mm, 0.1031 mm, 0.1032 mm, 0.1033 mm, 0.1034 mm, 0.1035 mm, 0.1036 mm, 0.0137 mm, 0.1038 mm, 0.1039 mm, 0.1040 mm, 0.1041 mm, 0.1042 mm, 0.1043 mm, 0.1044 mm, 0.1045 mm, 0.1046 mm or 0.0147 mm.

In other further embodiments, t is between 0.1300 mm to 0.1400 mm, for example 0.1300 mm, 0.1310 mm, 0.1320 mm, 0.1330 mm, 0.1340 mm, 0.1350 mm, 0.1360 mm, 0.1370 mm, 0.1380 mm, 0.1390 mm or 0.1340 mm. In further related embodiments, t is between 0.1310 mm to 0.1340 mm, for example 0.1310 mm, 0.1311 mm, 0.1312 mm, 0.1313 mm, 0.1314 mm, 0.1315 mm, 0.1316 mm, 0.1317 mm, 0.1318 mm, 0.1319 mm, 0.1320 mm, 0.1321 mm, 0.1322 mm, 0.1323 mm, 0.1324 mm, 0.1325 mm, 0.1326 mm, 0.1327 mm, 0.1328 mm, 0.1329 mm, 0.1330 mm, 0.1331 mm, 0.1332 mm, 0.1333 mm, 0.1334 mm, 0.1335 mm, 0.1336 mm, 0.1337 mm, 0.1338 mm, 0.1339 mm or 0.1340 mm.

In preferred exemplary embodiments, t is between 0.1318 mm to 0.1338 mm, for example 0.1318 mm, 0.1319 mm, 0.1320 mm, 0.1321 mm, 0.1322 mm, 0.1323 mm, 0.1324 mm, 0.1325 mm, 0.1326 mm, 0.1327 mm, 0.1328 mm, 0.1329 mm, 0.1330 mm, 0.1331 mm, 0.1332 mm, 0.1333 mm, 0.1334 mm, 0.1335 mm, 0.1336 mm, 0.1337 mm or 0.1338 mm.

According to the present invention, the thickness (t) can vary by ±0.001 mm. A deviation of ±0.001 mm does not impact the usefulness of the aspects or embodiments of the invention described herein.

For example, in one preferred embodiment of the present invention, t is 0.1037±0.001 mm. In another preferred embodiment of the present invention, t is 0.1328±0.001 mm.

In one embodiment of the above aspects, the waveplate (Q) or the waveplate (H) is oriented with its surface normal to a direction of light propagation (Z axis).

In a further embodiment of the above aspects, the waveplate (Q) or the waveplate (H) is oriented with its crystal axis at an angle about a Z axis, measured from the positive X axis direction. In a preferred embodiment, the angle is 45° about the Z axis. In another embodiment of any one of the above aspects, the waveplate (Q) or the waveplate (H) is subsequently rotated about a Y axis. In a related embodiment, the angle is between 1° and 90° about the Y axis. In a further embodiment of one of the above aspects, the waveplate (Q) or the waveplate (H) is subsequently rotated about an X axis. In a related embodiment, the angle is between 1° and 90° about the X axis.

In another embodiment of any one of the above aspects, the isotropic plate (P) is oriented at an angle about a Y axis. In one embodiment, the angle is between 1° and 90° about the Y axis. In a preferred embodiment, the angle is 20°.

In another embodiment of any one of the above aspects, the isotropic plate (P) is oriented at an angle about an X axis. In a further embodiment, the angle is between 1° and 90° about the X axis. In a preferred embodiment, the angle is 20°.

In one embodiment of any one of the above aspects, the angles are measured clockwise or anticlockwise.

In another embodiment of any one of the above aspects two isotropic plates (P) are oriented at equal and opposite angles about the X or Y axis.

In another further embodiment of any one of the above aspects, the isotropic plate (P) is oriented normal to a direction of light propagation (Z axis).

In yet another embodiment of the above aspects, the waveplate (H) or the isotropic plate (P) is coated or uncoated. In a related embodiment, the coating is a dielectric or a metallic coating. In another related embodiment, the coating is a single layer or multi-layered.

In another embodiment of any one of the above aspects, the waveplate (Q) or the waveplate (H) comprises a birefringent material.

In one embodiment of any one of the above aspects, the isotropic plate (P) comprises an isotropic material having transparency over the wavelength range of interest for the instrument being calibrated.

In yet another embodiment of any one of the above aspects, at least one isotropic plate (P) is replaced by at least two prisms.

In still another embodiment of any one of the above aspects, the one or more waveplates are replaced with one or more non-birefringent retarders. In one embodiment, the non-birefringent retarders are selected from the group consisting of a Fresnel rhomb, a Mooney rhomb and an Oxley prism. In another embodiment of any one of the above aspects, one or more waveplates are replaced by a single wavelength compound zero order retarder or an achromatic retarder.

In another embodiment of any one of the above aspects, the device further comprises a neutral density filter. In a further embodiment, the neutral density filter is disposed in series either before the first waveplate or after the last waveplate.

An another embodiment of any one of the above aspects, the device further comprises a mechanical light attenuator in the form of a grid, comb, aperture or similar device which causes one portion of the beam to be interrupted while another portion of the beam is allowed to propagate. In a further embodiment, the mechanical attenuator is disposed at any position with respect to the other optical components comprising the device.

In another embodiment of any one of the above aspects, the device further comprises a motor to rotate or spin the device.

In still another embodiment of any one of the above aspects, the device further comprises a manifold or a system for nitrogen purging.

In still another embodiment of any one of the above aspects, the device further comprises a means of sealing a nitrogen atmosphere within an enclosure housing the optical elements of the device.

In another embodiment of any one of the above aspects, the device further comprises a polarizer.

In another embodiment of any one of the above aspects, the device further comprises a linearly dichroic sample.

In another embodiment of any one of the above aspects, the device further comprises a detector.

In another embodiment of any one of the above aspects, the device further comprises a processor.

In one embodiment of any one of the above aspects, the device of the invention is used for calibrating circular dichroism spectrometers. In another embodiment of any one of the above aspects, the device of the invention is used for calibrating linear dichroism spectrometers. In a further embodiment, where a first spectrum is measured, the device is replaced with the device of any one of the aspects described infra, and a second spectrum is measured. In another further embodiment, use of the device further comprises the step of subtracting the second spectrum from the first spectrum. In another related embodiment, a first spectrum is measured, the device is rotated axially through a fixed angle and a second spectrum is measured. In another further embodiment, the fixed angle is 90° or 180°. In another related embodiment, the angles are measured clockwise or anti-clockwise.

In another embodiment of the above aspects, use of the device further comprises the step of taking the average of the two measured spectra.

In a further embodiment, when a first spectrum is measured, the device is rotated axially through a fixed angle and a second spectrum is measured, the device is rotated axially through a further fixed angle and a third spectrum is measured. In a related embodiment, the fixed angles are 45° and 45° or 90° and 90°. In a further related embodiment, the angles are measured clockwise or anticlockwise.

In another embodiment of any one of the above aspects, the measured spectra are processed through an algorithm to produce a resultant (corrected) spectrum.

BRIEF DESCRIPTION OF THE DRAWINGS

FIG. 7(a) is a graph that shows the spectrum of one preferred embodiment of the DichOS device (with $MgF_2$ waveplates) over wavelengths of 170-300 nm with Hg lines and CSA peak positions (underlined) indicated.

FIG. 7(b) is a graph that shows the spectrum of another preferred embodiment of the DichOS device (with quartz waveplates) over wavelengths of 170-300 nm with Hg lines and CSA peak positions (underlined) indicated.

FIG. 8(a) is a graph that shows the spectrum of one preferred embodiment of the DichOS device (with $MgF_2$ waveplates) over wavelengths of 170-600 nm with Hg lines and CSA peak positions (underlined) indicated.

FIG. 9(a) is a graph that shows the spectrum of one preferred embodiment of the DichOS device (with $MgF_2$ waveplates) over wavelengths of 500-2000 nm with Hg lines and CSA peak positions (underlined) indicated.

FIG. 9(b) is a graph that shows the spectrum of another preferred embodiment of the DichOS device (with quartz waveplates) over wavelengths of 500-2000 nm with Hg lines and CSA peak positions (underlined) indicated.

FIG. 13 is a Table showing the configuration of nine exemplary DichOS variants.

FIG. 16(b) is a graph that shows the reduction in CD Error with 3-angle Correction Version A (2° beam angle error) for another preferred embodiment (with quartz waveplates).

FIG. 18(a) is a graph that shows the Amplitude to Residual Conversion Function (ARC) for one preferred embodiment of the DichOS device (with $MgF_2$ waveplates).

FIG. 19(a) is a graph that shows the reduction in CD Error with 3-angle Correction Version C (2° beam angle error) for one preferred embodiment (with $MgF_2$ waveplates).

FIG. 19(b) is a graph that shows the reduction in CD Error with 3-angle Correction Version C (2° beam angle error) for another preferred embodiment (with quartz waveplates).

FIG. 36(b) is a graph that shows published measurements of γ (the normalized temperature derivative of retardation) for crystalline quartz ($SiO_2$).

FIG. 37(b) is a graph that shows the wavelength shift for a temperature change of $\pm 10°$ C. for another preferred embodiment (with quartz waveplates).

FIG. 44 is a Table that shows the results of beam error sensitivity comparison experiments.

DETAILED DESCRIPTION OF THE INVENTION

Figure 1:
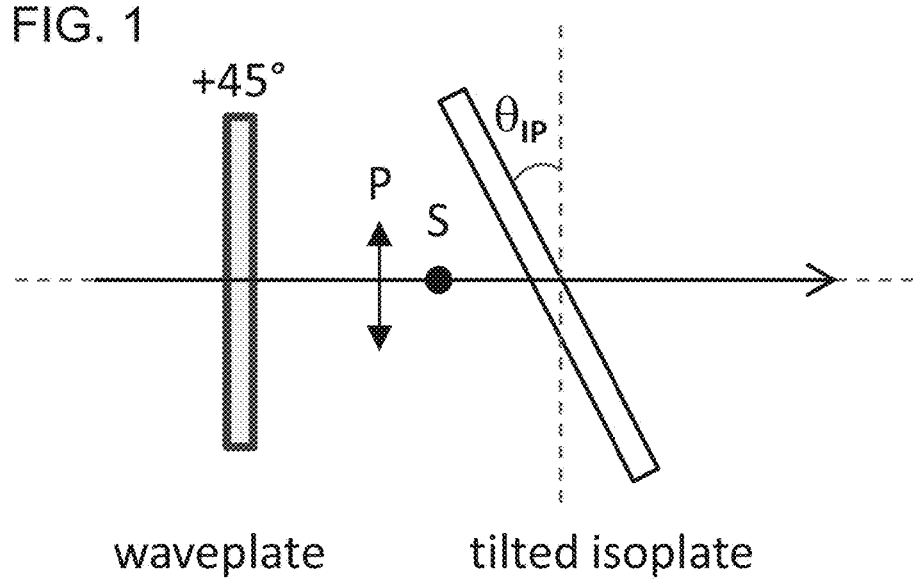
FIG. 1 shows the original design of the optical device.

The present invention features devices which are based on the principle of combining birefringent waveplates and isotropic plates (isoplates) at either normal or tilted incidence to the incoming light beam, so as to generate a predictable circular dichroism (CD) or linear dichroism (LD) spectrum.

Definitions

Unless otherwise specified, the below terms used herein are defined as follows:

The articles "a", "an" and "the" are used herein to refer to one or to more than one (i.e., to at least one) of the grammatical object of the article unless otherwise clearly indicated by contrast. By way of example, "an element" means one element or more than one element.

The term "including" is used herein to mean, and is used interchangeably with, the phrase "including but not limited to."

The term "or" is used herein to mean, and is used interchangeably with, the term "and/or," unless context clearly indicates otherwise.

The term "such as" is used herein to mean, and is used interchangeably with, the phrase "such as but not limited to."

The term "circular dichroism" (CD) as used herein is meant to refer to the difference in the absorption of left-handed circularly polarized light (L-CPL) and right-handed circularly polarized light (R-CPL) and occurs when a molecule contains one or more chiral chromophores (light-absorbing groups).

The term "linear dichroism" (LD) as used herein is meant to refer to a spectroscopic technique that can be used with systems that are either intrinsically oriented, or can be oriented during an experiment by external forces. To measure LD the sample is oriented, then the difference in absorption of light linearly polarized parallel and perpendicular to the orientation axis is measured.

The term "photoelastic modulator (PEM)" as used herein is meant to refer to an optical device used to modulate the polarization of a light source.

The term "waveplate" as used herein is meant to refer to a birefringent plate with crystal (C) axis lying in the plane of the plate surface. The waveplate is constructed out of a birefringent material, and may be coated or uncoated.

The term "isoplate" as used herein is meant to refer to an isotropic plate having optical properties (for example refractive index) which are equal in all directions.

The terms "X axis and "Y axis" as used herein refer to a right handed coordinate system XYZ, in which the positive Z direction is the direction of beam propagation through the device. X and Y therefore lie in a plane normal to the plane of light propagation.

The term "retarder" as used herein is meant to refer to an optical device that alters the polarization state of a light wave travelling through it. In certain embodiments, the retarder is a non-birefringent retarder, for example a Fresnel rhomb or an Oxley prism. In other embodiments, the retarder is a zero order compound retarder or an achromatic retarder.

The term "neutral density (ND) filter" as used herein is meant to refer to a filter that reduces or modifies the intensity of all wavelengths of light approximately equally.

The term "mechanical light attenuator" (MLA) as used herein is meant to refer to a mechanical device that that reduces or modifies the intensity of all wavelengths of light approximately equally by obstructing a part of the beam.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

Any devices or methods provided herein can be combined with one or more of any of the other devices and methods provided herein.

Ranges provided herein are understood to be shorthand for all of the values within the range. For example, a range of 1 to 50 is understood to include any number, combination of numbers, or sub-range including non-integer values from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

Dichroism Standard Devices

The present invention relates to devices for calibrating circular dichroism or linear dichroism spectrometers, including those which comprise a photoelastic modulator (PEM). The present invention also relates to devices for calibrating other photoelastic modulator (PEM) based devices or instruments.

The devices of the present invention are ideally suited for an instrument (e.g. CD or LD spectrometer) incorporating an incoherent light source and an avalanche photodiode detector. Also suitable is an instrument (e.g. CD or LD spectrometer) incorporating an incoherent light source and a photomultiplier detector, although such detectors are known to have polarization sensitivity which can affect the performance of particular DichOS embodiments. Any device designed for measurement of CD and any device designed for measurement of LD is suitable for use with the devices of the present invention. Circular dichroism or linear dichroism spectrometers are commercially available and known to one skilled in the art.

Circular dichroism (CD) is the differential absorption between left and right circularly polarised light on passage through a sample. When light passes through a sample, linear absorbance of the light occurs with the result that the amount of light that passes from the sample is less than the amount of light that passed into the sample. Measuring this difference provides a measurement of the linear absorbance of the sample. When the light is circularly polarized a secondary absorbance component arises from CD. The secondary absorbance component is measured by switching between left and right circularly polarized light, and measuring the resulting difference in absorbance. CD spectra are measured using a circular dichroism spectrometer. Measurements carried out in the visible and ultra-violet region of the electro-magnetic spectrum monitor electronic transitions, and, if the molecule under study contains chiral chromophores then one circularly polarized light (CPL) state will be absorbed to a greater extent than the other and the CD signal over the corresponding wavelengths will be non-zero. A circular dichroism signal can be positive or negative, depending on whether L-CPL is absorbed to a greater extent than R-CPL (CD signal positive) or to a lesser extent (CD signal negative).

Linear dichroism (LD) is a spectroscopic technique that is primarily used to study the functionality and structure of molecules. LD can be defined as the difference between absorption of light polarized parallel and polarized perpendicular to an orientation axis. LD uses linearly polarized light, which is light that has been polarized in one direction only. This produces a wave, the electric field vector, which oscillates in only one plane, giving rise to a classic sinusoidal wave shape as the light travels through space. By using light parallel and perpendicular to the orientation direction it is possible to measure how much more energy is absorbed in one dimension of the molecule relative to the other, providing information to the experimentalist.

In certain embodiments, the devices of the present invention are referred to as "DichOS devices," where the name "DichOS" derives from the term "Dichroism Optical Standard." Preferably, the DichOS devices of the present invention are made entirely from solid optical components, including waveplates (crystalline quartz) and tilted isotropic plates (fused silica), although it is understood that the DichOS devices are not limited to only these components. The optical elements of the DichOS devices need to be precisely aligned. A general principle of operation of the device is as follows: a waveplate(s) converts circularly polarized light (CPL) into linear polarized light; the tilted isoplate(s) gives differential attenuation of V and H linear states (via the Fresnel reflection coefficients). Overall the device has an effective CD signal, which can be calculated.

In one aspect, the invention features a device for calibrating circular dichroism or linear dichroism spectrometers, or other PEM devices, comprising at least one waveplate (Q) providing $(n\pm\frac{1}{4})$ waves of retardation at a defined set of wavelengths; and at least one isotropic plate (P). In certain preferred embodiments of the invention, the device can further comprise at least one waveplate (H) providing $(2n\pm\frac{1}{2})$ waves of retardation at the same wavelengths where Q provides $(n\pm\frac{1}{4})$ waves of retardation. It is understood that n represents any integer value within the range (e.g. 1, 2, 3, 4, 5, 6, 7, 8, 9, 10, 11, 12, 13, 14, 15, 16, 17, 18, 19, 20 . . . ).

The waveplate (Q) can have a thickness (t), and the waveplate (H) can have a thickness (2+4m)t (e.g. 2t, 6t, 10t, 14t, 18t etc.), where m is zero or a positive integer. Without being bound by theory, the reasoning for this is that the (H) waveplate should give a net $\pm\frac{1}{2}$ wave of retardation when the (Q) waveplate gives $\pm\frac{1}{4}$ wave. If the (Q) waveplate retardation (n$\pm\frac{1}{4}$) is multiplied by (2+4m), the result is (N$\pm\frac{1}{2}$) where N is another integer.

In preferred embodiments, the waveplate (Q) has a thickness (t).

In other preferred embodiments, the waveplate (H) has a thickness (2+4m)t.

In other preferred embodiments, the waveplate (H) has a thickness (2t).

In exemplary embodiments, the value of t is preferably any value between 0.01 mm to 5 mm, for example any value between 0.01, 0.02, 0.03, 0.04, 0.05, 0.06, 0.07, 0.08, 0.09, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 to 5.0 mm.

In preferred embodiments, an optimal thickness for the waveplates (Q) used in the device is 0.1037 mm, and the waveplate material is preferably magnesium fluoride ($MgF_2$). The optimal thickness is mainly determined by alignment and test considerations, described infra. In other preferred embodiments, the thickness for the waveplates (Q) used in the device is 0.1328 mm, and the waveplate material is preferably crystalline quartz ($SiO_2$).

According to the present invention, a right handed coordinate system XYZ is defined, in which the positive Z direction is the direction of beam propagation through the device. X and Y therefore lie in a plane normal to the beam propagation axis.

In certain embodiments, the waveplate (Q) or the waveplate (H) may be oriented with its surface normal to a direction of light propagation (Z axis). In further embodiments, the waveplate (Q) or the waveplate (H) is oriented with its crystal axis at an angle about a Z axis, measured from the positive X axis direction. The angle can be between 1° and 90°, for example 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, 90°. Preferably, the angle is 45°.

In another embodiment of the present invention, the waveplate (Q) or the waveplate (H) is subsequently rotated about a Y axis. The angle can be between 1° and 90° about the Y axis, for example 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, 90° about the Y axis.

In another embodiment, the waveplate (Q) or the waveplate (H) is subsequently rotated about an X axis. The angle can be between 1° and 90°, for example 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, 90° about the X axis.

In any of the devices described herein, the isotropic plate (P) may be oriented at an angle about a Y axis. The angle can be between 1° and 90°, for example 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, 90° about the Y axis. In preferred exemplary embodiments, the angle is 20°.

In any of the devices described herein, the isotropic plate (P) may be oriented at an angle about an X axis. The angle can be between 1° and 90°, for example 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, 90° about the X axis. In preferred exemplary embodiments, the angle is 20°.

In any of the configurations of any of the devices of the aspects described herein, the angles can be measured clockwise or anticlockwise.

Figure 2A:
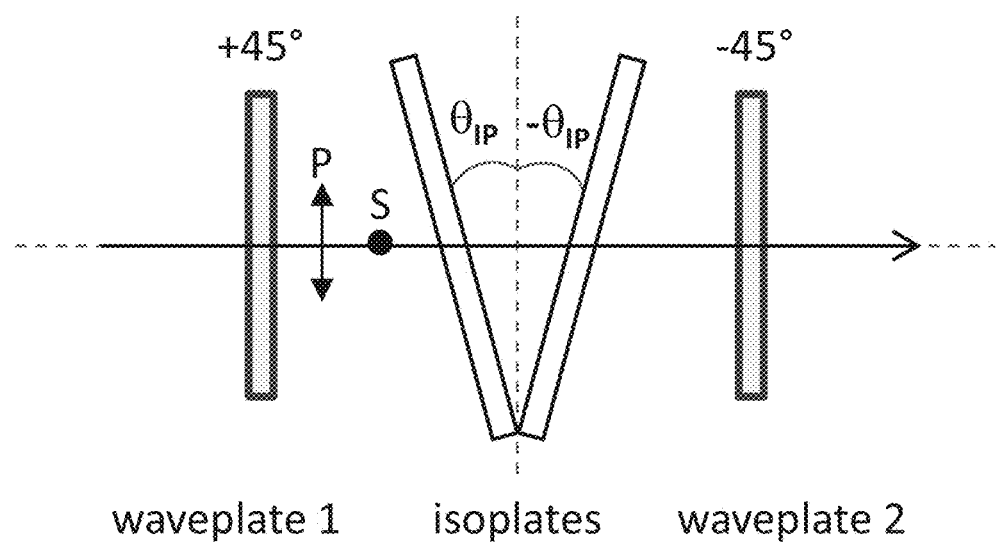
FIG. 2(a) shows a diagram of the optical device in an updated configuration.
Figure 2B:
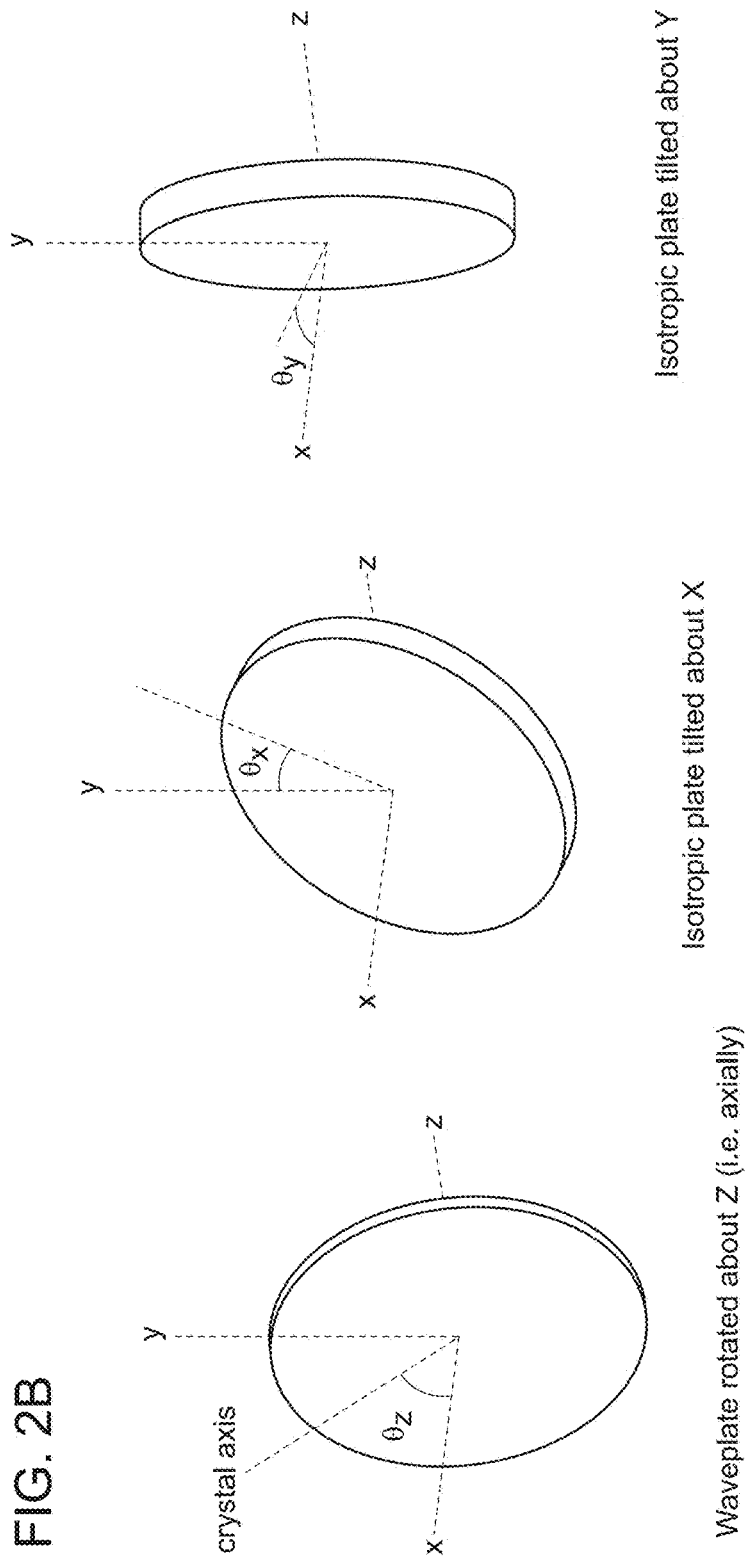
FIG. 2(b) is a schematic that illustrates the orientation of the waveplate or isotropic plates about the Z, X and Y axes.

The schematic shown in FIG. 2b illustrates what is described supra, where a tilt about the X axis is shown as $\theta_X$, where a tilt about the Y axis is shown as $\theta_Y$ and where a tilt about the Z axis is shown as $\theta_Z$.

In certain embodiments of the present invention, two isotropic plates (P) are oriented at equal and opposite angles about the X or Y axis. In other embodiments, the waveplate (Q), the waveplate (H) or the isotropic plate (P) is oriented normal to a plane of light propagation.

In the device, the waveplate (Q), the waveplate (H) or the isotropic plate (P) is coated or uncoated. Coatings provide a way to modify the amplitude profile of the spectrum or provide attenuation of the light beam, whether applied to the waveplates or the isotropic plates. Preferred exemplary coatings may be dielectric or metallic coatings, and the coating may be a single layer or multi-layered.

Waveplates are constructed out of a birefringent material, for which the index of refraction is different for different polarizations of light passing through it. In one embodiment of the above aspects, the waveplate (Q) or the waveplate (H) comprises a birefringent material. Examples include, but are not limited to, crystalline quartz, magnesium fluoride, calcite, alpha barium borate or sapphire.

In one embodiment of the above aspects, the isotropic plate (P) comprises an isotropic material having transparency over the wavelength range of interest for the instrument being calibrated. Examples include, but are not limited to, fused silica, fused quartz, calcium fluoride, lithium fluoride or barium fluoride.

In certain embodiments of the present invention, at least one isotropic plate (P) is replaced by at least two prisms. In order to minimize the angular sensitivity, prisms have to be oriented (i.e. tilted) at a particular angle called the minimum deviation angle. This angle is wavelength dependent.

One or more non-birefringent retarders may be used in place of one or more waveplates of the invention. The non-birefringent retarders may be selected from, but not limited to, a Fresnel rhomb and an Oxley prism. Fresnel rhomb or Oxley prism retarders act like broadband waveplates providing uniform λ/4 or λ/2 retardance over a wider range of wavelengths than possible with birefringent waveplates.

In other embodiments, one or more waveplates may be replaced by a single wavelength compound zero order retarder or an achromatic retarder. The retarder may be any birefringent material. In one exemplary embodiment, a compound zero-order quartz retarder improves performance by combining two multiple-order quartz waveplates with the desired retardance difference. The crystal axis of one plate is orthogonally to the crystal axis of the other, cancelling the large retardance values and leaving only the desired fractional retardance difference. Achromatic retarders provide a constant phase shift independent of the wavelength of light that is used (over a limited range of wavelengths). This wavelength independence is achieved by using two different birefringent crystalline materials. These devices can be used with a coherent light source, since single wavelength retarders and achromatic retarders are almost always antireflection (AR) coated and designed to be usable with lasers.

The devices of the present invention may further comprise a neutral density (ND) filter. An ND filter is a filter that reduces or modifies the intensity of all wavelengths of light approximately equally. An ND filter may be added to the devices described herein without changing the CD signal. This will allow control of the effective absorbance of the standard independently of the CD, allowing calibration measurements to be made over different gain regions of the detector. The ND filter may be disposed in series either before the first waveplate or after the last waveplate.

The devices of the present invention may further comprise a mechanical light attenuator (MLA). An MLA is a filter that reduces or modifies the intensity of all wavelengths of light approximately equally by obstructing a part of the beam. An MLA may be added to the devices described herein without changing the CD signal. This will allow control of the effective absorbance of the standard independently of the CD, allowing calibration measurements to be made over different gain regions of the detector. The MLA may be disposed at any position within the optical assembly.

The device of the present invention may further comprise, but is not limited to, any one or more of the following:
 a motor to rotate or spin the device;
 a manifold or a system for nitrogen purging;
 a means of sealing the optical housing so as to retain a nitrogen atmosphere within the device;
 a polarizer;
 a linearly dichroic sample;
 a detector; and/or
 a processor.

The devices of the present invention have many advantages, including being an out-of-the box solution, where no sample preparation is required. The devices are rugged and long lasting, and there are minimal degradation issues. The devices provide true broadband calibration, with the full relevant wavelength range covered. Very low attenuation enables calibration well into the VUV (170 nm). Accuracy is completely definable from the manufacturing process and known material properties, and the devices described herein have excellent potential to become certified traceable standards.

Uses

Among the uses of the device of the present invention are calibrating circular dichroism spectrometers and calibrating linear dichroism spectrometers.

In using the devices of the present invention, a first spectrum is measured, the device is rotated axially through a fixed angle and a second spectrum is measured. Preferably, the fixed angle is 90° or 180°. A further step of taking the average of the two measured spectra is preferably carried out.

In certain embodiments of the present invention, a first spectrum is measured, the device is rotated axially through a fixed angle and a second spectrum is measured, the device is rotated axially through a further fixed angle and a third spectrum is measured. Preferably, the fixed angles are 45° and 45° or 90° and 90°. The angles may be measured clockwise or anticlockwise.

The measured spectra are processed through an algorithm to produce a resultant (corrected) spectrum.

In other embodiments, the spectrum may be corrected by subtracting the spectrum measured using a device wherein the waveplate (Q), the waveplate (H) or the isotropic plate (P) is oriented normal to a plane of light propagation.

In other embodiments of the present invention, the zero crossings of the measured spectrum (where the curve crosses the X axis) may be used to calibrate the wavelength of the instrument.

The device of the present invention may also allow simultaneous PEM and CD calibration, and simultaneous PEM, CD and wavelength calibration.

The invention is illustrated by the following Examples, which are not intended to be limiting in any way.

EXAMPLES

Example 1—Theory of Optical Device for Calibrating Circular or Linear Dichroism Spectrometers Several optical CD calibration devices have been described in the literature, however these suffer from certain drawbacks which the present invention overcomes. One device (L. A. Nafie, T. A. Kiederling and P. J. Stevens, "Vibrational Circular Dichroism", Jour. Am. Chem. Soc., 98(10), 2715 (1975)) consists of a birefringent sapphire plate (a waveplate) and a linear polarizer and is designed for calibration of VCD (i.e. infra-red CD) spectrometers. Such a device is not applicable to the UV-VIS region for two reasons: 1) The signal produced is much too large (~30,000 mdeg) and is well outside the range of typical UV-VIS CD measurements. Such a signal would saturate the AC electronics channel in a UV-VIS CD instrument. 2) There is no suitable polarizer (one which completely blocks the unwanted polarization state) which would cover the full range of a UV instrument (170 nm to 1000 nm+). Hence use of this device is restricted to VCD calibration at low sensitivity (low AC gain) levels. Another device (B. Norden and S. Seth, "Critical Aspects of Measurement of Circular and Linear Dichroism: A Device for Absolute Calibration", Appl. Spec., 39 (4), 647 (1985)) describes a device consisting of up to four plane parallel tilted dielectric plates, with detailed calculations of the LD signal such plates produce. This device is thus principally a device for LD calibration. Finally, a device is described (I. Z. Steinberg, U.S. Pat. No. 4,003,663, "Device for Calibrating Instrument that Measures Circular Dichroism or Circularly Polarized Luminescence", Yeda Research & Development Co. Ltd., Rohovath, Israel (1977) consisting of a waveplate and a birefringent plate with adjustable tilt angle. This publication describes in some detail the construction of a CPL instrument and how the proposed device may be used to calibrate such an instrument, although with no calculations supplied of the magnitude of signal generated by such a device, with reference made merely to application of the 'well known Fresnel equations'. This device is limited in at least two principal ways: 1) Having an adjustable tilt angle on the isotropic plate severely limits the accuracy at which the angle of this plate can be set, in turn limiting the calibration accuracy. Indeed, it is a novel and surprising finding of the present invention that the angle of the tilted plate is critical to the CD signal produced, and needs to be fixed at a precise angle in order to provide an accurate calibration standard. 2) Like Norden and Seth (supra), it is again assumed that the waveplate is a single wavelength device, and as such the calibration standard is only applicable at a single wavelength. The authors suggest the use of a pockels cell or compensator to provide access to multiple wavelengths, again failing to realize that a standard waveplate can act as an effective ±¼ wave device at multiple wavelengths.

A further drawback of the devices described in the prior art is that they fail to adequately take account of the effect of beam geometry (incident angle and especially divergence) on the CD signals produced. Norden and Seth do examine the sensitivity of the tilt angle of the plates (which is equivalent the beam incident angle) but only with a view to minimizing this sensitivity in the construction rather than implementing methods to correct the error. Steinberg describes a method to align the device in the instrument, minimizing the effect of beam incident angle error. However this method is defined for a CPL instrument rather than for a CD instrument. The present invention incorporates an understanding of beam geometry effects and includes compensation methods, both in the device construction (e.g. arranging the isoplates in a V-configuration) and by the application of axial rotation and use of processing algorithms, to correct for these effects. As such, a much more accurate calibration is possible than with any of the devices described or contemplated in the prior art. This advantage derives from a detailed theoretical understanding of the device which had to be developed ab initio, as no such theoretical treatment is to be found or even suggested in the literature.

None of the devices described in the prior art recognized the utility of employing a second waveplate to restore the circular polarization state of the exit beam, creating a device with pure CD behavior and minimizing the potentially large artifacts resulting from linear polarization bias response in many standard detectors (e.g. photomultipliers).

The original design of the optical device is shown in FIG. 1. In the present example, the basic design was improved on by making at least the following modifications and additions:

The compound, multilayer antireflective (VAR) coated waveplate was replaced by a single uncoated low order quartz waveplate. As in previous iterations of the device, the plate was oriented with its crystal axis at 45° degrees from horizontal. The reduced reflection coefficients in the UV and red, combined with the true low-order character of the waveplate, substantially reduced the fringing effects seen previously.

The tilted fused silica isotropic plate (isoplate) was replaced by two plates in a V configuration ('V-plates'). The purpose of this was to reduce the angular sensitivity, since a positive ray angle error on one plate would be compensated by a corresponding negative error on the other plate. A design based on a pair of prisms was also investigated. It was found that for optimal performance the prisms had to be set at the minimum deviation angle, which is wavelength dependent.

A second single crystal quartz waveplate, identical to the first, was positioned after the V-plates, with its crystal axis at 90° to that of the first plate. The purpose of this second plate was to convert linear states back into circular states, in theory eliminating the effect of detector polarisation bias on the measured signal.

A diagram of the device in this updated configuration is shown in FIG. 2.

Without being bound by theory, the basic principle of the device is as follows. At particular wavelengths (where the waveplate has a net +¼ wave or −¼ wave retardation), left and right circular polarised states hitting the first waveplate are converted into vertical and horizontal linear polarised states. These linear states then meet the V-plates where they are subject to linear diattenuation (or linear dichroism) due to differential Fresnel reflection from the tilted surfaces. The second waveplate converts the linear states back into circular states, so that overall the device appears to have a circular diattenuation (or circular dichroism) relative to the input state. At other wavelengths, circular states are converted to elliptical states of varying ellipticity. These in turn suffer a lower diattenuation at the V-plates.

Overall then, the spectrum consists of a series of negative and positive peaks, where the peak positions are determined by the waveplate retardation, and the peak magnitudes are determined by the V-plates (isoplates) diattentuation, both of which vary with wavelength.

The linear dichroism of the V-plates in closed form can be described with the following expression:

$$LD_{Vplates}(\lambda) = \frac{-2(n(\lambda)^2 - 1)^2 \cdot \sin^2\theta_{IP} \cdot K}{(n(\lambda)^2 + 1)\{(n(\lambda)^2 + 1)\sin^2\theta_{IP} - 2n(\lambda)^2\}} \quad (1)$$

Figure 3:
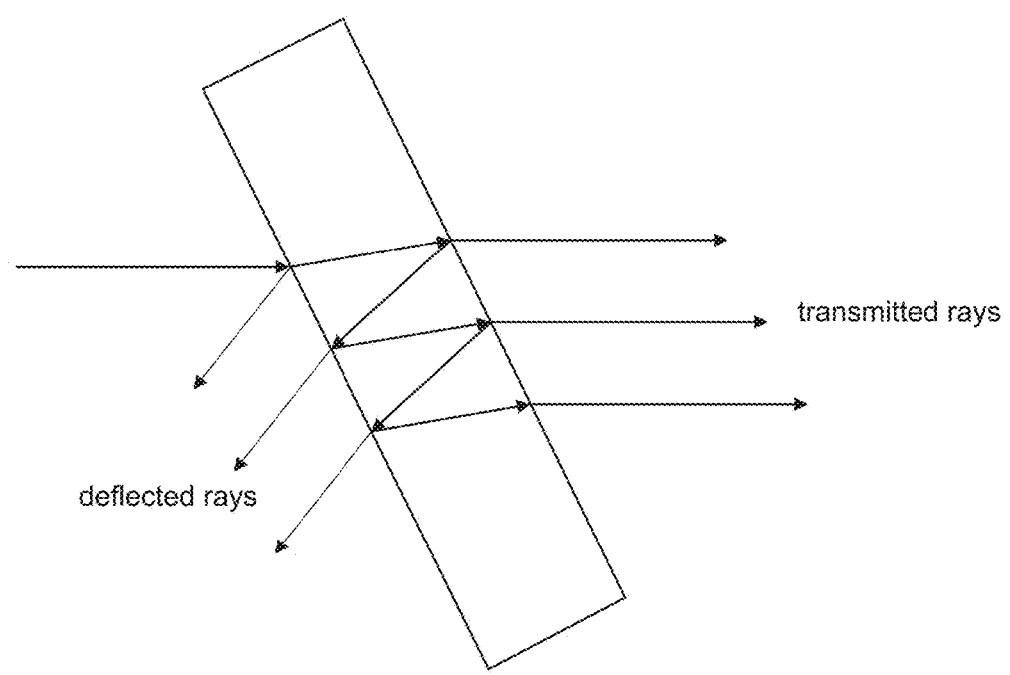
FIG. 3 shows rays transmitted and deflected by a single plate.

This equation includes the contribution from the infinite series of rays which undergo reflections inside each isoplate. Those rays which are deflected by the plate are assumed to rapidly migrate out of the beam and hence do not contribute to the final signal as shown in FIG. 3.

The CD signal of the whole device is then given by:

$$CD_{DichOS}(\lambda) = \sin 2\theta_C \cdot \sin \Phi(\lambda) \cdot LD_{Vplates}(\lambda) \quad (2)$$

The contributions of multi-pass ray paths which are reflected at normal interfaces (e.g. at waveplates or the detector surface) are not included in the above equations. As will be shown later, these have a very small effect on the overall signal.

The symbols in the above equations have the following definitions:
$\lambda$: Wavelength
$\theta_C$: Crystal axis direction of first waveplate measured from horizontal (X axis)
$\Phi(\lambda)$: Retardation of waveplate in radians
$n(\lambda)$: Refractive index of isoplate material (fused silica)
$\theta_{IP}$ Tilt angle of isoplates (or half angle of V-plates)
K: Scaling constant to render the result in millidegrees The value of K may be shown to be:

$$K = \frac{180 \times 10^3}{2\pi} = 28647.89 \quad (3)$$

The retardation of the waveplate (in radians) is given by:

$$\Phi(\lambda) = \frac{B(\lambda) \cdot t_{WP} \cdot 2\pi}{\lambda} \quad (4)$$

Where
$B(\lambda)$: Birefringence ($n_e - n_o$) of waveplate material (e.g. quartz)
$t_{WP}$: Waveplate thickness
Example Spectrum The theoretical CD spectrum of the device is computed based on the following design parameters used for a prototype configuration (which represents a physically realizable device):
$\lambda_{des}$=532 nm wavelength at which waveplate retardation is specified
$\Phi_{des}$=2.5 Retardation in waves at $\lambda_{des}$ (×2π to convert to radians)
$\theta_{IP}$=20° Half angle of V-plates
$\theta_C$=45° Crystal axis of first waveplate The material of the V-plates is assumed to be fused silica while that of the waveplates is assumed to be crystal quartz.

Using Equation 4, the thickness of the waveplate may be computed, giving:

$T_{wp}$=0.14465 mm Thickness of waveplate

Figure 4:
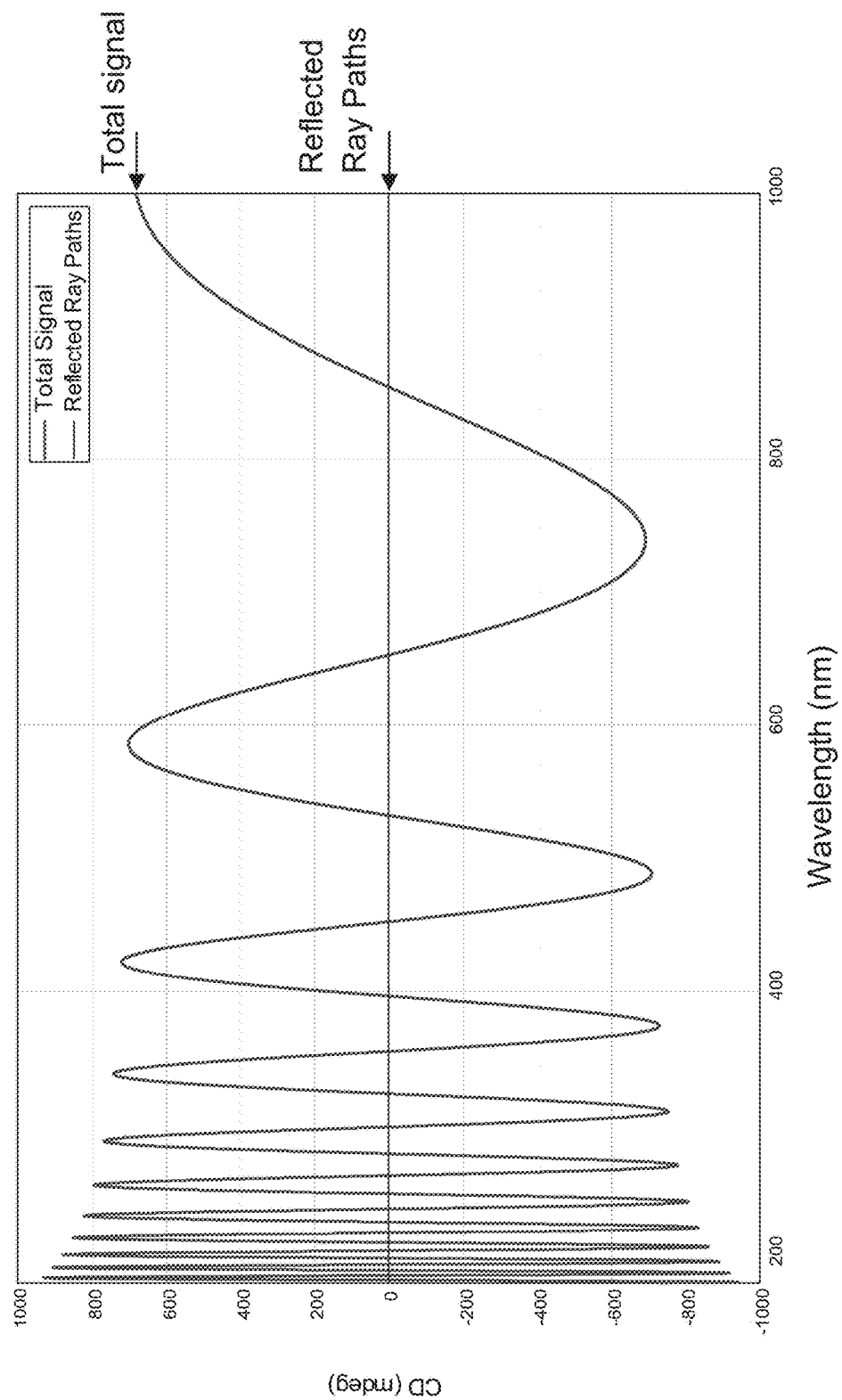
FIG. 4 is a graph that shows a theoretical CD spectrum of a prototype configuration of the optical device.

The theoretical CD spectrum corresponding to the above parameters is shown in FIG. 4.

It can been seen from FIG. 4 that there is good signal amplitude covering most of the dynamic range of a typical CD instrument (which is ~1000 mdeg). The retardation value of 2.5 waves produces more peaks than the original device which used an effective zero order waveplate. As will be explained herein below, it turns out that the device behaves like a true CD sample at the positive and negative peak positions, so a greater number of peaks is in fact an advantage provided the width of the peaks does not become too narrow at the UV end of the spectrum.

Figure 5:
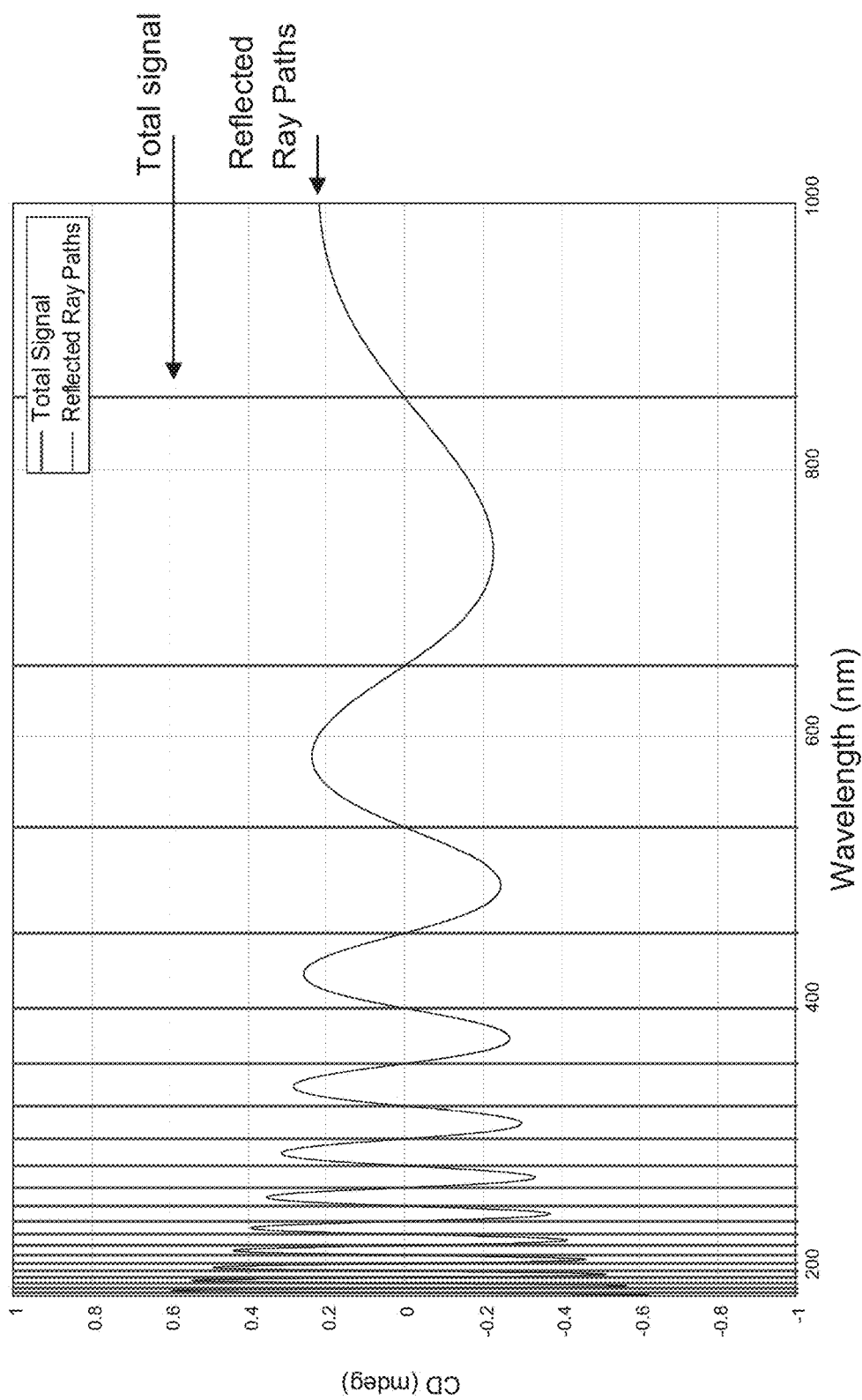
FIG. 5 is a graph that shows a theoretical spectrum of a prototype configuration of the optical device (close up).

The model of the theoretical spectrum presented herein includes consideration of ray paths having up to two internal reflections at the waveplate interfaces (higher order reflections have negligible amplitude). Accounting also for a 30% reflection from the detector surface as well (which is reasonable for a LAAPD detector) a total of six ray paths were included in the calculation in addition to the direct path which generates the main signal. The magnitude of the contribution from the reflected paths can be seen from the lighter trace in FIG. 4 and FIG. 5 (where the Y axis has been magnified by a factor of 1000). As shown in these Figures, the reflected contributions to the final signal are extremely small, at less than 0.3 mdeg and contributing less than 0.1% of the total signal. This fraction would be smaller still for a device with a larger CD magnitude (i.e. a larger angle $\theta_{IP}$). These reflection effects may therefore be assumed to be negligible. This is in contrast to the original optical device, where the reflected contributions had a considerable impact on the measured signal and gave rise to very distinct fringes in the spectrum.

Effect of Isoplate Angle $\theta_{IP}$ on Spectrum Magnitude

Figure 6:
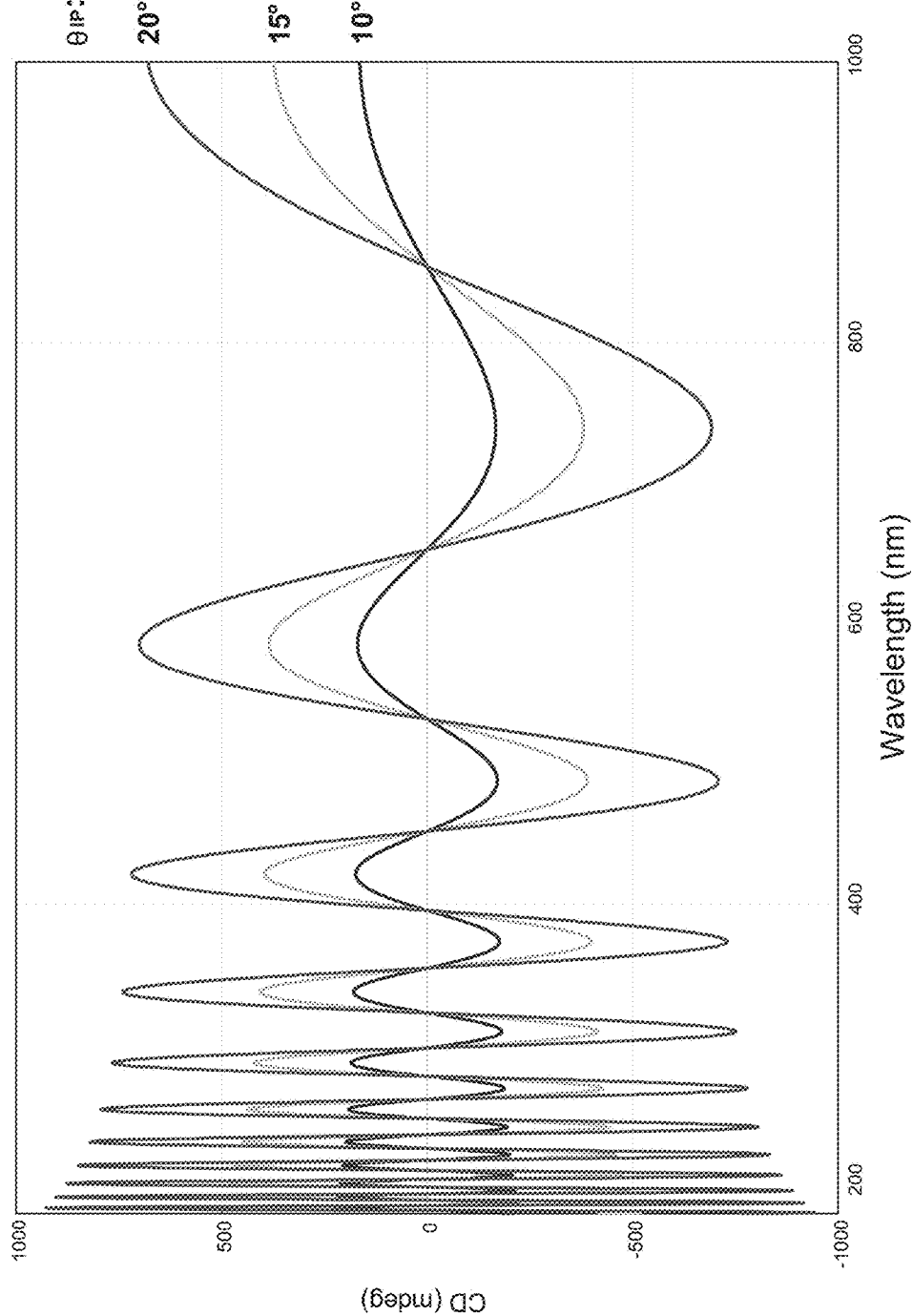
FIG. 6 is a graph that shows a theoretical CD spectrum of a prototype configuration of the optical device for three different values of the isotropic plate angle ($\theta_{IP}$)

To illustrate how the isoplate angle affects the magnitude of the CD spectrum for the device, the theoretical spectrum is plotted in FIG. 6 for three different values of $\theta_{IP}$: 10°, 15° and 20° for a prototype configuration of the device. Other design parameters are identical to those used supra.

At $\theta_{IP}$=20° the upper end of the dynamic range for a typical CD instrument is approached. Accordingly, the most appropriate choice of value for $\theta_{IP}$ should take account of tolerance considerations among other factors, as will be discussed infra.

Jones Matrix Analysis

Given:

$T_X$: Transmission of V-plates for light polarised along X (horizontal)

$T_Y$: Transmission of V-plates for light polarised along Y (vertical)

$\Phi$: Phase retardation of each waveplate

Where $\Phi$ is given by equation (4) and $T_X$ and $T_Y$ are given by:

$$T_X = \frac{4n^2 \cos^2\theta_{IP}(n^2 - \sin^2\theta_{IP})}{(\sin^2\theta_{IP} - n^4\cos^2\theta_{IP} - n^2)^2} \quad (5)$$

$$T_Y = \frac{4n^2 \cos^2\theta_{IP}(n^2 - \sin^2\theta_{IP})}{(\sin^2\theta_{IP} - \cos^2\theta_{IP} - n^2)^2} \quad (6)$$

The full Jones matrix of the device (assuming implicit wavelength dependence) is given by:

$$M_{WPVP} = \frac{1}{2}\begin{bmatrix} \sqrt{T_X} + \sqrt{T_Y} + \cos(\Phi)\cdot(\sqrt{T_X} - \sqrt{T_Y}) & \sin(\Phi)\cdot(\sqrt{T_x} - \sqrt{T_y})\cdot i \\ -\sin(\Phi)\cdot(\sqrt{T_X} - \sqrt{T_y})\cdot i & \sqrt{T_X} + \sqrt{T_Y} - \cos(\Phi)\cdot(\sqrt{T_X} - \sqrt{T_Y}) \end{bmatrix} \quad (7)$$

Certain characteristics of the device can be determined by computing the normalised polarisation eigenstates (i.e. the eigenvectors) of this matrix along with their associated eigenvalues. Accordingly, the following results are obtained:

$$V_1 = \begin{bmatrix} i\sqrt{1+\cos\Phi} \\ \frac{\sin\Phi}{\sqrt{1+\cos\Phi}} \end{bmatrix}, \lambda_1 = \sqrt{T_X}\cdot e^{i\Phi} \quad (8)$$

$$V_2 = \begin{bmatrix} -i\sqrt{1-\cos\Phi} \\ \frac{\sin\Phi}{\sqrt{1-\cos\Phi}} \end{bmatrix}, \lambda_2 = \sqrt{T_Y}\cdot e^{i\Phi} \quad (9)$$

The dot product of $V_1$ and $V_2$ is zero, indicating that the eigenstates are orthogonal for all values of retardation $\Phi$. The eigenvalues $\lambda_1$ and $\lambda_2$ indicate amplitude attenuation by $\sqrt{T_X}$ and $\sqrt{T_Y}$ (corresponding to irradiance attenuation by $T_X$ and $T_Y$) for eigenstates $V_1$ and $V_2$. The factor $e^{i\Phi}$ simply represents the net phase shift of the emerging beam after passing through the two crossed waveplates of retardance $\Phi$. Since this phase shift applies to both eigenstates it does not change the polarisation state and can be factored out.

To gain a better understanding of the eigenvectors in equations (8) and (9), their numerical values can be computed for a range of values of the waveplate retardation $\Phi$. In each case the Jones vector is phase normalised to be in standard form so that the associated polarisation state can be easily inferred. The results are shown in Table 1 below:

TABLE 1

| Retardation ($\Phi$) | 0 | $\frac{\pi}{2}$ | $\pi$ | $\frac{3\pi}{2}$ | $2\pi$ | $\frac{5\pi}{2}$ |
|---|---|---|---|---|---|---|
| Retardation in waves | 0 | 1/4 | 1/2 | 3/4 | 1 | 5/4 |
| $V_1$ | $\begin{bmatrix}1\\0\end{bmatrix}$ | $\frac{1}{\sqrt{2}}\begin{bmatrix}1\\-i\end{bmatrix}$ | $\begin{bmatrix}0\\1\end{bmatrix}$ | $\frac{1}{\sqrt{2}}\begin{bmatrix}1\\i\end{bmatrix}$ | $\begin{bmatrix}1\\0\end{bmatrix}$ | $\frac{1}{\sqrt{2}}\begin{bmatrix}1\\-i\end{bmatrix}$ |
| $V_2$ | $\begin{bmatrix}0\\1\end{bmatrix}$ | $\frac{1}{\sqrt{2}}\begin{bmatrix}1\\i\end{bmatrix}$ | $\begin{bmatrix}1\\0\end{bmatrix}$ | $\frac{1}{\sqrt{2}}\begin{bmatrix}1\\-i\end{bmatrix}$ | $\begin{bmatrix}0\\1\end{bmatrix}$ | $\frac{1}{\sqrt{2}}\begin{bmatrix}1\\i\end{bmatrix}$ |
| $V_1$ Pol State | HOR | LCP | VER | RCP | HOR | LCP |
| $V_2$ Pol State | VER | RCP | HOR | LCP | VER | RCP |
| $V_1$ Ellipticity ($\chi_1$) | 0° | −45° | 0° | 45° | 0° | −45° |
| $V_2$ Ellipticity ($\chi_2$) | 0° | 45° | 0° | −45° | 0° | 45° |

From Table 1 the following can be deduced (where n=integer):

When $\Phi$=n$\pi$, the device has exactly the characteristics of a linear diattenuator or LD sample. This corresponds to the zero crossings in FIG. 4 and FIG. 6, and occurs when the waveplates are operating effectively in zero wave or half wave mode.

When $\Phi=(2n+1)\pi/2$, the device has exactly the characteristics of a circular diattenuator or CD sample. This corresponds to the negative and positive peak positions in FIG. 4 and FIG. 6, and occurs when the waveplate is operating effectively in quarter wave or minus quarter wave mode.

More generally, it can be shown that the device always acts as a diattenuator to orthogonal elliptical polarisation states with azimuth and ellipticity angles given by:

$$\psi_1=0°, \chi_1=-\tfrac{1}{2}\sin^{-1}(\sin \Phi) \qquad (10)$$

$$\psi_2=90°, \chi_2=\tfrac{1}{2}\sin^{-1}(\sin \Phi) \qquad (11)$$

Hence the device could generally be described as behaving like a sample with elliptical dichroism (ED) for oppositely handed elliptical states with azimuths lying along X (horizontal) and Y (vertical) and wavelength dependent ellipticity varying continuously through LCP, linear and RCP states.

Note that the expressions for ellipticity could be simplified further to $(\chi_1=-\Phi/2)$ and $(\chi_2=\Phi/2)$, but keeping them in the above form forces the results to lie in the more meaningful range of (−45° to +45°), which covers the full gamut of elliptical states from LCP (−45°) through linear (0°) to RCP (+45°). These values are shown in the final row of Table 1.

Accordingly, a key point arising from the discussion above is that, at the negative and positive peak positions on the spectrum (see FIG. 4), the optical device behaves in theory (assuming perfect alignment) exactly like a true CD sample. At the very least, these peak points on the spectrum should be able to be exploited to provide a CD magnitude reference. Although the detection chain should be insensitive to non-circular states, defects in the optics and detector can result in these signals appearing as artefacts. The magnitude of these artefacts (combined with a full consideration of the construction tolerances of the device) will determine whether the device is also viable as a CD reference standard away from the peak positions.

Augmentation with ND or MLA Filters

The optical device described in the foregoing example is an intrinsically low absorbance standard, since the only optical losses are due to surface reflections at the various interfaces (in particular those of the V-plates). This is a useful characteristic as it allows spectra to be recorded down to very low wavelengths (approaching 170 nm).

In order to create a standard which is more representative of the absorbance of a true CD sample, and to allow testing of the detector in different gain regimes, it is a simple matter to augment the optical device with a neutral density filter (NA) or a mechanical light attenuator (MLA). In this way the absorbance characteristic of the device may be controlled completely independently of the CD characteristic, allowing a number of combinations of ND/MLA filter and V-plates to be implemented. A suitable place for an ND filter is either before the first waveplate or after the second waveplate (see FIG. 2), since in these locations the sensitivity to the angular alignment of the filter is minimized. An MLA filter is not angularly sensitive and so may located at any position within the device.

Example 2—Waveplate Specifications

The design of the production version of DichOS requires a careful consideration of the waveplate specification, in particular with respect to the following design requirements:

A reasonable number of peaks across the entire spectral region (170 nm to 1000 nm+) are required, without the peak density becoming so great in the UV that the peak width approaches a typical spectral bandwidth setting for CD measurement (~1 nm). It is useful to have a peak somewhere in the region 1000 nm to 1700 nm to provide a high calibration point for extended wavelength range CD instruments.

Thin, low order waveplates are preferable because that they have lower temperature dependence and wider acceptance angles. However, the waveplate should not be so thin that structural integrity, fragility and fabrication difficulties become an issue.

It is highly desirable that some of the peaks in the DichOS spectrum correspond closely with known strong lines from standard calibration light sources, such as Hg, Ar, Ne an Kr. This would enable setup, alignment, and verification of the DichOS standard using test jigs incorporating standard line sources.

With reference to the above considerations (and especially the last one), a number of suitable waveplate specifications have been found for the (Q) waveplate, this being the one positioned at the front or at the front and rear of the DichOS device. The (H) waveplate (which is positioned at the middle of the device in some variants, e.g. DichOS-8 and DichOS-9) may generally be assumed to be (2+4m) times the thickness of the (Q) waveplate, where m is a positive integer, the preferred solution being m=0 where the (H) waveplate is exactly twice the thickness of the (Q) waveplate.

Waveplate Candidates

Waveplate candidates were found by conducting a thorough search in the thickness region 0.05 mm to 0.25 mm. The lower limit was set by manufacturing and fragility considerations. Thicknesses above the upper limit produced excessive peak density in the UV region. The search was conducted for waveplates made of crystalline quartz ($SiO_2$) and magnesium fluoride ($MgF_2$). Candidates were selected which had close peak correspondences with as many line source wavelengths as possible listed in Table 2 below. These lines were chosen because they have strong intensity and are well separated from neighbouring lines, allowing convenient selection using bandpass interference filters. In addition, peaks lying close to the CSA calibration wavelengths (290.5 nm and 192.5 nm) were also considered favourable since they would enable direct single point comparison of DichOS with CSA and ACS calibration samples.

TABLE 2

| Wavelength (nm) | Source |
| --- | --- |
| 184.9 | HgAr |
| 253.7 | HgAr |
| 313.2 | HgAr |
| 365.0 | HgAr |
| 435.8 | HgAr |
| 546.1 | HgAr |
| 696.5 | HgAr |
| 763.5 | HgAr |
| 1529.6 | HgNe |

Given the above search parameters, a total of four viable waveplate candidates were identified. These are listed in Table 3 below. The most preferable candidate is listed first.

TABLE 3

|   | Thickness (mm) | Material | Peak Matches (nm) | Notes |
|---|---|---|---|---|
| 1 | 0.1037 | MgF2 | 184.9, 253.7, 546.1, 696.5, ~1529.6 | Good matches with several Hg lines. No CSA peak matches. This is the favored candidate as the peak density is not too great in the UV. |
| 2 | 0.1328 | Quartz | 184.9, ~192.5, 253.7, 290.5, ~313.2, 546.1, ~696.5, ~1529.6 | Plenty of matches including an exact match at 290.5 nm (CSA peak). Peak density is a little higher than desired in the UV region, making this the second favored candidate. |
| 3 | 0.0748 | Quartz | 184.9, 192.5, 253.7, 546.1 | No peak in 1000 nm-1700 nm range. Lower end of practical thickness range (could be fragile and hard to manufacture) |
| 4 | 0.1785 | Quartz | 184.9, 253.7, 313.2, 365.0 | Upper peak at 1234 nm. High peak density in VUV. No peak in visible region. No CSA peak matches |

~indicates and approximate match
CSA peak matches are underlined

Primary Waveplate Candidate

Figure 8B:
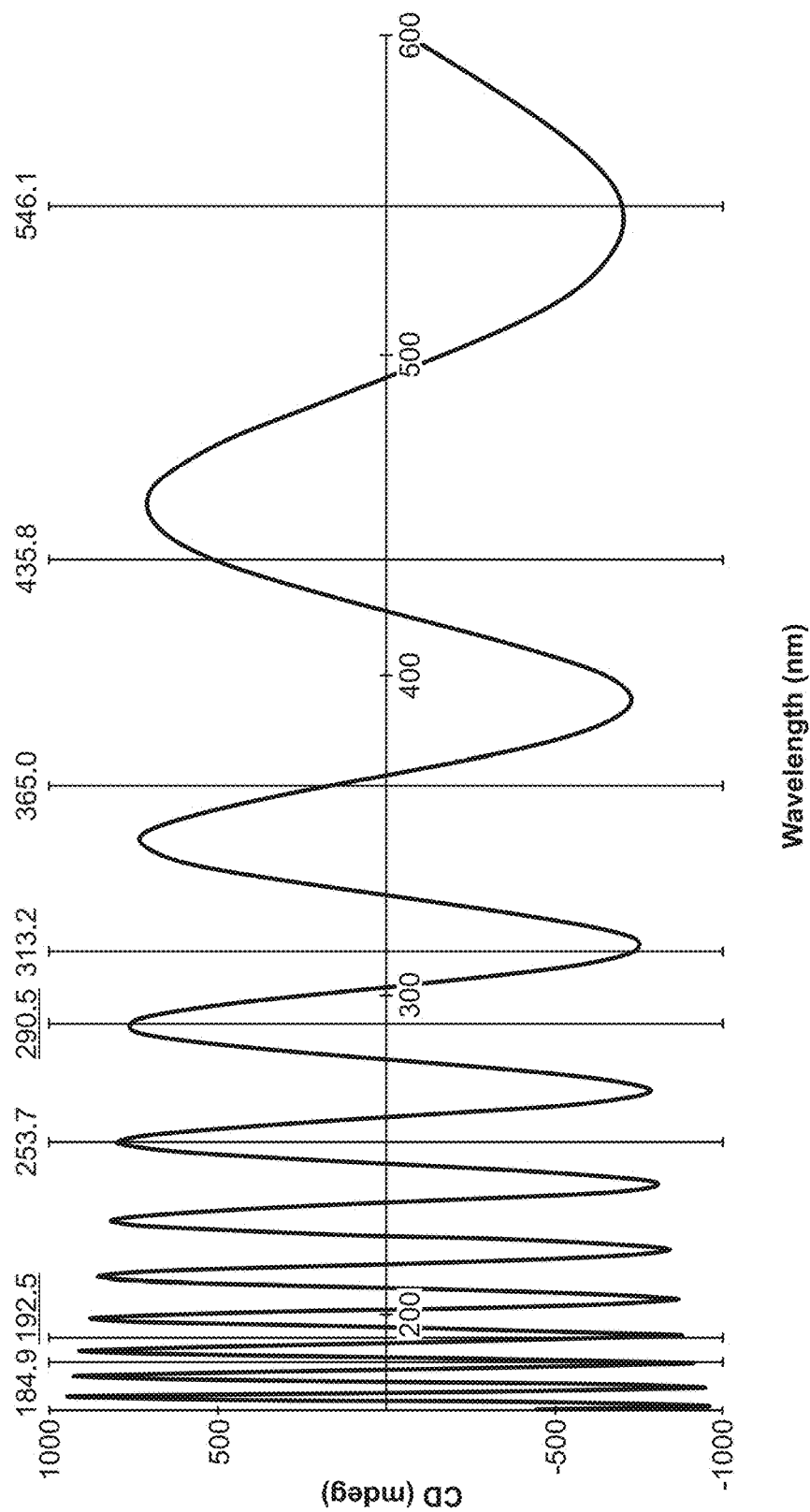
FIG. 8(b) is a graph that shows the spectrum of another preferred embodiment of the DichOS device (with quartz waveplates) over wavelengths of 170-600 nm with Hg lines and CSA peak positions (underlined) indicated.

The primary and secondary waveplate candidates identified in the study described supra above (item 1 in Table 3) are next examined in greater detail. The spectra of these candidates mounted in a DichOS device is shown over various wavelength ranges in FIG. 7, FIG. 8 and FIG. 9. The preferred line source wavelengths and CSA calibration wavelengths (underlined) are also indicated in these figures. The close correspondence of a number of these lines with DichOS peaks is clearly visible in the figures.

The complete set of peak positions for a DichOS device constructed with waveplate candidate 1 is shown in Table 4 below together with corresponding line source wavelength matches. Approximate matches are indicated with a tilde (~).

TABLE 4

| Peak No. | Peak Wavelength (nm) | Line Source/CSA Match (nm) |
|---|---|---|
| 1 | 175.29 | |
| 2 | 184.26 | 184.9 |
| 3 | 194.26 | |
| 4 | 205.64 | |
| 5 | 218.79 | |
| 6 | 234.24 | |
| 7 | 252.72 | 253.7 |
| 8 | 275.25 | |
| 9 | 303.30 | |
| 10 | 339.15 | |
| 11 | 386.46 | |
| 12 | 451.54 | |
| 13 | 546.20 | 546.1 |
| 14 | 695.61 | 696.5 |
| 15 | 964.10 | |
| 16 | 1577.53 | ~1529.6 |

The complete set of peak positions for a DichOS device constructed with waveplate candidate 2 is shown in Table 5 below together with corresponding line source and CSA wavelength matches. Approximate matches are indicated with a tilde (~).

TABLE 5

| Peak No. | Peak Wavelength (nm) | Line Source/CSA Match (nm) |
|---|---|---|
| 1 | 170.12 | |
| 2 | 172.46 | |
| 3 | 175.05 | |
| 4 | 177.92 | |
| 5 | 181.14 | |
| 6 | 184.75 | 184.9 |
| 7 | 188.81 | |
| 8 | 193.43 | ~192.5 |
| 9 | 198.68 | |
| 10 | 204.70 | |
| 11 | 211.66 | |
| 12 | 219.75 | |
| 13 | 229.23 | |
| 14 | 240.47 | |
| 15 | 253.94 | 253.7 |
| 16 | 270.30 | |
| 17 | 290.50 | 290.5 |
| 18 | 315.94 | ~313.2 |
| 19 | 348.79 | |
| 20 | 392.54 | |
| 21 | 453.21 | |
| 22 | 542.13 | 546.1 |
| 23 | 683.22 | ~696.5 |
| 24 | 936.62 | |
| 25 | 1499.45 | ~1529.6 |

CSA peak matches are underlined

It is useful for line source wavelengths to lie close to peaks in the DichOS spectrum since at these points the signal is maximized and the behavior of the device is most 'CD like'. However the match does not have to be exact, and indeed this would not in general be possible for more than one or possibly two wavelengths.

According to exemplary embodiments of the present invention, an optimal specification for the (Q) waveplate used in the DichOS family of devices has been found. The specification is as follows:
  Material: Magnesium Fluoride ($MgF_2$)
  Thickness: 0.1037 mm
  Among a total of four possible candidates which were found, this specification had the most favorable properties, in particular:

It has the advantage of being thin (low temperature dependence and wide acceptance angle) without being outside manufacturing limits or overly prone to shock damage due to fragility It has good peak density without peaks being too narrow or overly crowded in the UV. There is good peak correspondence with a number of strong standard source calibration lines, including the visible Hg line 546.1 nm. This is of great utility for alignment and testing/verification of the DichOS device on specialized test jigs.

The lowest peak lies just above 170 nm and the highest occurs near 1600 nm, enabling calibration of the full CD measurement range (including extended range instruments). There are no peaks corresponding closely to the 290.5 nm and 192.5 nm peaks of a traditional CSA standard. However comparison with CSA calibration is easily achieved via interpolation of calibration points at neighboring peaks.

The material comprising the optimal waveplate ($MgF_2$) is well characterized and has excellent transmission in the VUV region (below 200 nm).

For those DichOS variants which also include an (H) waveplate, the preferred thickness would be exactly twice the thickness of (Q), namely 0.2074 mm. More generally, $t_H = (2+4m)t_Q$, where m is a positive integer or zero.

Example 3—Configuration Variants and Correction for Beam Incidence and Divergence Errors The next set of experiments describes the optimization of the optical device, termed herein as "DichOS."

The studies described herein were, in part, aimed at finding ways to reduce the errors associated with beam incidence angle and beam divergence (henceforth referred to as "beam errors"). As discussed supra, these errors can be problematic for the viability of the device because, being dependent on the characteristics of the instrument measuring beam, they cannot be controlled directly via tolerancing or metrology during manufacture of the DichOS standard itself. Instead, methods are preferred which either enable subtraction of these errors, or which render the device less sensitive to beam incidence angle and divergence. These improved devices are much less sensitive to beam angular errors and divergence, and much less sensitive to detector polarization bias (as seen with photomultipliers). Exemplary preferred approaches are described infra.

In the simulation studies, for each DichOS variant, a non-sequential optical model was built and analyzed. These models incorporated the effects of multiple reflections from optical surfaces and can thus be assumed to have a high degree of accuracy.

This example describes nine different DichOS variants that have been identified and analyzed; however it is to be understood that the number of DichOS variants is not limited to those described herein. As set forth in the description, any number of DichOS variants is envisioned by the present invention.

Specification of DichOS Variants

Figure 10:
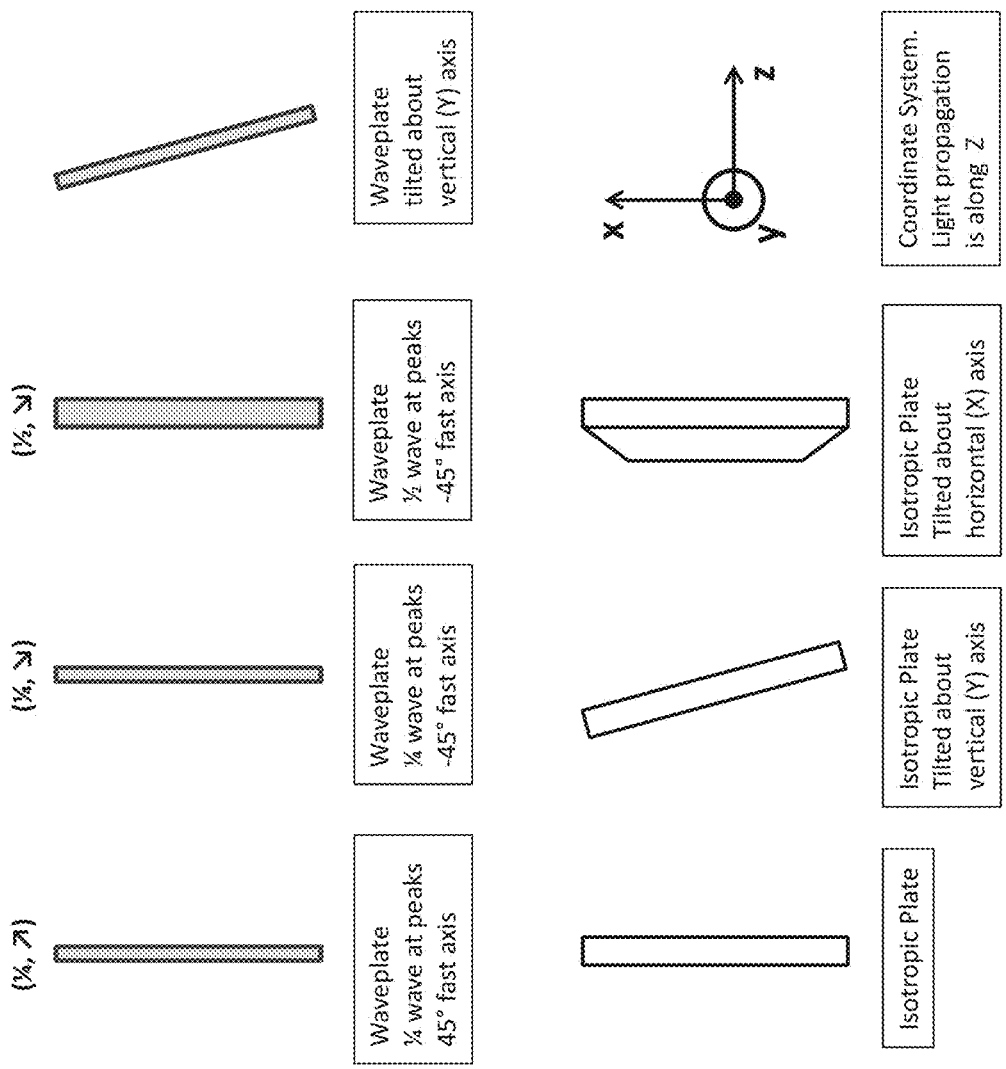
FIG. 10 is a schematic diagram showing the symbols for the DichOS elements.

The configuration of each DichOS variant may be specified diagrammatically using the schematic symbols shown in FIG. 10, which also defines the coordinate system used. The viewpoint is plan (i.e. looking down from above). The waveplate crystal axis angle is measured anticlockwise from the positive X axis (i.e. towards Y). A waveplate which has a net quarter wave of retardation at the CD spectrum peak positions carries the symbol ¼, while a waveplate with a net half wave of retardation at the CD peak positions carries the symbol ½. Away from the peaks the retardations will differ from these values.

In exemplary embodiments, the device for calibrating circular dichroism or linear dichroism spectrometers comprises at least one waveplate (Q) providing (n±¼) waves of retardation at a defined set of wavelengths; and at least one isotropic plate (P). The device, in further exemplary embodiments, further comprises at least one waveplate (H) providing (2n±½) waves of retardation at the same wavelengths where Q provides (n±¼) waves of retardation. It is assumed that n represents any integer.

Classification Scheme

There are many different ways that waveplates and tilted plates can be combined to create a CD/LD standard. A classification scheme has been devised so that the configuration of any DichOS variant can be specified without the need to create a schematic drawing. The scheme is based on concatenation of the symbols defined below, and shown in FIG. 13.

Plate Symbols:
Q: waveplate providing ½ wave retardation at peak positions.
H: waveplate providing ½ wave retardation at peak positions.
P: isotropic plate (isoplate).

Subscripts:
N: plate oriented normal to beam.
+Y: plate tilted clockwise about Y axis.
−Y: plate tilted anticlockwise about Y axis.
Y: plate tilted clockwise or anticlockwise about Y axis (direction non important).
+X: plate tilted clockwise about X axis.
−X: plate tilted anticlockwise about X axis.
X: plate tilted clockwise or anticlockwise about X axis (direction non important).

For example, one DichOS variant can consist of a normal ¼ waveplate followed by an isoplate tilted about Y, where the direction of tilt is unimportant. It thus has the classification ($Q_N P_Y$).

This classification scheme does not specify the crystal axis directions in the waveplates. It is assumed that the correct directions can always be inferred from the configuration, based on the required waveplate functions (convert, rotate or restore).

Beam Error Correction Methods

The measuring beam in a CD instrument is not perfect, for example it may strike the sample at an off-normal angle and will have some divergence (i.e. not be perfectly collimated). The DichOS standard is sensitive to these beam imperfections.

Accordingly, three methods have been discovered by which the beam related errors (due to incident beam angle and beam divergence) can be corrected, referred to as "rotate & average correction" "N-plates correction" and "3-angle correction," and are described infra.

Rotate & Average Correction

A surprisingly effective way of reducing beam errors was found, termed "rotate & average Correction" The method comprises, but is not limited only to, the following steps:
Record one spectrum
Rotate the whole DichOS device axially through a fixed angle (90° or 180° depending on the variant).
Record a second spectrum.
Take the average of the two recorded spectra (inverting the second if they are of opposite sign).

The principle behind this method is that the beam errors for one axial orientation are approximately equal and opposite to those for the other orientation, so the averaging method causes them to mutually cancel out. The correction is not perfect but in most cases reduces the beam error substantially. The device orientation around X and Y needs to be held stable between the two measurements.

N-Plates Correction

Figure 11:
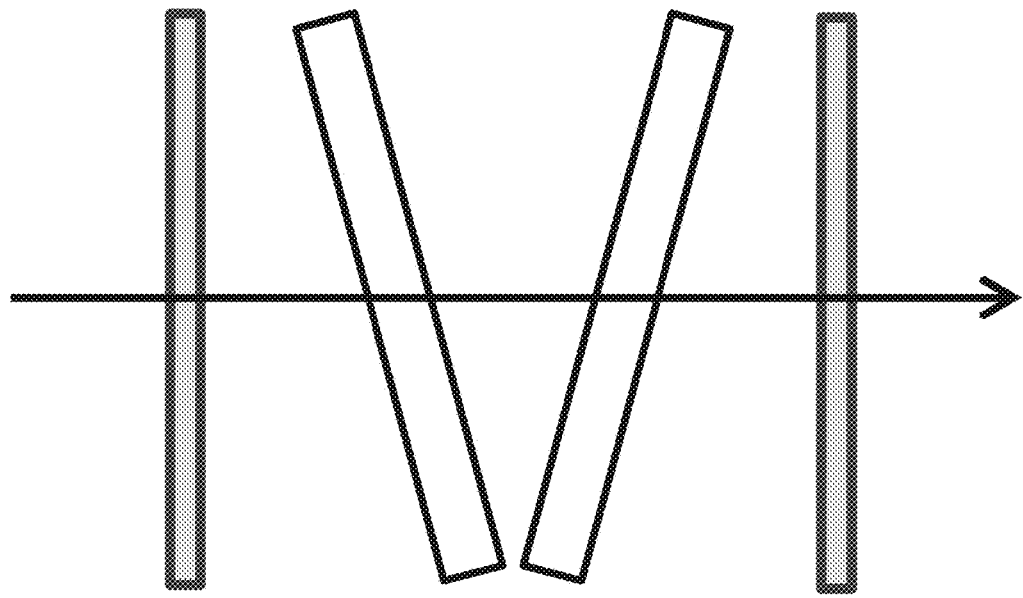
FIG. 11 shows an exemplary configuration of an optical device ("DichOS-6").
Figure 12:
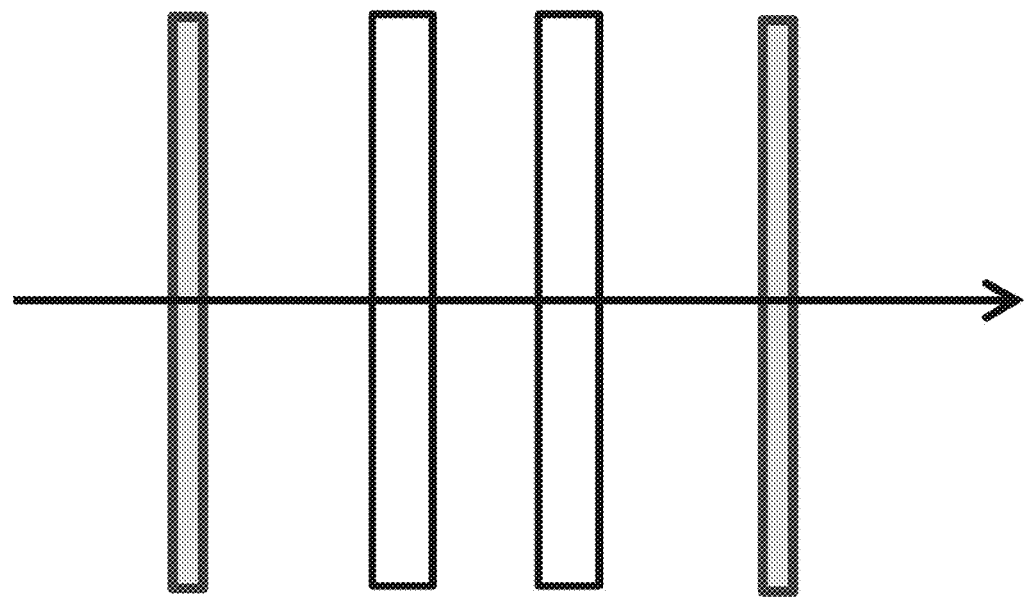
FIG. 12 shows the N-plates corrector device for DichOS-6 ("N-Corr-6").

For each variant of the DichOS device, an associated N-plates device may be defined, which consists of the same device with all tilted surfaces replaced by normal surfaces. As an example, for one DichOS variant (e.g. DichOS-6; see FIG. 11) which consists of two outer ¼ waveplates with isoplates in a V configuration between them (see infra), the associated N-plates corrector (which we refer to as 'NCorr-6') simply has two normal isoplates between the outer waveplates (see FIG. 12).

The correction method using an N-plates device comprises, but is not limited only to, the following steps:

Record a spectrum with the DichOS device.

Replace the DichOS device with its associated N-plates corrector.

Record a second spectrum for the N-plates corrector, which contains only the beam error contributions.

Subtract the second spectrum from the first to remove the beam errors.

The implementation of this method would involve either supplying the N-Corrector as a matched device with the DichOS standard, or in certain embodiments, building a slide mechanism into the DichOS device enabling the tilted plates to be switched with normal plates. In another embodiment, the plate tilt angles would be continuously adjusted against two stops. Whichever approach is used, it is important that good angular orientation (around all three axes) is maintained between the two measurements.

Exemplary DichOS Variants

Nine DichOS variants which have been investigated are specified in the Table shown in FIG. 13.

The numbering system is roughly in order of increasing complexity, with the simplest device being referred to as 'DichOS-1' etc. For each variant, the angle of the tilted isoplate surface(s) $\theta_{IP}$ was set so that all variants had approximately the same spectrum magnitude (~700 mdeg at 585 nm), thus ensuring a fair comparison. All of the DichOS variants have CD spectra similar to that shown in FIG. 14 (which is actually the DichOS-6 spectrum).

It may be assumed that the axial rotation (i.e. around Z) of each DichOS variant does not create a new configuration. Also the crystal axis angles may be interchanged in each device (45°→−45°, −45°→45°) with the only effect being an inversion of the resulting CD spectrum. Again this interchange is not assumed to create new configurations since the resulting change in spectrum characteristic is trivial.

Beam Error Sensitivity Comparison

To assess the performance of each DichOS variant with respect to beam error sensitivity, the percentage error was computed for horizontal and vertical beam deviations of 2° (assumed to be an upper limit for most instruments), and for symmetric (3°, 3°) and asymmetric beam divergences (3°, 5°). In the case of divergences, the degree values represent half angles and a rectangular beam shape (in angle space) is assumed. The (3°, 5°) divergence is deemed to be the upper limit likely to be found on commercial instruments. N-plates correction data has only been computed to date for DichOS-6. The results are shown in the Table in FIG. 44.

Examination of the results in the Table in FIG. 44 reveals the following:

Divergence errors are somewhat less critical than was implied in earlier experiments. The reason for this is that horizontal and vertical ray angle deviations produce oppositely signed CD errors, so that for a symmetrically divergent beam, a large degree of error cancellation occurs even before correction is applied. For asymmetric divergence (where the divergence is greater in one direction than the other), the error is related to the difference in divergences rather than to the aggregate in horizontal and vertical directions.

Analysis of the N-plates correction method (with DichOS-6) has shown that it corrects horizontal beam deviations at 72.4%, and vertical beam deviations at 93.6%. This asymmetry of correction renders it less effective than the 'rotate & average' method, although the asymmetry can be an advantage where beam divergence is greater in the vertical direction than the horizontal, as can be seen in the DichOS-6 results. However this advantage comes at the cost of poorer correction for horizontal beam angle errors.

The 'rotate & average' correction method appears to be very effective for all of the DichOS variants studied.

DichOS-1 and DichOS-2 are of interest mainly due to their great simplicity, but are unlikely to provide suitable reference standards due to excess beam sensitivity and poor restoration of the polarization state. DichOS-3 suffers from beam sensitivity and unrestored polarization. In DichOS-4 and DichOS-5, only one of these two deficits is fixed. Hence the configuration which is preferred as a reference standard is DichOS-6.

It appears that variants 4, 6, 7, 8 and 9 have the same residual errors after rotate & average correction. DichOS-4 is excluded because, as mentioned above it does not restore the polarization state. DichOS-7, while appearing good after correction, has very large errors prior to correction. This renders it subject to increased error residuals and the requirement for critically precise orientation when making the two measurements. Close inspection shows that DichOS-7 is in fact similar in performance to DichOS-3, but with errors balanced in the X and Y directions. The increase in complexity is therefore not reflected in improved performance.

DichOS-8 and DichOS-9 are the two self-correcting configurations. Of these two, DichOS-9 may be preferable since the correction is balanced for horizontal and vertical deviations. Conditions which would favor DichOS-8 are where the beam angle or beam divergence is known to be greater in the vertical direction than horizontal, since DichOS-8 corrects vertical errors more effectively.

In exemplary embodiments, the preferred embodiment is DichOS-6 with 'rotate & average' or '3-angle' correction, since this provides the best correction with minimal complexity. DichOS-9 represents another preferred embodiment, providing a corrected spectrum with only one measurement rather than two or three. However one property which is not revealed in the table above is that DichOS-9, while being well corrected at the peak positions, is less well corrected than DichOS-6 at intermediate wavelengths. This can be understood by realizing that the central ½ waveplate only provides true polarization rotation at peak positions (where the polarization state after passing the front ¼ waveplate is linear). If a 'rotate & average' correction is applied to DichOS-9, it is found that the errors at off-peak wavelengths clean up and the end result is similar to DichOS-6. But in this case nothing is gained over DichOS-6 at the cost of a considerable increase in device complexity.

3-Angle Correction

The 3-angle correction algorithms improve on the 'rotate & average' (R&A) method to correct for beam angle and beam divergence errors affecting the DichOS device. Three versions of this algorithm (A, B and C) are described herein below. Versions A and B do not work perfectly at all wavelengths but do have the virtue of being quite simple. Version C is derived from a theoretical model of the DichOS signal for non-normal beam incidence, and thus works correctly for all wavelengths. It is, however, somewhat more complicated than versions A and B.

Figure 14A:
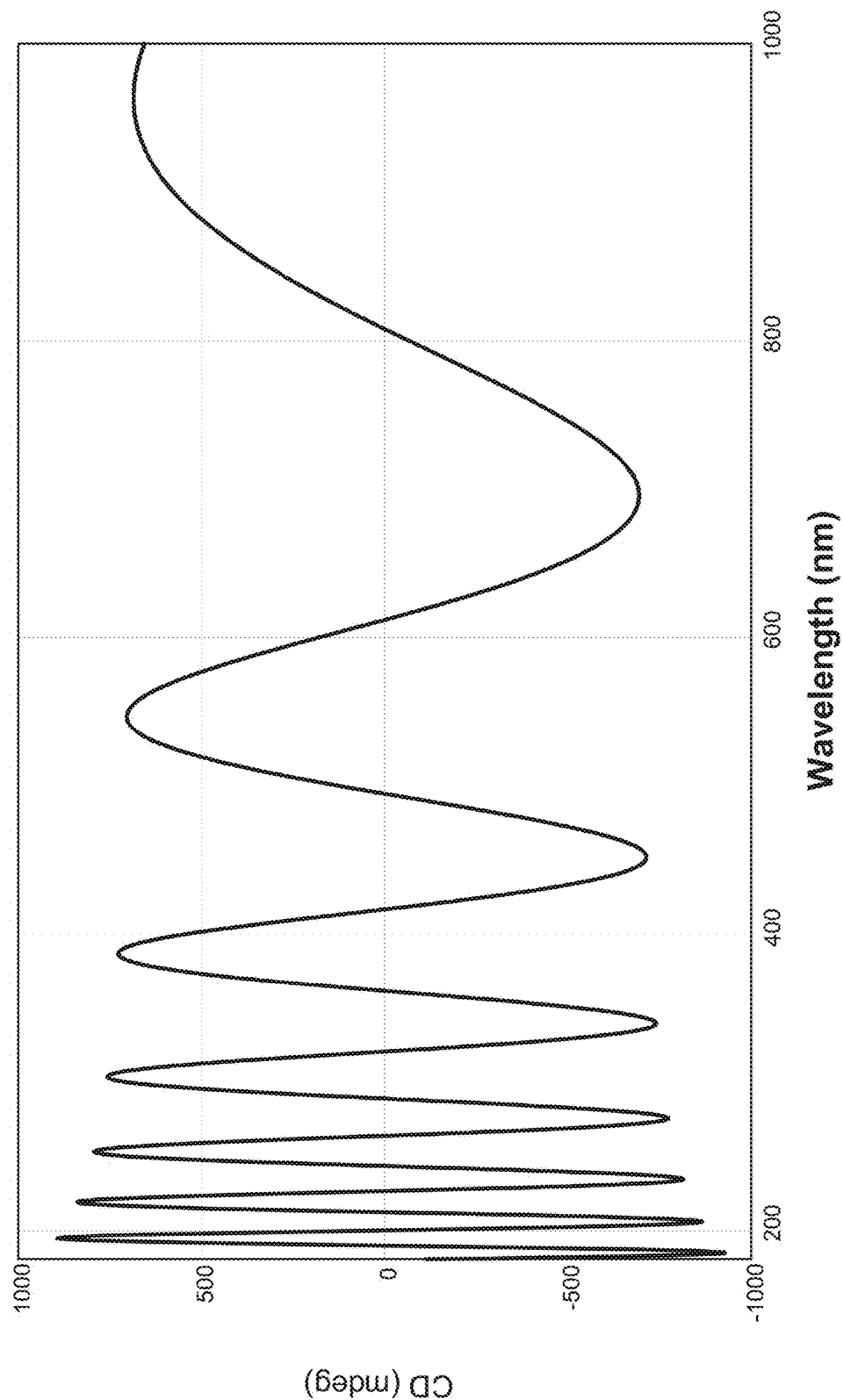
FIG. 14(a) is a graph that shows the DichOS nominal CD spectrum for one preferred embodiment (with $MgF_2$ waveplates).
Figure 14B:
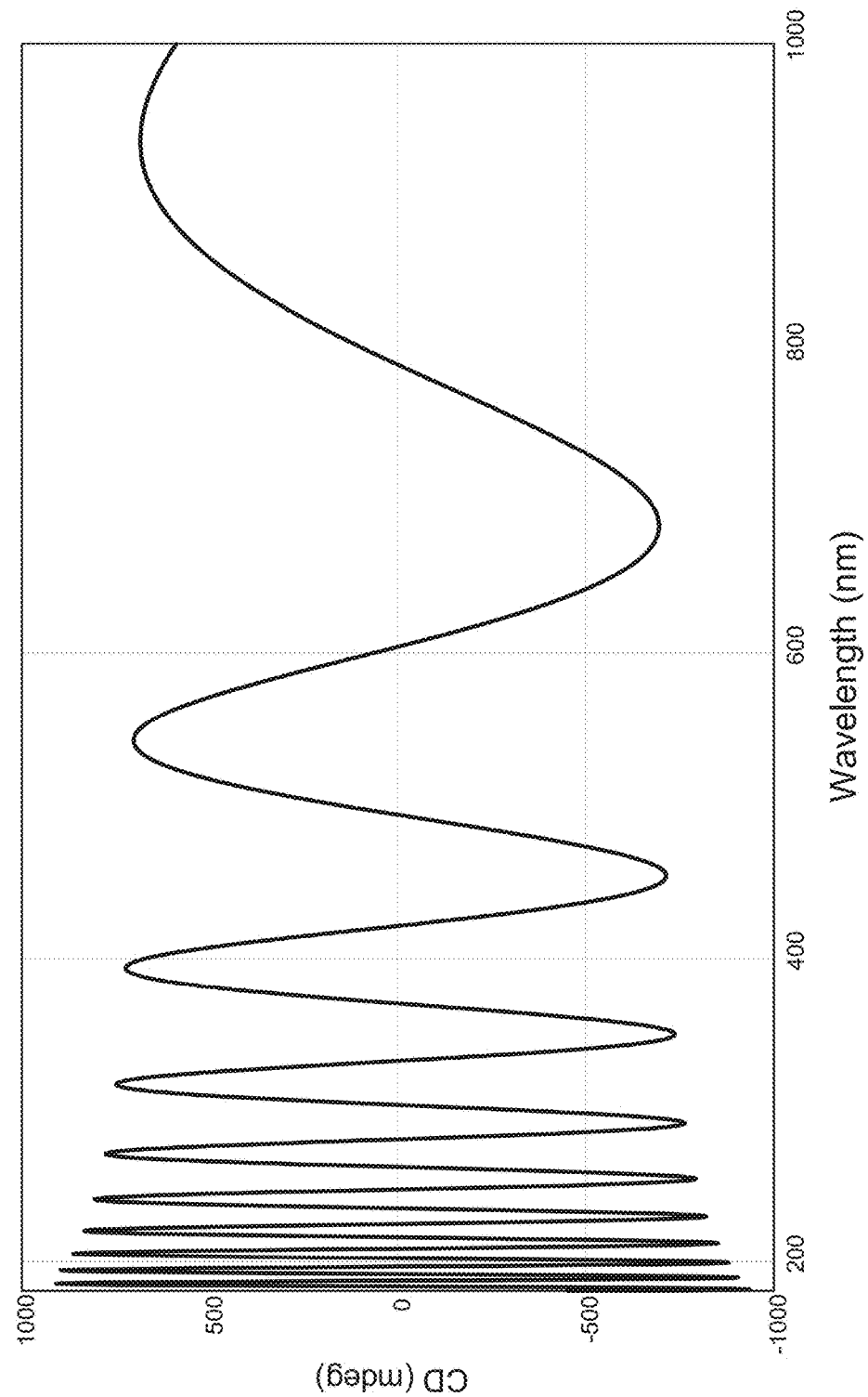
FIG. 14(b) is a graph that shows the DichOS nominal CD spectrum for another preferred embodiment (with quartz waveplates).

The example plots which are referred to below are derived for two preferred embodiments of the DichOS-6 device, the first of which has following specification (which is the proposed production specification for DichOS):

$\theta_I$=20° Isoplates tilt angle
$t_{WP}$=0.1037 mm waveplates thickness
$\theta_C$=−45° crystal axis angle of first waveplate
Waveplates material: magnesium fluoride
Isoplates material: fused silica The second preferred embodiment referred to below has the following specification:

$\theta_I$=20° Isoplates tilt angle
$t_{WP}$=0.1328 mm waveplates thickness
$\theta_C$=−45° crystal axis angle of first waveplate
Waveplates material: crystalline quartz
Isoplates material: fused silica The nominal CD spectra for these device specifications are shown in FIG. 14.

CD Measurements

It is assumed that three DichOS CD spectra are measured with the device axially rotated by 0°, 45° and 90° respectively. These three spectra are referred to as $CD_0$, $CD_{45}$ and $CD_{90}$ (wavelength dependence is assumed).

Rotate & Average Correction

For each wavelength point in the spectrum, the simple 'rotate & average' corrected spectrum is computed as follows:

$$CD_{R\&A} = \frac{CD_0 + CD_{90}}{2} \quad (12)$$

Figure 15A:
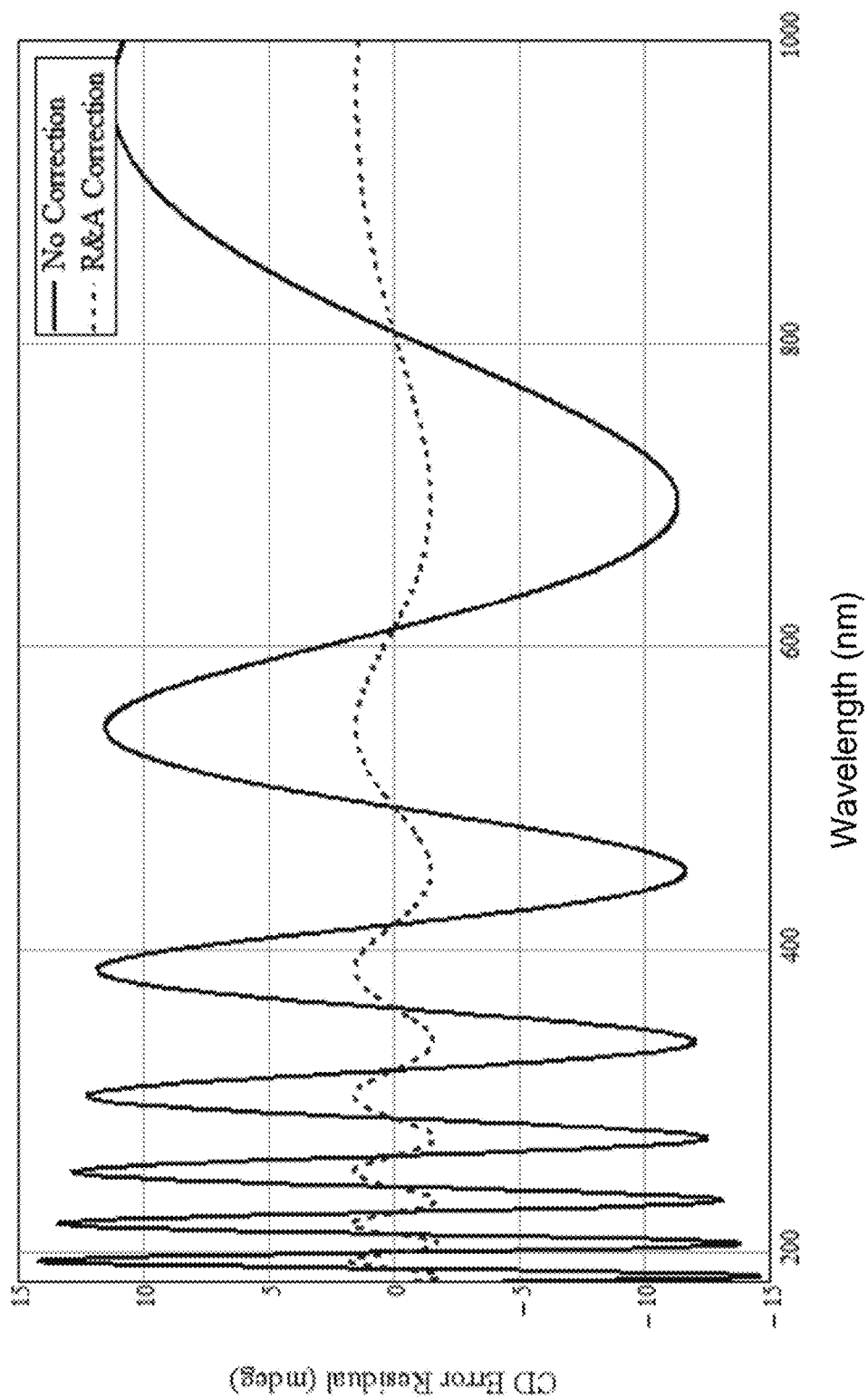
FIG. 15(a) is a graph that shows reduction in CD error with R&A Correction (2° beam angle error) for one preferred embodiment (with $MgF_2$ waveplates).
Figure 15B:
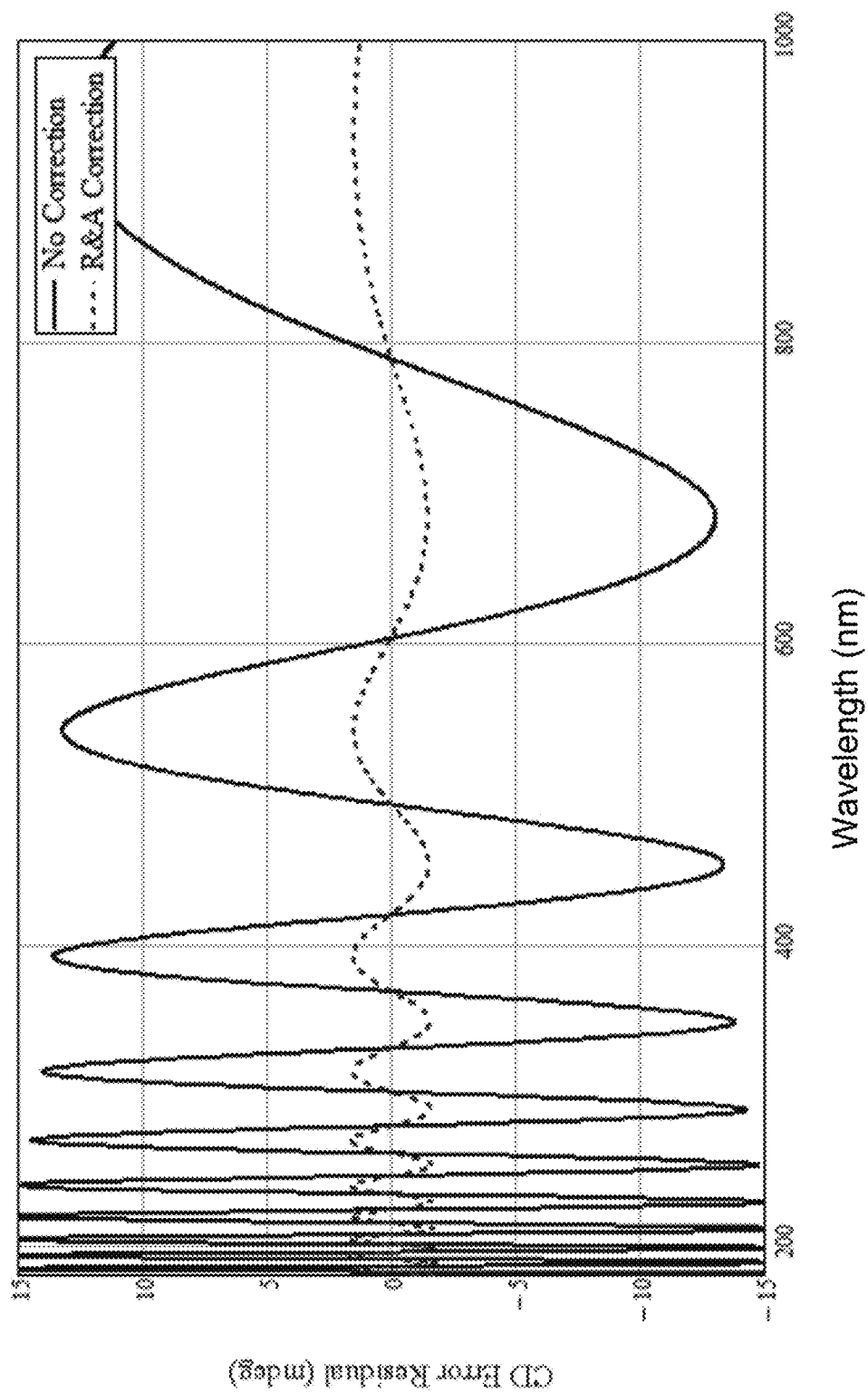
FIG. 15(b) is a graph that shows reduction in CD error with R&A Correction (2° beam angle error) for another preferred embodiment (with quartz waveplates).

This correction quite considerably reduces the errors due to beam angle error and beam divergence. In FIG. 15, the reduction in CD error residual is shown for a 2° incident beam angle in the horizontal plane. In relative terms, this corresponds to an error reduction from 1.85% to 0.21% across the entire wavelength range.

The Axial Rotation Signal

If the DichOS device is rotated axially around the Z axis (i.e. around the axis of light propagation through the device), a small sinusoidal signal will be observed with period 180° superimposed upon a larger DC signal. This AC signal contains information which allows the error residual in the rotate & average signal ($CD_{R\&A}$) to be reduced.

The amplitude of the axial rotation signal is given by:

$$A = \sqrt{\frac{CD_0^2}{2} + \frac{CD_{90}^2}{2} + CD_{45}(CD_{45} - CD_0 - CD_{90})} \quad (13)$$

While the phase of the axial rotation signal is given by:

$$\varepsilon = \frac{1}{2} \cdot \tan^{-1}\left(\frac{CD_0 + CD_{90} - 2CD_{45}}{CD_0 - CD_{90}}\right) \quad (14)$$

It is noted that the 3-angle correction algorithms as presently described do not make use of the phase angle $\varepsilon$.

3-Angle Correction: Version A

The first '3-angle corrected' CD value ($CD_{3A}$) is given by:

$$CD_{3A} = CD_{R\&A} - A \cdot C_{plate} \cdot \text{sgn}(CD_{R\&A}) \quad (15)$$

Where:

sgn is the signum function returning the sign of the argument (−1, 0 or +1).

$C_{plate}$ is a constant which is specific to the tilt angle of the isotropic plates and the material comprising the isoplates and waveplates. In the case of 20° fused silica isoplates and quartz waveplates, it has the value $C_{plate}$=0.1275. In the case of 20° fused silica isoplates and magnesium fluoride waveplates, it has the value $C_{plate}$=0.1480. The value of this constant may be computed for any plate angle $\theta_{IP}$ and choice of materials for the waveplates and isoplates.

Figure 16A:
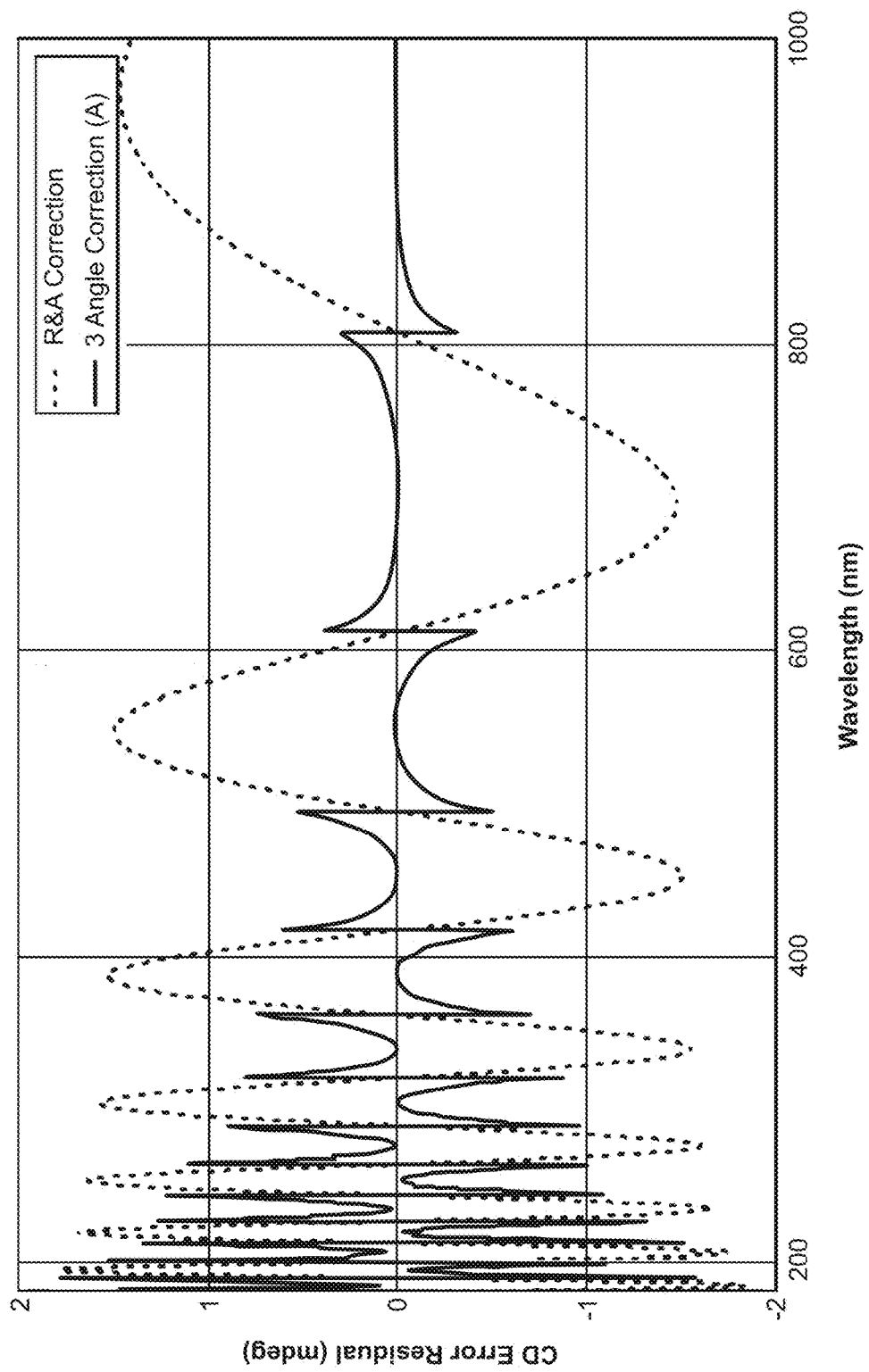
FIG. 16(a) is a graph that shows the reduction in CD Error with 3-angle Correction Version A (2° beam angle error) for one preferred embodiment (with $MgF_2$ waveplates).

The effect of this algorithm in reducing the CD error residual of the R&A spectrum for the two preferred embodiments can be seen in FIG. 16. The correction for beam angle errors is very good at the peak positions, although there is a degree of overcorrection towards the UV end of the spectrum.

3-Angle Correction: Version B

The second '3-angle corrected' CD value ($CD_{3B}$) is given by:

$$CD_{3B} = \frac{CD_{R\&A}}{1 + A \cdot K_{plate}} \quad (16)$$

Where:

$K_{plate}$ is another constant specific to the tilt angle $\theta_{IP}$ of the isotropic plates and choice of materials for the isoplates and waveplates. In the case of 20° fused silica isoplates and quartz waveplates, it has the value $K_{plate}$=1.823518×10$^{-4}$. In the case of 20° fused silica isoplates and magnesium fluoride waveplates, it has the value $K_{plate}$=2.122×10$^{-4}$. The value of this constant may be computed for any isoplate angle and material comprising the isoplates and waveplates.

Figure 17A:
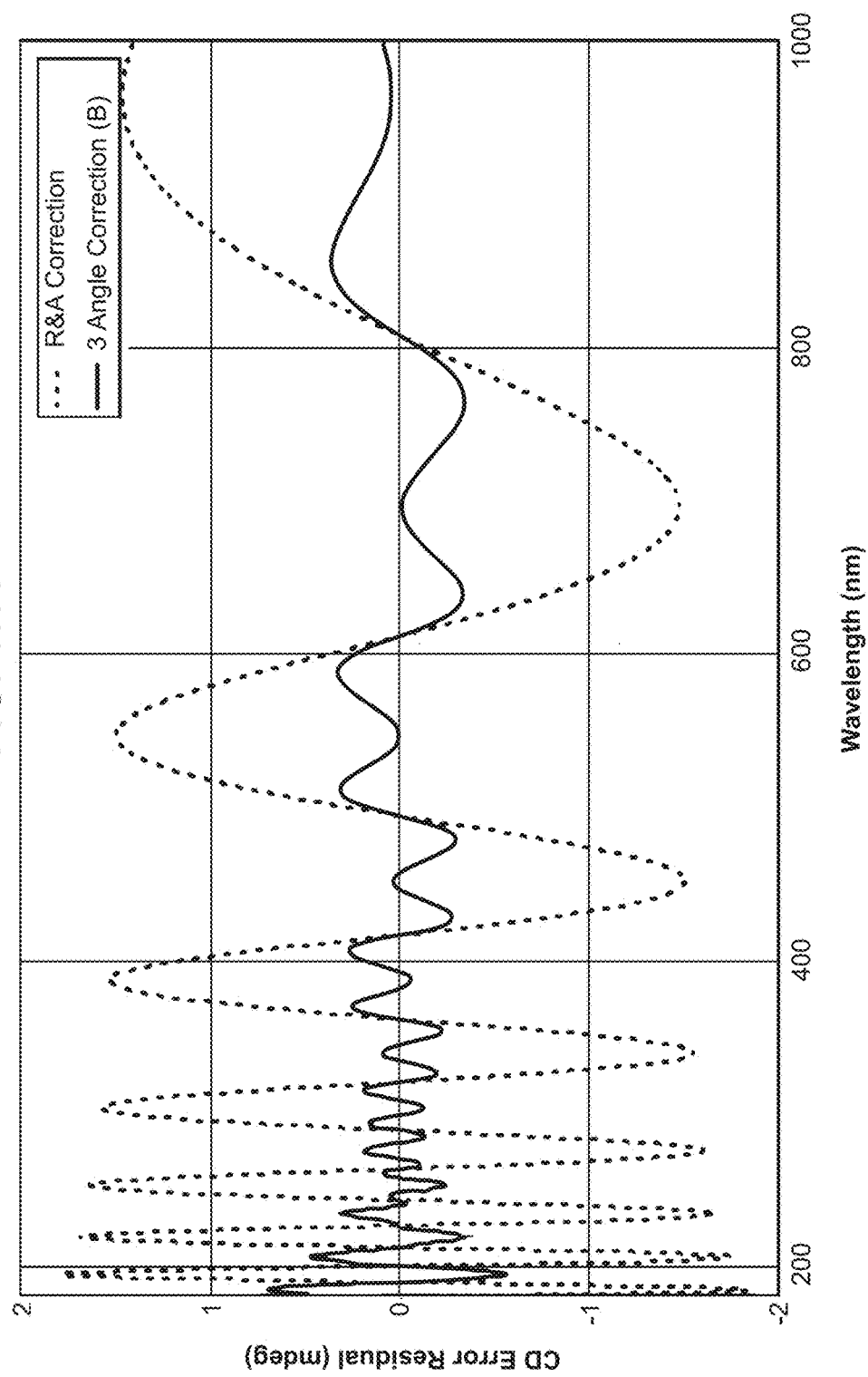
FIG. 17(a) is a graph that shows the reduction in CD Error with 3-angle Correction Version B (2° beam angle error) for one preferred embodiment (with $MgF_2$ waveplates).
Figure 17B:
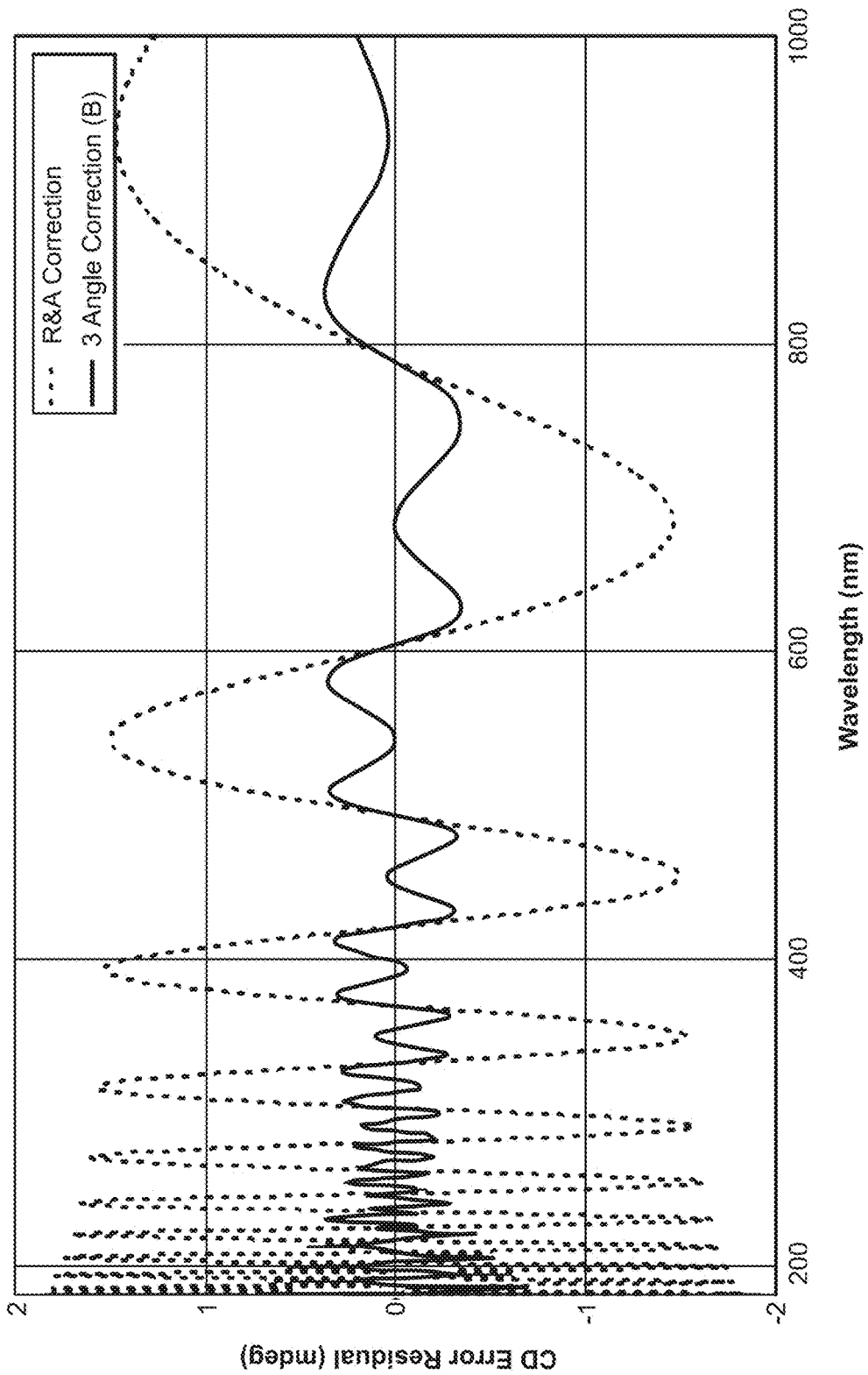
FIG. 17(b) is a graph that shows the reduction in CD Error with 3-angle Correction Version B (2° beam angle error) for another preferred embodiment (with quartz waveplates).

As can be seen in FIG. 17, this version of the algorithm has good correction at both the peak positions and the zero crossings for both of the preferred embodiments. The overcorrection at the UV end of the spectrum is somewhat worse than for version A, and at the intermediate wavelengths (between the peaks and zeroes) the error residual is undercorrected. This version of the algorithm does not suffer from discontinuities seen in version A.

3-Angle Correction: Version C

Assuming:

$n(\lambda)$ is the refractive index of the isoplates material
$n_{WP}(\lambda)$ is the mean refractive index of the waveplate material $(n_e+n_o)/2$ $$K = -\frac{180 \times 10^3}{2\pi}$$

is a conversion factor to render results in millidegrees $$\Phi = \frac{2\pi \cdot B(\lambda) \cdot t_{wp}}{\lambda}$$

is the waveplate retardation in radians
$B(\lambda)$ is the waveplate birefringence ($n_e-n_o$)

We define the function L0($\lambda$), giving the LD signal for a single isotropic plate inclined at angle $\theta_{IP}$:

$$L0(\lambda) = \frac{-2 \cdot K \cdot (n(\lambda)^2 - 1)^2 \cdot (\sin(\theta_{IP})^2)}{(n(\lambda)^2 + 1) \cdot (2 \cdot n(\lambda)^2 \cdot \sin(\theta_{IP})^2 - 4 \cdot n(\lambda)^2 + 2 \cdot \sin(\theta_{IP})^2)} \quad (17)$$

We then define the function $L1(\lambda)$, being the first derivative of $L0(\lambda)$ with respect to $\theta_{IP}$:

$$L1(\lambda) = \frac{8 \cdot K \cdot n(\lambda)^2 \cdot \sin(2 \cdot \theta_{IP}) \cdot (n(\lambda)^2 - 1)^2}{(n(\lambda)^2 + 1) \cdot [2 \cdot \sin(\theta_{IP})^2 - 3 \cdot n(\lambda)^2 + n(\lambda)^2 \cdot (2 \cdot \sin(\theta_{IP})^2 - 1)]^2} \quad (18)$$

We next define the function $L2(\lambda)$, being the second derivative of $L0(\lambda)$ with respect to $\theta_{IP}$:

$$L2(\lambda) = \frac{8 \cdot K \cdot n(\lambda)^2 \cdot (n(\lambda)^2 - 1)^2 \cdot (8 \cdot n(\lambda)^2 \cdot \sin(\theta_{IP})^4 + 4 \cdot n(\lambda)^2 \cdot \sin(\theta_{IP})^2 - (8 \cdot n(\lambda)^2 + 8 \cdot \sin(\theta_{IP})^4 - 12 \cdot \sin(\theta_{IP})^2)}{(n(\lambda)^2 + 1) \cdot [2 \cdot \sin(\theta_{IP})^2 - 3 \cdot n(\lambda)^2 + n(\lambda)^2 \cdot (2 \cdot \sin(\theta_{IP})^2 - 1)]^3} \quad (19)$$

Then we define the function $L_{WP}(\lambda)$, the LD signal produced at a single waveplate interface for a small incident angle $\theta_{IP}$, divided by $\Delta\theta_{IP}^2$:

$$L_{wp}(\lambda) = \frac{(n_{wp}(\lambda) - 1)^2}{2 n_{wp}(\lambda)^2} \cdot K \quad (20)$$

We may now define the 'Amplitude to Residual Conversion' function: $ARC(\lambda)$:

$$ARC(\lambda) = \frac{-\left(\frac{L2(\lambda)}{2} + \frac{L1(\lambda)}{2 \cdot \tan(\theta_{IP})} - \frac{2 \cdot L0(\lambda)}{\tan(\theta_{IP})^2}\right) \cdot \sin(2\theta_C) \cdot \sin(\Phi(\lambda))}{\sqrt{\sin(2\theta_C)^2 \cdot \sin(\Phi(\lambda))^2 \cdot \left(\frac{L2(\lambda)}{2} - \frac{L1(\lambda)}{2 \cdot \tan(\theta_{IP})} + \frac{2 \cdot L0(\lambda)}{\tan(\theta_{IP})^2} + 2L_{wp}(\lambda)\right)^2 + \frac{\cos(\Phi(\lambda))^2 \cdot \Phi(\lambda)^2 \cdot L0(\lambda)^2}{n_{wp}(\lambda)^4}}} \quad (21)$$

Figure 18B:
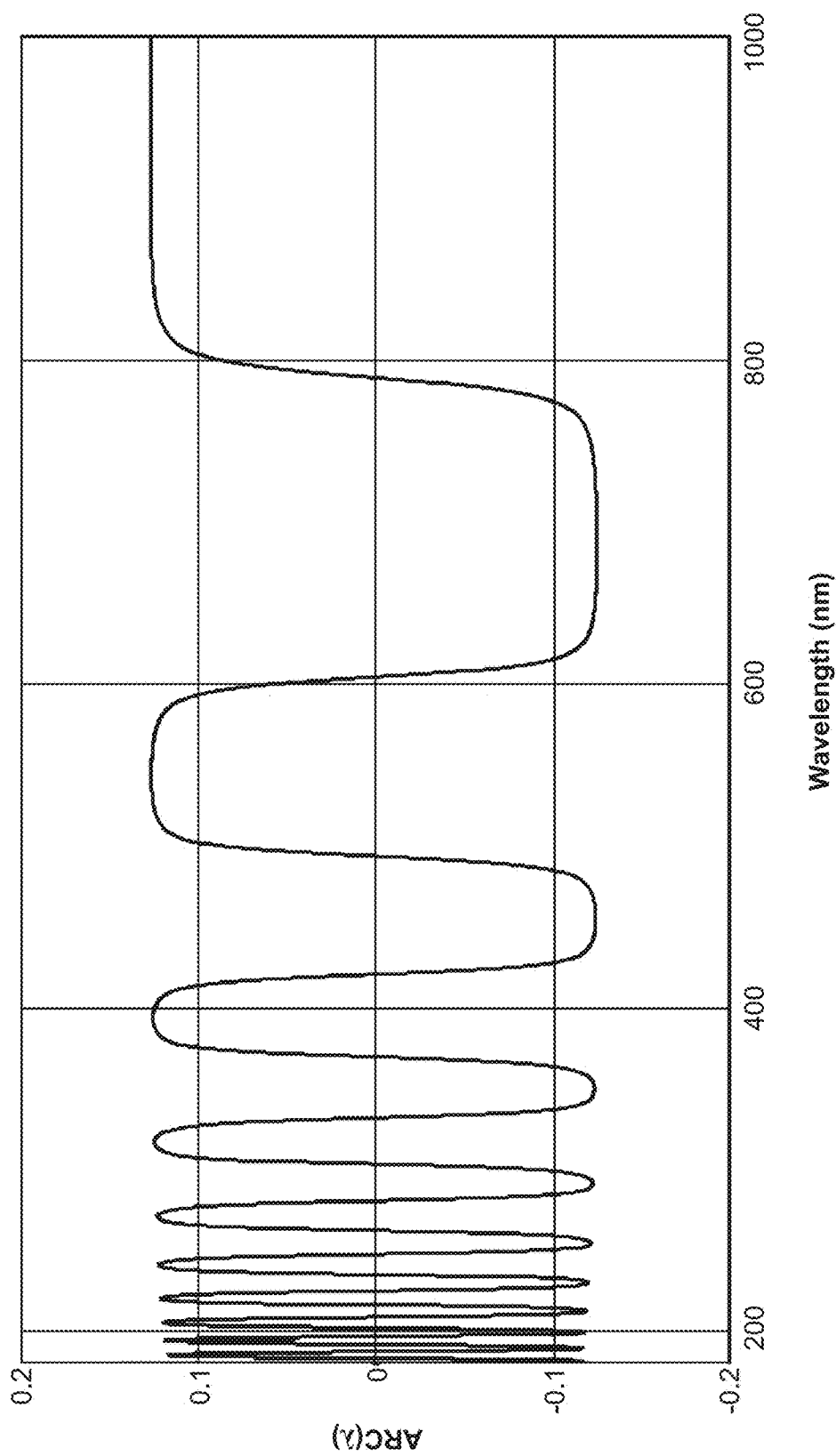
FIG. 18(b) is a graph that shows the Amplitude to Residual Conversion Function (ARC) for another preferred embodiment of the DichOS device (with quartz waveplates).

This function converts the measured axial rotation signal amplitude (A) into a CD error residual (when multiplied by A). $ARC(\lambda)$ is plotted in FIG. 18 for the two preferred embodiments specified supra. This is a fixed function of wavelength for any given DichOS specification. It may be observed that the value of $ARC(\lambda)$ in the plateau regions is close to the values of $C_{plate}$ defined for version A of the algorithm (see above).

Having defined the $ARC(\lambda)$ function, we may now define the third '3-angle corrected' CD value ($CD_{3C}$) as follows:

$$CD_{3C} = CD_{R\&A} - A \cdot ARC(\lambda) \quad (22)$$

This is similar to version A of the algorithm but with a wavelength dependent factor instead of a fixed factor multiplying A to give the residual correction term (which is then subtracted from $CD_{R\&A}$). The $ARC(\lambda)$ function automatically switches sign to match the peak being corrected, avoiding the need for a signum function. It also reduces in magnitude towards the UV end of the spectrum, avoiding the overcorrection problem seen with version A of the algorithm.

In FIG. 19, the effect of 3-angle correction version C can be seen for a 2° incident beam angle error, for each of the two preferred embodiments specified supra. It is clear that the error has been reduced effectively to zero for all wavelengths and there are no discontinuities in the final error residual.

Conclusion

Three versions (A, B and C) of the '3-angle correction' algorithm have been described supra. These algorithms are designed to remove the residual CD error which remains after performing a rotate & average (R&A) correction on the DichOS CD spectrum.

Versions A and B of the algorithm are simple but do not correct perfectly at all wavelengths.

Version C completely corrects for beam angle errors at all wavelengths. It requires computation of the $ARC(\lambda)$ function which is dependent on the design parameters of the DichOS-6 device. The $ARC(\lambda)$ function in practice could either be calculated live or stored in a table for each wavelength point between, for example, 160 nm and 2000 nm with an interval of 0.1 nm.

The 3-angle algorithms described also correct for beam divergence errors, although not to the same degree as beam angle errors. The manner in which beam divergence errors are reduced by the 3-angle correction algorithms is as follows:

For an asymmetric beam divergence, the error is reduced to that corresponding to the smallest divergence with respect to azimuth. For example, if the incident beam has a 3° divergence (half-angle) in the horizontal plane and a 5° divergence in the vertical plane, 3-angle correction will reduce this to the equivalent of a 3° divergence in both horizontal and vertical.

If the divergence is symmetrical or equal in two orthogonal azimuths, 3-angle correction will not reduce the residual error. For example if the beam has a divergence of 3° in both horizontal and vertical, the error remaining after 3-angle correction will be equal to that remaining after rotate & average correction.

The algorithms described supra have been thoroughly tested using simulation data generated from an optical model of the DichOS device.

Example 4—Detector Polarisation Bias Response

It is known that certain detectors (such as photomultipliers) have a polarisation dependent response characteristic. This is usually in the form of a bias for light which is linearly polarised along a particular axis and can be caused by the presence of angled structures within the device or an angled front window. If the front window is strained the response can be transformed into a bias relative to orthogonal elliptical states. Here, a linear bias response is assumed.

Jones Model of Polarisation Bias

A simple way to model the polarisation bias of a detector is to assume that there is a preferred axis along which the response is maximal, with a minimal response occurring along the orthogonal axis. If the mean response is taken to be unity and the differential response is given by $\Delta R = R_{MAX} - R_{min}$ then the detector's angle dependent behaviour can be expressed in Jones matrix form as follows:

$$M_{det} = R(\theta_p)^{-1} \begin{bmatrix} \sqrt{1 + \frac{\Delta R}{2}} & 0 \\ 0 & \sqrt{1 + \frac{\Delta R}{2}} \end{bmatrix} R(\theta_p) \quad (23)$$

Where $\theta_p$ is the orientation of the detector's preferred axis measured from the X axis (horizontal) and $R(\theta_p)$ is the standard basis rotation transformation matrix:

$$R(\theta_p) = \begin{bmatrix} \cos\theta_p & \sin\theta_p \\ -\sin\theta_p & \cos\theta_p \end{bmatrix} \quad (24)$$

Figure 20:
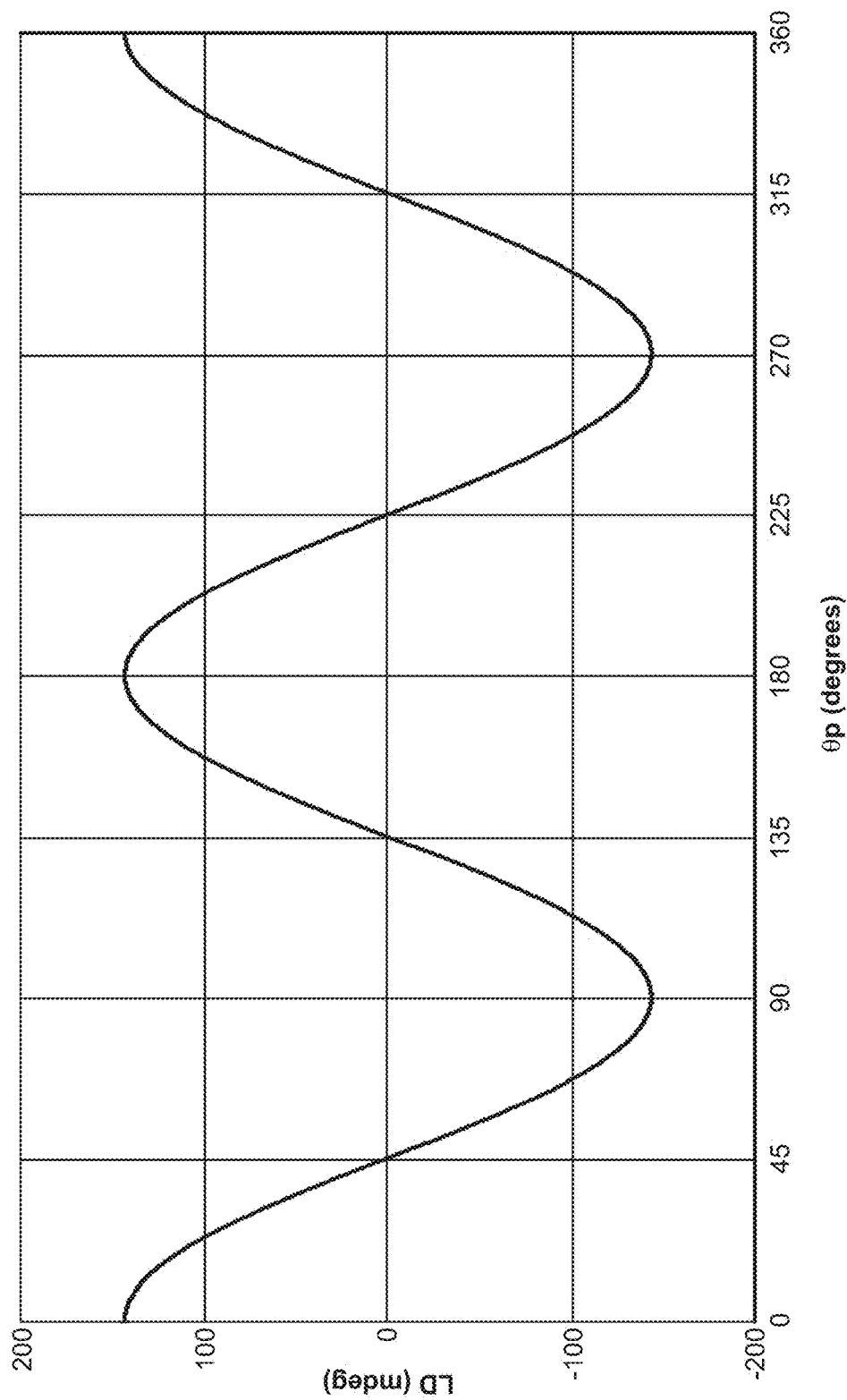
FIG. 20 is a graph that shows the LD signal of detector with 1% polarisation bias response as a function of detector rotation angle.

If the instrument is configured to measure LD ($\Delta A_{LD} = A_Y - A_X$), it can be shown that the measured response due to the detector bias $\Delta R$ (with no other sample present) in millidegrees is given by:

$$LD_{meas} = \Delta R \cdot \cos 2\theta_p \cdot \frac{K}{2} \quad (25)$$

where K is given by Equation (3). In FIG. 20, the effective LD signal generated by a detector with $\Delta R = 0.01 = 1\%$ polarisation bias is plotted as a function of detector angle $\theta_p$. The signal is maximal when the preferred direction is aligned along X (+ve signal) or Y (−ve signal). At diagonal angles (45°, 135° etc.) the effect of the detector bias is cancelled (which provides a clue as to why rotating a PMT detector is effective in minimizing CD baselines).

The peak magnitudes for 1% bias are just over 140 mdeg, showing that very little bias is required in the detector to produce quite a substantial LD signal. There are two cycles for a single rotation of the detector, which corresponds with the behaviour observed in practice.

Note that in CD mode the measurement is in theory insensitive to the detector bias, but optical imperfections (for example strain in the PMT front window) will have the effect of making the bias response partially visible as a CD artefact.

Measurement of PMT Polarisation Bias

Figure 21:
FIG. 21 is a graph that shows the measured polarisation bias response of a CD PMT detector.

An approximate measurement of the bias response was conducted on a PMT detector. This was performed using the DichOS-6 device with the second waveplate removed. Measurements were taken at the peak positions with the detector rotated to give maximal response. The result is of the measurement is shown in FIG. 21. The bias is wavelength dependent and rises to around 0.6% at 600 nm. As discussed supra, this would produce a significant LD spectrum if the PMT angle was not optimized or other methods applied to reduce the effect. It has since been discovered that 'rotate & average' correction is highly effective in removing the artefacts caused by PMT polarisation bias.

Example 5—Tolerance and Temperature Sensitivity Analysis

The following example details the results of a tolerance and temperature sensitivity analysis applied to the DichOS-6 device in one preferred embodiment specified below.

The design parameter values for this specification are as follows:
$\theta_{IP}$=20° Isoplates tilt angle (or half V-angle)
$t_{WP}$=0.1328 mm Waveplate thickness
$\theta_{WP}$=45° Orientation of waveplate crystal axis
Isoplate material: fused silica
Waveplate material: crystalline quartz Very similar results were obtained from a tolerance analysis performed on the preferred embodiment specified below (which the proposed production specification for the device). A separate temperature sensitivity analysis was performed for this embodiment.

$\theta_{IP}$=20° Isoplates tilt angle (or half V-angle)
$t_{WP}$=0.1037 mm Waveplate thickness
$\theta_{WP}$=45° Orientation of waveplate crystal axis
Isoplate material: fused silica
Waveplate material: magnesium fluoride An initial tolerance sensitivity analysis was performed and demonstrated that it is desirable to keep the isoplates angle $\theta_{IP}$ as large as possible (without exceeding the dynamic range of the CD instrument) since this tends to minimize the CD errors.

Having determined appropriate tolerances for the various construction and material parameters, a series of Monte-Carlo simulations were run to verify that devices, assembled to the to the specified tolerances, would fall within the required performance criteria (as defined herein below).

Additionally, those device parameters having a temperature-dependence were also analysed separately to confirm that the device would remain within specification over an acceptable range of operational temperatures (as defined herein below).

Performance Criteria

The DichOS device, assembled according to a defined set of material and construction tolerances, preferably must meet the following performance criteria, where the accuracy figures are relative to the nominal (i.e. calculated) CD spectrum for the device:
Operational wavelength range: 170 nm to 1700 nm
CD Signal Accuracy (%) ±1% at all wavelengths
Wavelength accuracy (of peak or zero crossing): ±0.05 nm at 180 nm
±1.0 nm at 1000 nm
Nominal operational temperature: 20° C.
Allowable range of temperature variation: ±10° C.

According to preferred exemplary embodiments, the device must remain within specification over the temperature range given above. The notation $\Delta CD$ % will be used to represent the relative CD signal accuracy in percent, and is defined as follows:

$$\Delta CD\% = \frac{\Delta CD}{CD} \times 100 \quad (26)$$

Coordinate System and Parameter Definitions

Figure 22:
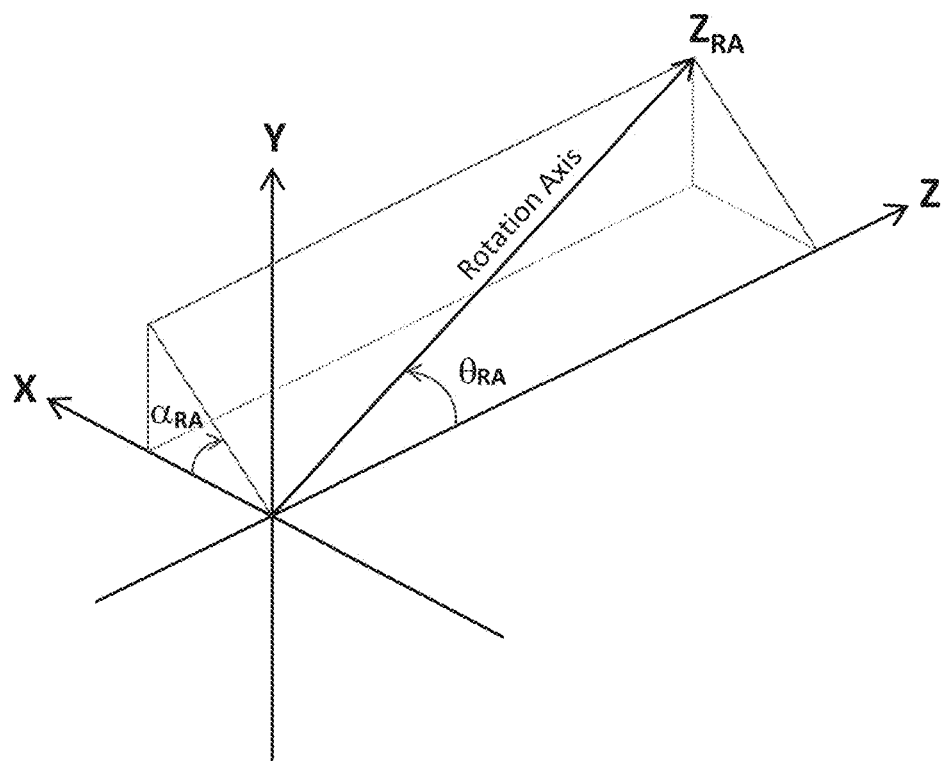
FIG. 22 is a schematic showing the DichOS optical frame and rotation axis.

A right handed coordinate system (XYZ) is defined according to the present invention, and referred to as the 'DichOS Optical Frame' (see FIG. 22). All of the angular orientation parameters of the DichOS optical elements are defined with reference to this frame (and hence to each other). The Z axis is the axis of light propagation through the device.

Further defined is an axis $Z_{RA}$ relative to the optical frame, representing the rotation axis of the DichOS device (as used for 'rotate & average' and '3-angle' correction methods, as described supra). The rotation axis is defined by an azimuth angle $\alpha_{RA}$ and a deviation angle $\theta_{RA}$, as shown in FIG. 22. Nominally the rotation axis is coincident with the Z axis of the optical frame (i.e. $\theta_{RA}$=0°).

A full list of the DichOS construction parameters are given in Table 6, below, including the material property parameters (isoplate refractive index $n(\lambda)$ and waveplate birefringence $B(\lambda)$). $\alpha_{RA}$ may take on any value between 0° and 360° and therefore a tolerance for this parameter is not determined, hence its exclusion from the Table.

TABLE 6

| Element | Parameter Symbol | Parameter Description | Nominal Value |
|---|---|---|---|
| Waveplate 1 | $\theta_{WP1\_X}$ | Waveplate 1 tilt about X | 0° |
|  | $\theta_{WP1\_Y}$ | Waveplate 1 tilt about Y | 0° |
|  | $\theta_{WP1\_Z}$ | Waveplate 1 tilt about Z | 45° ($\theta_{WP}$) |
|  | $\theta_{WP1\_C}$ | Waveplate 1 C-axis error | 0° |
|  | $t_{WP1}$ | Waveplate 1 thickness | 132.8 μm ($t_{WP}$) |
|  |  |  | 103.7 μm ($t_{WP}$) |
| Waveplate 2 | $\theta_{WP2\_X}$ | Waveplate 2 tilt about X | 0° |
|  | $\theta_{WP2\_Y}$ | Waveplate 2 tilt about Y | 0° |
|  | $\theta_{WP2\_Z}$ | Waveplate 2 tilt about Z | −45° (−$\theta_{WP}$) |
|  | $\theta_{WP2\_C}$ | Waveplate 2 C-axis error | 0° |
|  | $t_{WP2}$ | Waveplate 2 thickness | 132.8 μm ($t_{WP}$) |
|  |  |  | 103.7 μm ($t_{WP}$) |
| Isoplate1 | $\theta_{IP1\_X}$ | Isoplate 1 tilt about X | 0° |
|  | $\theta_{IP1\_Y}$ | Isoplate 1 tilt about Y | 20° ($\theta_{IP}$) |
| Isoplate2 | $\theta_{IP2\_X}$ | Isoplate 2 tilt about X | 0° |
|  | $\theta_{IP2\_Y}$ | Isoplate 2 tilt about Y | −20° (−$\theta_{IP}$) |
| RA | $\theta_{RA}$ | Rotation axis deviation from Z | 0° |
| Material | n(λ) | Isoplate refractive index | λ dependent |
|  | B(λ) | Waveplate birefringence | λ dependent |

Figure 23:
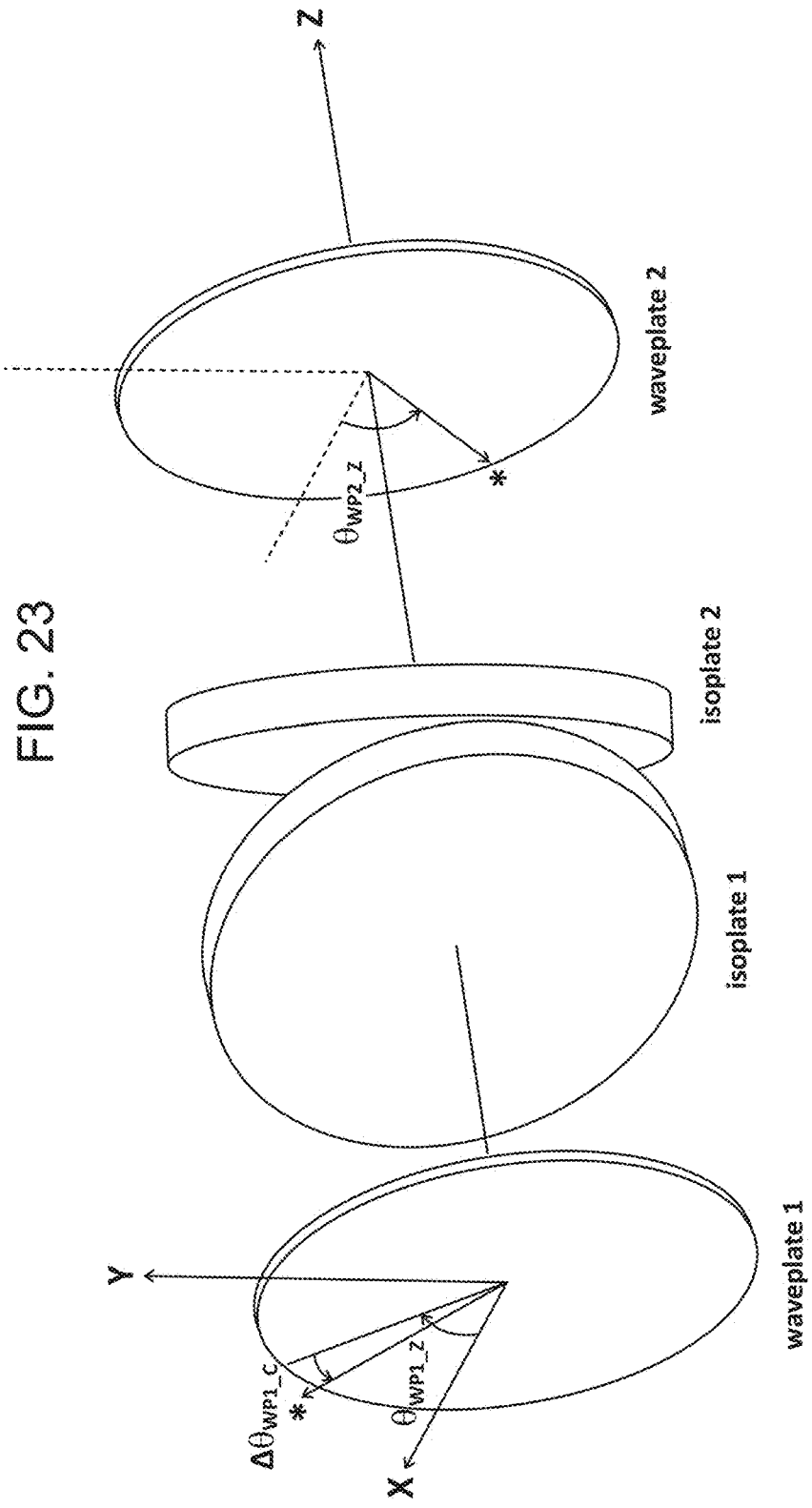
FIG. 23 shows DichOS elements oriented to the optical frame. Waveplate C-axes are indicated with an (*).
Figure 25:
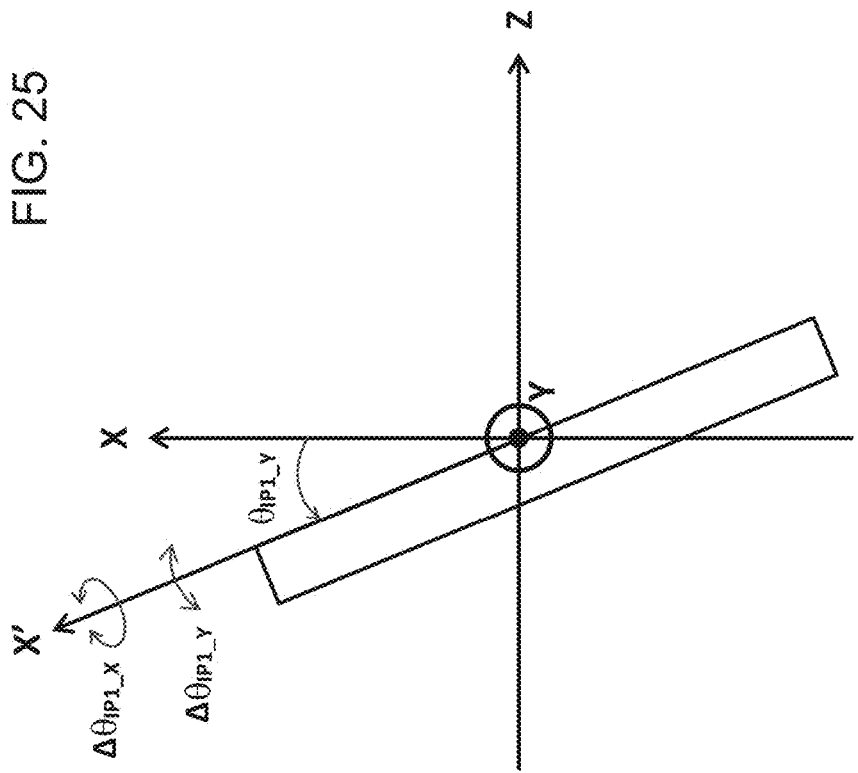
FIG. 25 shows isoplate tilt angle and angular deviations (1st isoplate).
Figure 24:
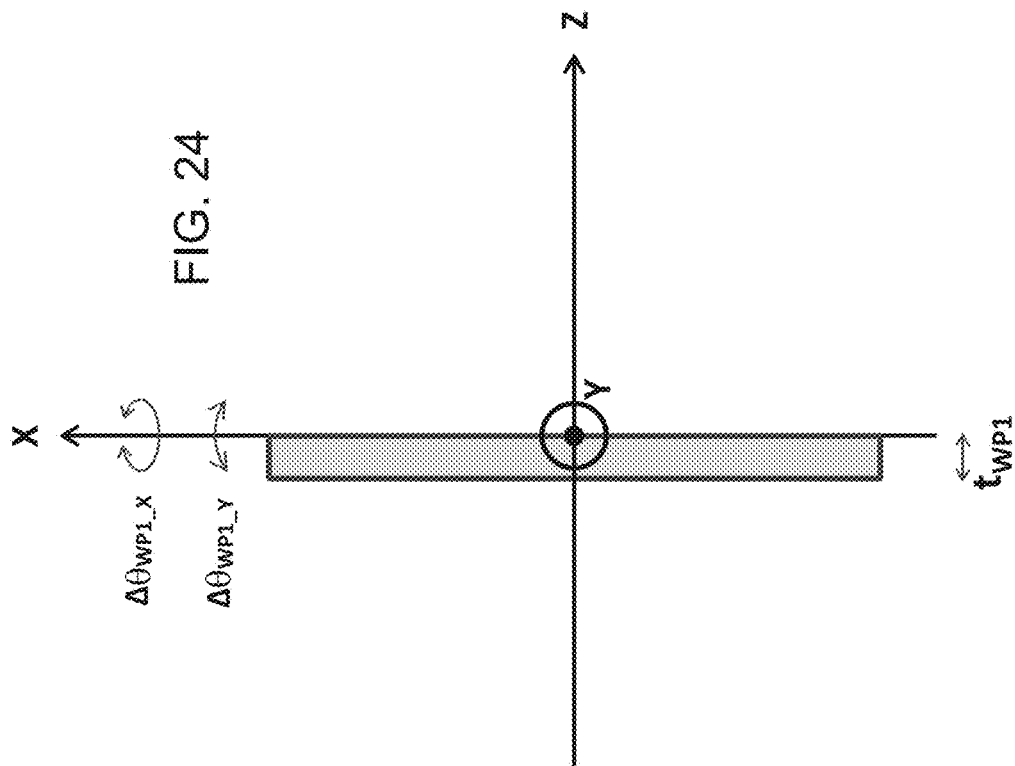
FIG. 24 shows waveplate thickness and angular deviations (1st waveplate).

The diagrams in FIGS. 23, 24 and 25 serve to further illustrate the definitions of the various angles and angle deviations. For the waveplates the angles refer to the orientation of the crystal axis (C-axis). In addition to the X, Y and Z deviations, the deviations of the C-axes out of the plane of the plates are defined ($\Delta\theta_{WP1\_C}$ and $\Delta\theta_{WP2\_C}$) which are manufacturing tolerances (of the waveplates) rather than construction tolerances. Since the waveplates are nominally oriented normal to the Z axis, the angular deviations (assumed to be small) may be treated as commutative for the purposes of the tolerance analysis. FIG. 24 illustrates the parameters for the first waveplate. Similar definitions apply to the second waveplate.

In the case of the isoplates, the Y deviations ($\Delta\theta_{IP1\_Y}$ and $\Delta\theta_{IP2\_Y}$) are defined as would be expected, but the X deviations ($\Delta\theta_{IP1\_X}$ and $\Delta\theta_{IP2\_X}$) are defined as being relative to the local (intrinsic) X axis, labelled X' (see FIG. 25). This error therefore represents the deviation of the plate surface away from vertical. Since there is no unique axis in the isoplates, we are not concerned with Z (i.e. axial) rotations, hence only two angular parameters are required for the tolerance analysis. FIG. 25 illustrates the parameters for the first isoplate. Similar definitions apply to the second isoplate.

Tolerance Determinations

In the following sections, tolerances are determined for each of the parameters listed in Table 6.

Isoplate Refractive Index Tolerance $\Delta n$ is defined as the departure of the true refractive index of the isoplate material from the model index. This may come about either as an error in the model, a batch variation in the material, or a combination of both. The effect of $\Delta n$ will be an error in CD magnitude. To calculate this error, we begin with the expression for the DichOS CD signal given in equation (2).

$$CD(\lambda) = \sin 2\theta_{WP} \cdot \sin \Phi(\lambda) \cdot LD_{plates}(\lambda) \qquad (27)$$

From which the percent relative error due to a change of refractive index $\Delta n$ is given by:

$$\Delta CD\% = \frac{\Delta CD}{CD} \times 100 = \frac{100}{CD} \frac{dCD}{dn} \cdot \Delta n \qquad (28)$$

Then noting that the first two terms in equation 27 have no dependence on n, we may write:

$$\Delta CD\% = \frac{100}{LD_{plates}} \frac{\partial LD_{plates}}{\partial n} \cdot \Delta n \qquad (29)$$

If this function is plotted over the full wavelength range with $\Delta n=1$, it varies between 200 and 300. Taking a midpoint value of 250, then:

$$\Delta CD\% = 250 \cdot \Delta n \qquad (30)$$

If the maximum $\Delta CD\%$ allowable due to refractive index error is specified to be ±0.05%, the above equation can be rearranged to arrive at a tolerance for n:

$$\Delta n = \pm \frac{0.05}{250} = \pm 2 \times 10^{-4} \qquad (31)$$

Figure 26:
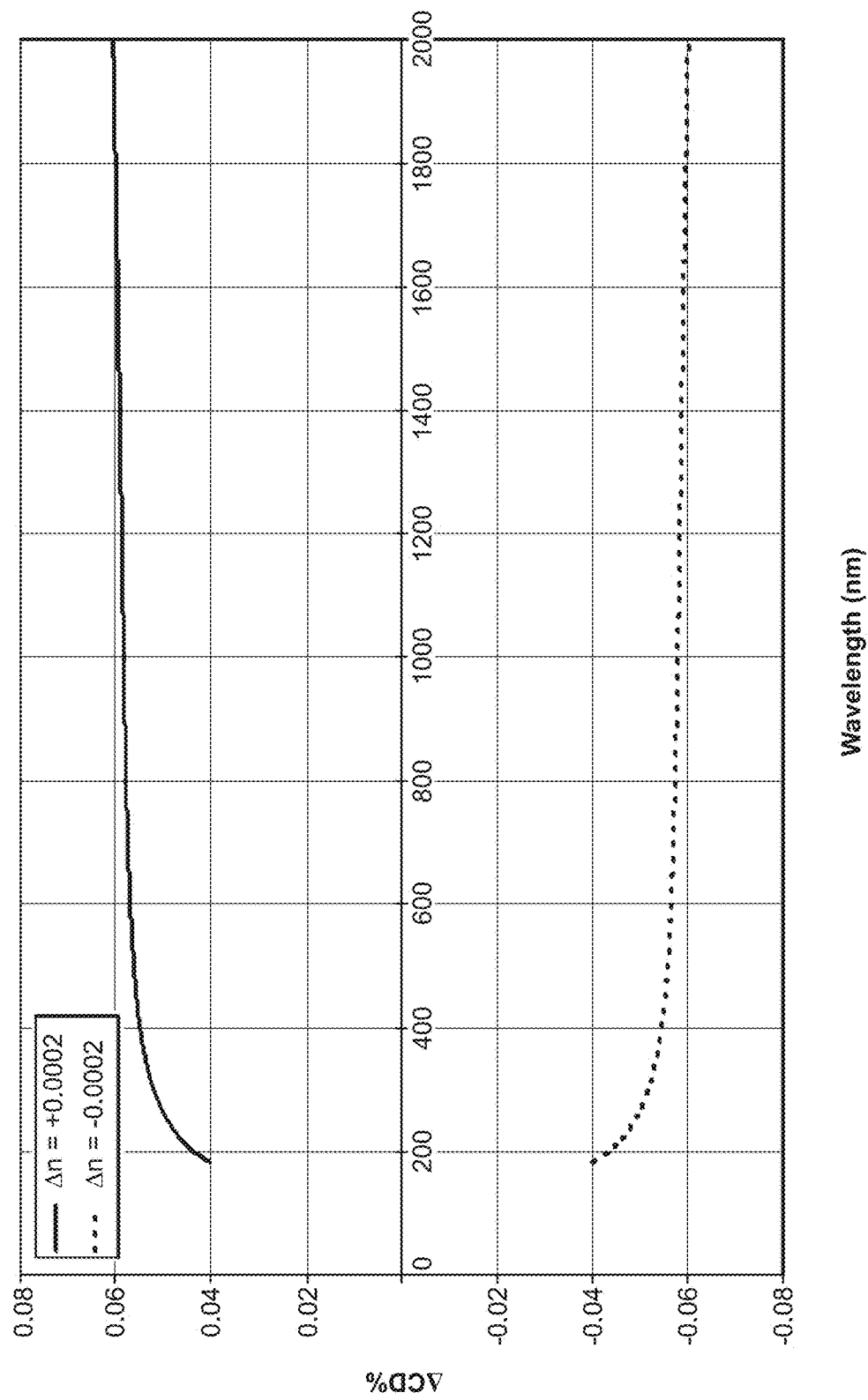
FIG. 26 is a graph that shows CD Error (%) due to a refractive index change in the isoplates of $\Delta n = \pm 0.0002$.

This corresponds to 2 parts in the fourth decimal place. Most silica glasses are specified with refractive index tolerances at least an order of magnitude tighter than this and with index homogeneity in the parts per million. It is unlikely, therefore, that refractive index errors in the isoplate material will have any significant impact on the accuracy of the DichOS device, provided a suitably pure grade of fused silica is chosen and the refractive index model matches the grade of silica used to construct the device. The CD error resulting from the above change in isoplate refractive index is shown in FIG. 26, where it can be seen that the effect is small at all wavelengths.

Waveplate Birefringence Tolerance

Figure 27A:
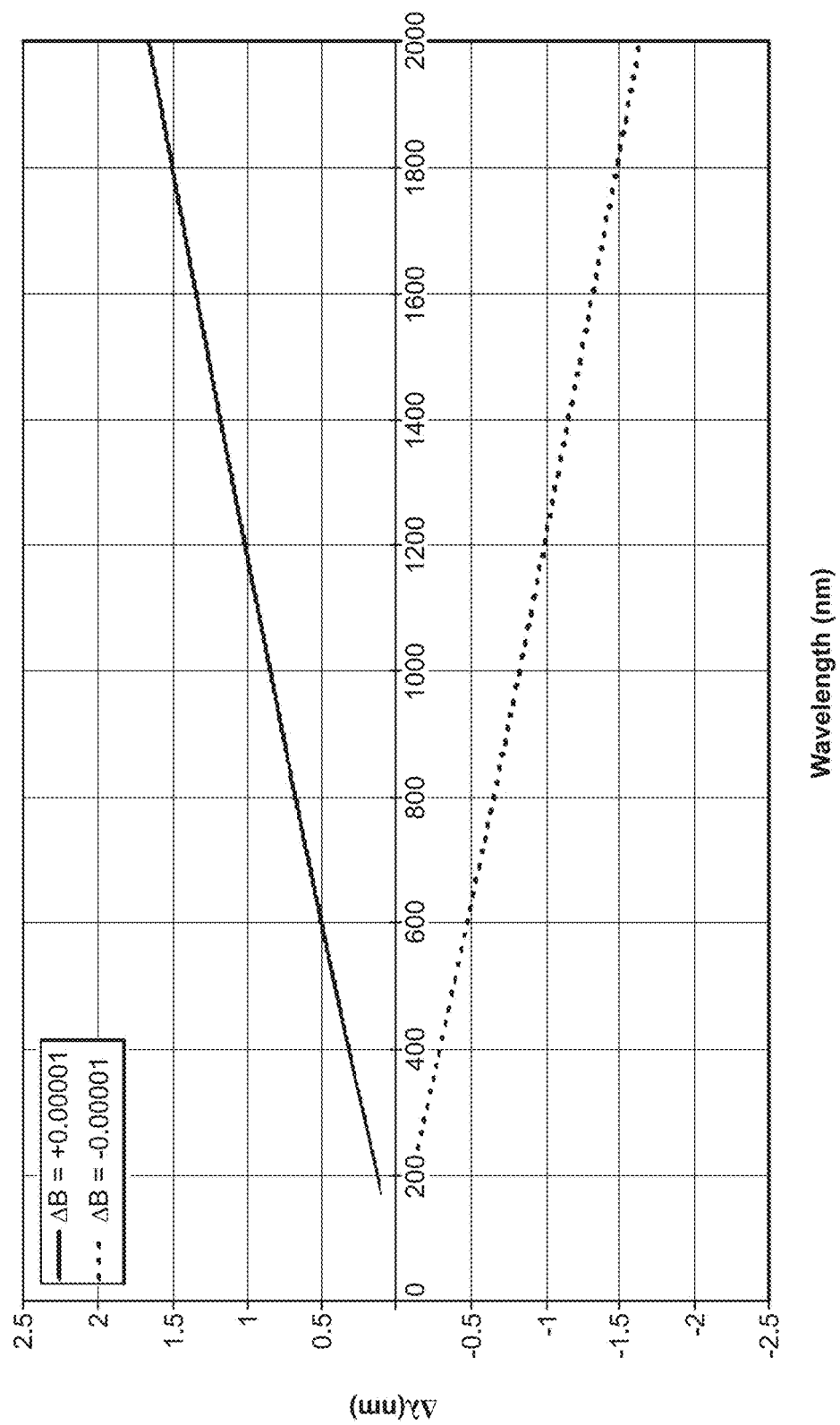
FIG. 27(a) is a graph that shows wavelength shift due to a birefringence error in the waveplates of $\Delta B = \pm 0.00001$ for one preferred embodiment (with $MgF_2$ waveplates).
Figure 27B:
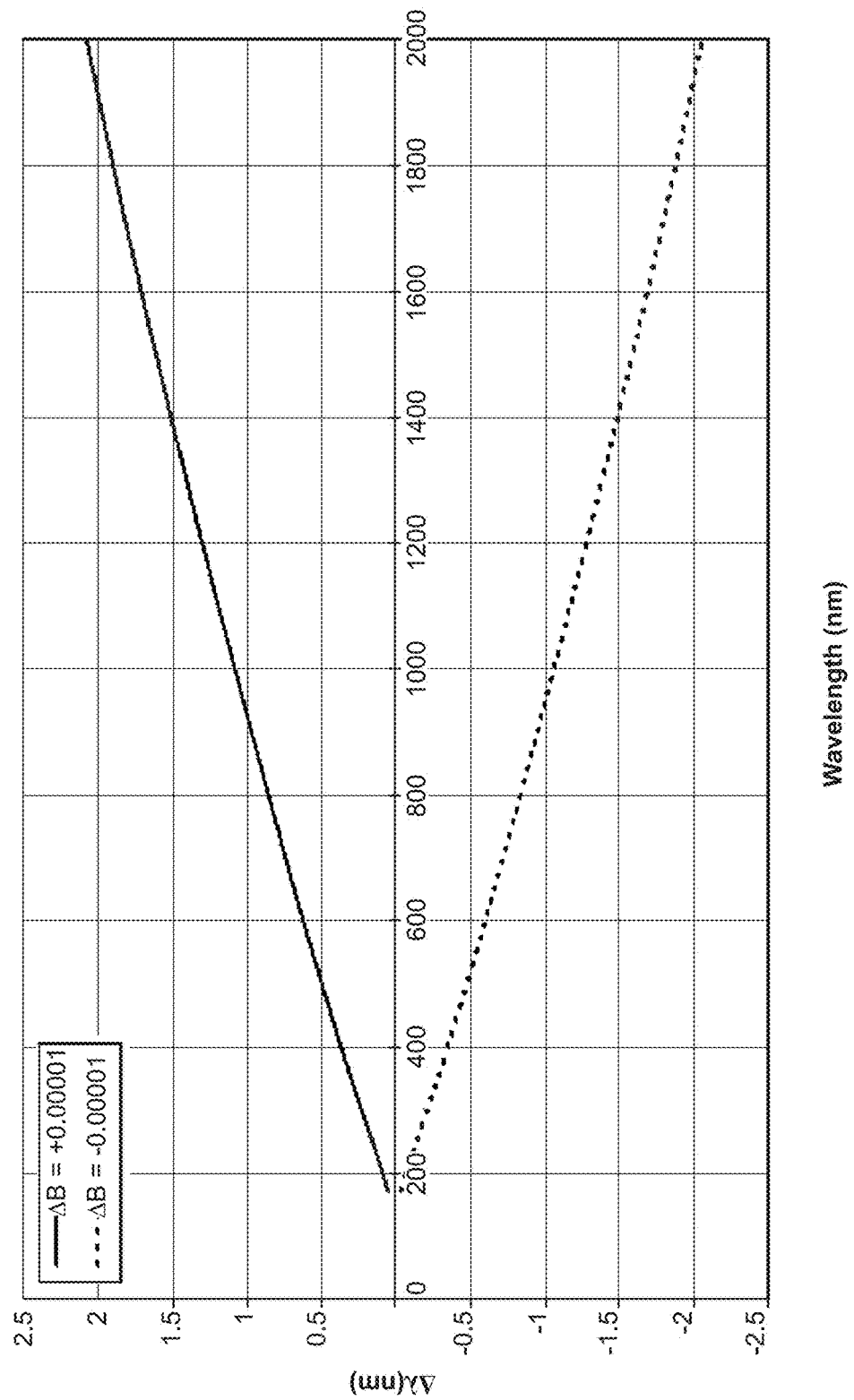
FIG. 27(b) is a graph that shows wavelength shift due to a birefringence error in the waveplates of $\Delta B = \pm 0.00001$ for another preferred embodiment (with quartz waveplates).

In the case of the waveplates, the concern is not with the individual refractive indices $n_o$ and $n_e$, but rather with the birefringence ($B = n_e - n_o$), since it is this which determines the phase retardation of the waveplate. FIG. 27 shows the wavelength shift due to birefringence error of $\Delta B = \pm 0.00001$ for the two preferred embodiments of the optical device specified supra, where (a) refers to the device incorporating $MgF_2$ waveplates and (b) refers the device incorporating quartz waveplates. The effect of an error $\Delta B$ in birefringence is to cause a shift in the position of spectral peaks or zero crossings. Like refractive index errors in the isoplates, $\Delta B$ encompasses effects due to both model errors and batch to batch material variations. Beginning with the expression for waveplate retardation:

$$\Phi = \frac{2\pi \cdot B(\lambda) \cdot t_{WP1}}{\lambda} \qquad (32)$$

It may be shown that:

$$\frac{\partial \lambda}{\partial B} = -\frac{\partial \Phi}{\partial B} \bigg/ \frac{\partial \Phi}{\partial \lambda} \qquad (33)$$

Hence:

$$\Delta \lambda = -\Delta B \cdot \frac{\partial \Phi}{\partial B} \bigg/ \frac{\partial \Phi}{\partial \lambda} \qquad (34)$$

Confining attention to the more critical VUV region, the above expression is evaluated approximately at 180 nm, resulting in:

$$\Delta \lambda = -\Delta B \cdot 5 \text{ μm} \qquad (35)$$

Given the performance criteria described supra, $\Delta \lambda$ is limited then to ±0.05 nm. Substituting this value in (35), and rearranging, a tolerance for B is calculated as:

$$\Delta B = \pm \frac{0.05 \text{nm}}{5 \mu \text{m}} = \pm 1 \times 10^{-5} \quad (36)$$

This corresponds to 1 part in the fifth decimal place, and is a somewhat tighter tolerance than that which was determined to the isoplates refractive index. The effect of this error on the wavelength shift may be seen in FIG. 27.

First Waveplate Thickness Tolerance

A thickness error $\Delta t_{WP1}$ in the first waveplate will give rise to a retardance error, leading again to a spectral shift. To calculate this shift, begin with the expression for retardance $\Phi$ given in equation (32). It may then be shown that:

$$\frac{d\lambda}{dt_{WP1}} = -\frac{d\Phi}{dt_{WP1}} \bigg/ \frac{d\Phi}{d\lambda} \quad (37)$$

And therefore the wavelength shift $\Delta \lambda$ resulting from thickness change $\Delta t_{WP1}$ is given by:

$$\Delta \lambda = -\Delta t_{WP1} \cdot \frac{d\Phi}{dt_{WP1}} \bigg/ \frac{d\Phi}{d\lambda} \quad (38)$$

At 180 nm, for a quartz waveplate with nominal thickness as defined in Table 6, equation (38) reduces approximately to:

$$\Delta \lambda = -\Delta t_{WP1} \cdot \frac{d\Phi}{dt_{WP1}} \bigg/ \frac{d\Phi}{d\lambda} \quad (39)$$

Inserting the value $\Delta \lambda = 0.05$ nm and solving for $\Delta t_{WP1}$:

$$\Delta t_{WP1} = \pm 88.25 \text{ nm} \quad (40)$$

Making a small adjustment upwards, the following figure is obtained for the tolerance on the waveplate thickness:

$$\Delta t_{WP1} = \pm 100 \text{ nm} = \pm 0.1 \text{ } \mu\text{m} \quad (41)$$

Given that the nominal thickness value for $\Delta t_{WP1}$ is 0.1328 mm, the tolerance above corresponds to 1 part in the $4^{th}$ decimal place (or least significant figure).

Figure 28A:
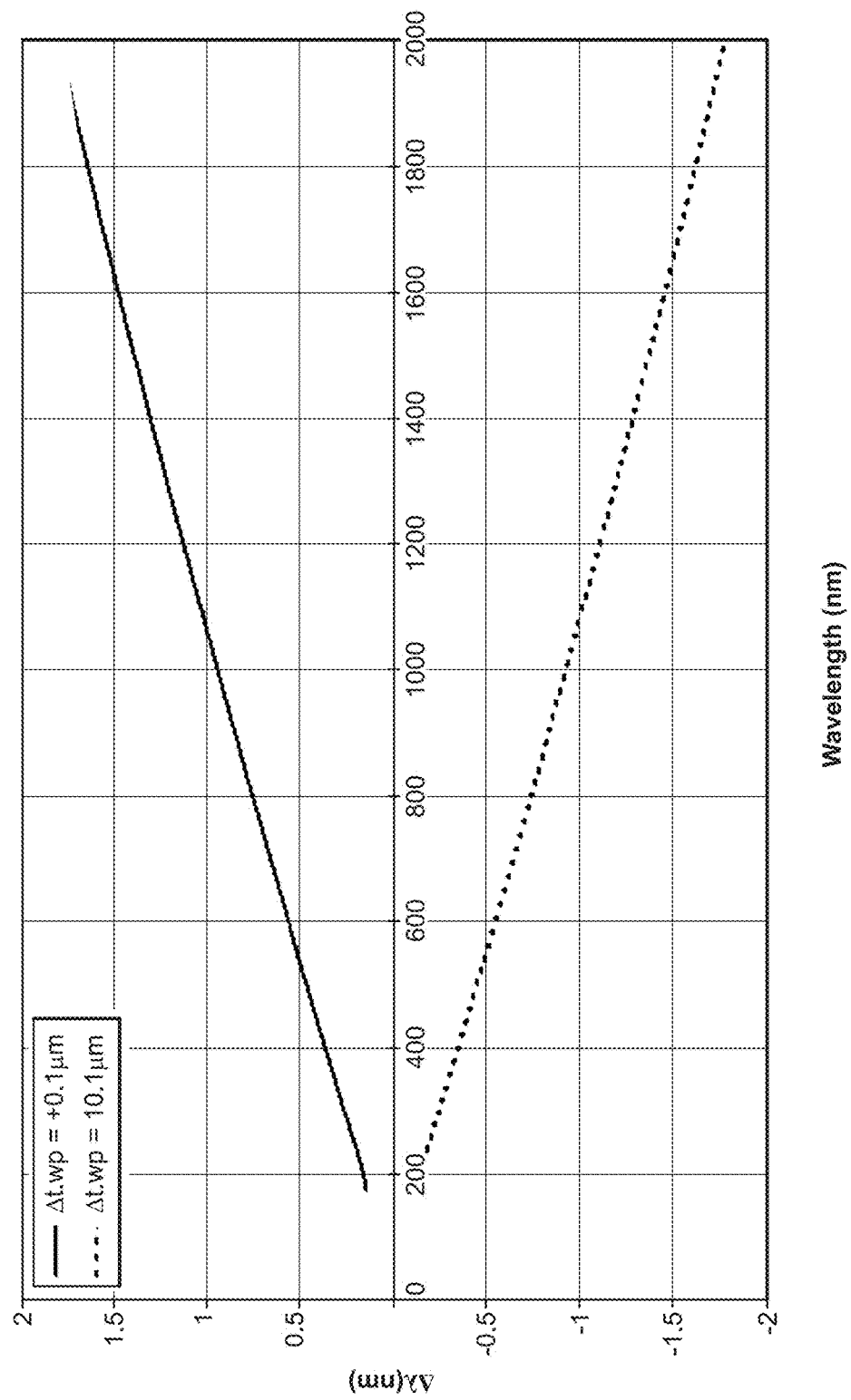
FIG. 28(a) is a graph that shows wavelength shift for a waveplate thickness change $\Delta t_{WP1} = \pm 0.1$ μm for one preferred embodiment (with $MgF_2$ waveplates).
Figure 28B:
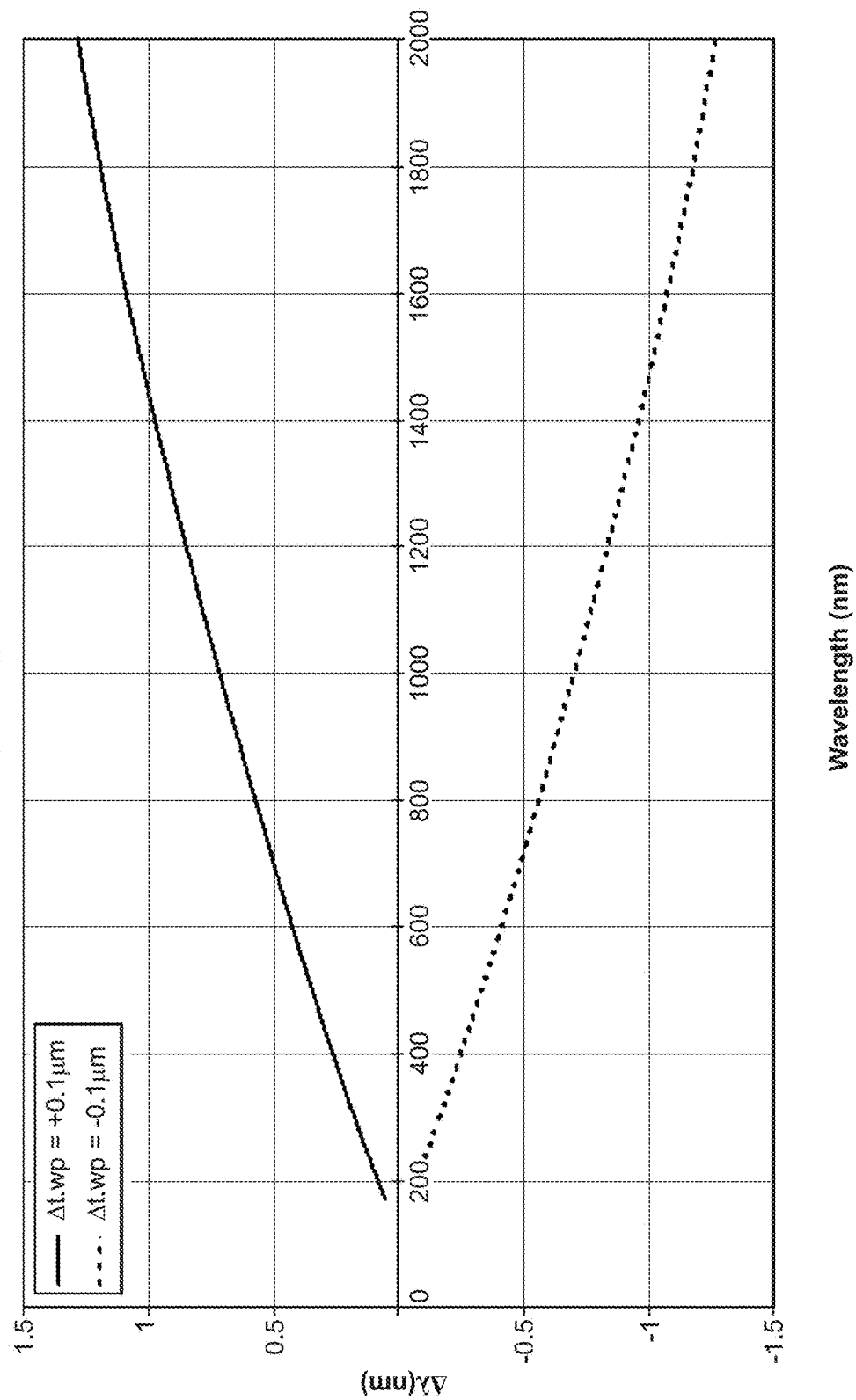
FIG. 28(b) is a graph that shows wavelength shift for a waveplate thickness change $\Delta t_{WP1} = \pm 0.1$ μm for another preferred embodiment (with quartz waveplates).

The graph in FIG. 28 shows the wavelength shift corresponding to the above thickness deviation across the whole wavelength range, for both preferred embodiments of the device specified supra., where (a) refers to the device incorporating $MgF_2$ waveplates and (b) refers the device incorporating quartz waveplates. FIG. 28 shows that the shift is greater the further we move towards the IR end of the spectrum, but the error remains well below the 1 nm shift at 1000 nm specified in the criteria described supra for both preferred embodiments. Furthermore, the corresponding CD magnitude change is well below 0.1% at 1000 nm.

Rotation Axis Tolerance

The maximum allowable deviation of the rotation axis $Z_{RA}$ from Z was determined as follows:

An optical model of the DichOS device was built incorporating 'rotate & average' and '3-angle correction' methods, in which the rotation axis was allowed to deviate from the Z axis by means of parameters $\alpha_{RA}$ and $\theta_{RA}$ (see FIG. 22). It is noted that all references to '3-angle Correction' in this report are intended to imply version C of the algorithm as described supra. The beam passing through the device was defined as being collimated (i.e. no divergence) but with a 2° incidence angle error. When the rotation axis was exactly collinear with the Z axis of the optical frame (i.e. $\theta_{RA} = 0°$), the $\Delta CD$ % errors were as follows:

No Correction: 1.85%
Rotate & Average Correction: 0.21%
3-angle Correction: 0%

It is evident that 3-angle correction completely corrects for beam angle errors in the absence of beam divergence.

Applying an arbitrary deviation $\theta_{RA}$ to the rotation axis, the azimuth $\alpha_{RA}$ was found which gave the worst case residual error after 3-angle correction. The value of $\theta_{RA}$ was then reduced until this error amounted to 0.05%. The limiting value for $\theta_{RA}$ then provided the tolerance for this parameter as follows:

$$\Delta \theta_{RA} = \pm 0.04° \quad (42)$$

The rationale behind this derivation is that, in order to justify the extra measurement required, 3-angle correction should provide a useful improvement over rotate & average correction. It was decided therefore that the residual error remaining after 3-angle correction should be no greater than 25% of that remaining after rotate & average correction, which corresponds to a $\Delta CD$ % value of 0.05% under the conditions described above.

Remaining Parameter Tolerances

Tolerances on the remaining parameters in Table 6 were derived as follows:

It was estimated that the total $\Delta CD$ % error due to refractive index and birefringence errors, plus the effects of temperature variations and the residuals remaining after 3-angle correction, could amount to up to approximately 0.5%. Detector polarisation bias can also contribute errors, but it has been found that the rotate & average correction method largely eliminates these effects.

In order to meet the required $\Delta CD$ % criterion of ±1%, it was decided that the outstanding 12 tolerances could contribute a maximum of 0.5% error in aggregate. If it is assumed that $\Delta CD$ % has a linear dependence on each parameter variation, this would imply an individual error contribution from each parameter of:

$$\frac{0.5\%}{\sqrt{12}} = 0.144\% \quad (43)$$

However it is known that many of the DichOS parameters have a square law dependence on $\Delta CD$ % rather than a linear dependence. To make allowance for this, the individual contribution value was revised downwards to 0.1%. Using an optical model of the DichOS device, the positive and negative deviations which gave rise to an absolute error of 0.1% (+ve or −ve) for each parameter were determined. Most of the tolerances were then tightened to the nearest round figure, while a few were loosened slightly. The resulting set of tolerance values are shown in Table 7, below, which includes those derived in the above sections of the report. In the case of the waveplate thickness parameters, values are given for the both preferred embodiments, i.e. incorporating quartz waveplates and $MgF_2$ waveplates (the production model) where nominal thickness for the quartz waveplates is 132.8 μm and for the MgF2 waveplates it is 103.7 μm. The tolerances on these thicknesses was the same for both preferred embodiments (±0.1 μm).

The tolerance on the parameter $\theta_{WP2\_Z}$ (the axial alignment of the second waveplate) is defined as an offset from an orthogonal orientation with the first waveplate. This reflects the fact that the second waveplate will be aligned to the first waveplate on a specialised jig. Any error remaining after alignment is thus correctly expressed as a relative offset rather than an absolute deviation.

TABLE 7

| | Parameter Symbol | Parameter Description | Nominal Value | Tolerance | Error Dependence |
|---|---|---|---|---|---|
| Waveplate 1 | $\theta_{WP1\_X}$ | Waveplate 1 tilt about X | 0° | ±1° | S (−) |
| | $\theta_{WP1\_Y}$ | Waveplate 1 tilt about Y | 0° | ±1° | S (+) |
| | $\theta_{WP1\_Z}$ | Waveplate 1 tilt about Z | 45° | ±1° | S (−) |
| | $\theta_{WP1\_C}$ | Waveplate 1 C-axis error | 0° | ±0.5° | S (−) |
| | $t_{WP1}$ | Waveplate 1 thickness | 132.8 μm 103.7 μm | ±0.1 μm | S (−) |
| Waveplate 2 | $\theta_{WP2\_X}$ | Waveplate 2 tilt about X | 0° | ±1° | S (−) |
| | $\theta_{WP2\_Y}$ | Waveplate 2 tilt about Y | 0° | ±1° | S (+) |
| | $\theta_{WP2\_Zoff}$ | Waveplate 2 tilt about Z (offset) | 0° | ±1° | S (+)/L (−) |
| | $\theta_{WP2\_C}$ | Waveplate 2 C-axis error | 0° | ±0.5° | S (+) |
| | $t_{WP2}$ | Waveplate 2 thickness | 132.8 μm 103.7 μm | ±0.1 μm | S (+)/L (−) |
| Isoplate1 | $\theta_{IP1\_X}$ | Isoplate 1 tilt about X | 0° | ±1° | S (−) |
| | $\theta_{IP1\_Y}$ | Isoplate 1 tilt about Y ($\theta_P$) | 20° | ±0.017° | L (+) |
| Isoplate2 | $\theta_{IP2\_X}$ | Isoplate 2 tilt about X | 0° | ±1° | S (−) |
| | $\theta_{IP2\_Y}$ | Isoplate 2 tilt about Y (−$\theta_P$) | −20° | ±0.017° | L (−) |
| RA | $\theta_{RA}$ | Rotation axis deviation from Z | 0° | ±0.04° | N/A |
| Material | Δn | Isoplate refractive index | — | ±2 × 10⁻⁴ | L (+) |
| | ΔB | Waveplate birefringence | — | ±1 × 10⁻⁵ | S (−) |

Error Dependencies

The rightmost column in Table 7 indicates the nature of the ΔCD % error dependence on variations in each parameter. The meanings of the symbols listed are as follows:

L (+): ΔCD % varies linearly with the parameter deviation in direct proportion

L (−) ΔCD % varies linearly with the parameter deviation in inverse proportion

S (+) ΔCD % varies with the square of the parameter deviation and has positive sign S (−) ΔCD % varies with the square of the parameter deviation and has negative sign Where two dependencies are listed, the first corresponds to a system in which the detector has no polarisation bias, while the second corresponds to a system in which the detector does have a polarisation bias response. In the latter case the second waveplate has a more critical function within the overall device, restoring the circular polarisation state to minimise errors at the detector. This explains the change in error dependence.

Referring to Table 7, it can be seen that many of the tolerances are quite relaxed and should be easily achievable in manufacture. The tightest tolerances are those relating to the tilt angles of the isoplates ($\theta_{IP1\_Y}$ and $\theta_{IP2\_Y}$) which require 1 arc minute accuracy, and the alignment of the rotation axis ($\theta_{RA}$) which must coincide with the optical Z axis within 2.4 arc minutes.

Monte Carlo Simulations: Method and Setup

Figure 29:
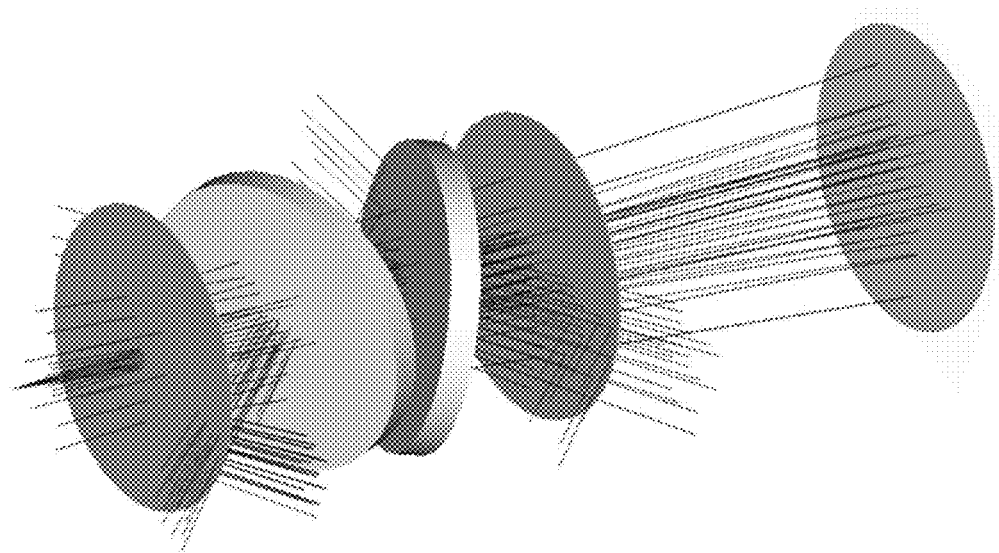
FIG. 29 shows the DichOS-6 Optical model for Monte-Carlo tolerance analysis.

Using a non-sequential optical model of the DichOS-6 device (FIG. 29), a series of Monte-Carlo simulations were run in which the each of the tolerance parameters were allowed to vary randomly with uniform distribution over the ranges specified in Table 7. The only tolerances not included in the simulations were those for the isoplate refractive index (n) and the waveplate birefringence (B). The effects of errors in these values are small (see supra) and so their absence from the simulations are expected to be of minor consequence.

For each tolerance run, a total of 10,000 Monte-Carlo simulations were performed at each of four wavelengths: 185 nm, 254 nm, 542 nm and 1500 nm, corresponding to peaks in the DichOS spectrum and spanning full operational range of the device.

In addition to tolerance variations, the Monte-Carlo simulations were also able to take account of beam errors (divergence and incident angle errors) and detector polarisation bias. The specification of these error conditions are described herein below.

Beam Errors

In order to cater for worst case conditions, the beam divergence values (half-angles) used in the Monte-Carlo simulations were defined as 3° in the horizontal and 3.5° in the vertical. The beam incidence angle was allowed to vary randomly in the vertical and horizontal directions over a range of ±2°, which is considered to represent the extremes likely to be encountered in practice:

The beam error conditions used in the simulations are summarized in Table 8 below:

TABLE 8

| | Parameter Symbol | Parameter Description | Nominal Value | Range |
|---|---|---|---|---|
| Beam Error | $\theta_{B\_X}$ | Beam incident angle vertical | 0° | ±2° |
| | $\theta_{B\_Y}$ | Beam Incident Angle horizontal | 0° | ±2° |
| | $\theta_{D\_X}$ | Beam divergence vertical | 3.5° | — |
| | $\theta_{D\_Y}$ | Beam divergence horizontal | 3.0° | — |

Detector Polarisation Bias

In order to account for worst case conditions, a detector polarisation bias of ΔR=1% was used in the Monte-Carlo simulations. This represents the difference in response when light is linearly polarised along a preferred axis compared to the response along the orthogonal axis. Photomultipliers tend to show a polarisation sensitivity while photodiode based detectors in general do not.

The detector bias was modelled by placing a Jones matrix surface in front of the detector with the following specification:

$$M_{bias} = \begin{bmatrix} \sqrt{1 + \Delta R/2} & 0 \\ 0 & \sqrt{1 - \Delta R/2} \end{bmatrix} = \begin{bmatrix} 1.0025 & 0 \\ 0 & 0.9975 \end{bmatrix} \quad (44)$$

In theory, the effect of detector polarisation bias is minimized when the preferred axis is oriented at an azimuth of ±45° from the horizontal. However, in general, a particular detector orientation on a given instrument cannot be enforced, and trying to do so would greatly complicate the use of the DichOS device as a CD standard. Hence, in the simulations, the orientation of the detector's preferred axis was allowed to vary randomly over the range 0° to 360°.

Monte Carlo Simulations: Results

The results of the Monte-Carlo simulations are presented in the form of histograms showing the distribution with respect to percent relative CD error (ΔCD %). The area under each distribution curve was normalized to unity. The mean value, 95% confidence interval and yield (proportion of systems lying within ±1%) are presented in table form after each histogram plot for each of the four wavelengths tested as shown in the Figures. The histogram plots may be assumed to apply to both preferred embodiments of the device, as defined supra.

Monte-Carlo Set 1: No Beam Errors, No Detector Bias

Figure 30:
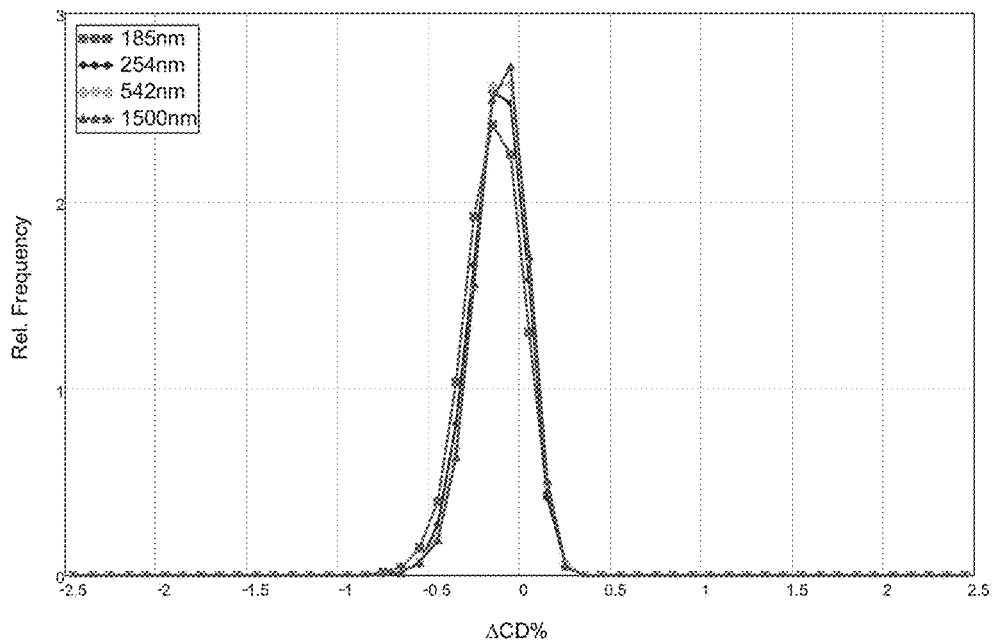
FIG. 30 shows Monte-Carlo results, no beam errors, no detector bias.

The first Monte-Carlo dataset is shown in FIG. 30 and serves to illustrate the effect of the construction tolerances (see Table 7) acting alone in the absence of beam errors and detector polarisation bias. The distribution lies comfortably within the ±1% zone. The mean value of ΔCD % is slightly negative because of the preponderance of parameters with S(−) error dependence (see Table 7). There is a very slight spreading of the distribution and shift to the left towards UV wavelengths, highlighting the greater error sensitivity in this region. Since there are no beam errors, there is no improvement to be gained in using 'rotate & average' or '3-angle' correction. This therefore represents the best result attainable given the set of construction tolerances listed in Table 7.

Monte-Carlo Set 2: Beam Errors+Detector Bias, No Correction

Figure 31:
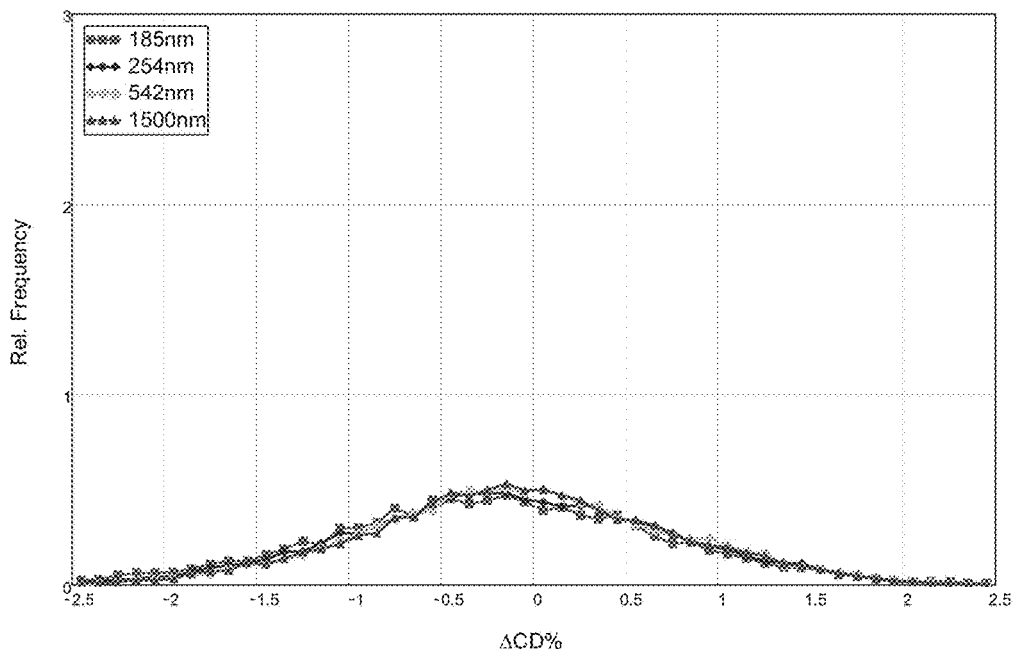
FIG. 31 shows Monte-Carlo results, beam errors+detector bias, no correction.

Dataset 2 shown in FIG. 31 shows the effect of beam errors and detector polarisation bias acting together when no correction is applied. Here, a significant broadening in the distribution is seen, with little change in the mean values at each wavelength. This represents worst-case conditions, with yields only in the mid 70% percent region.

Monte-Carlo Set 3: Beam Errors+Detector Bias, Rotate & average Correction

Figure 32:
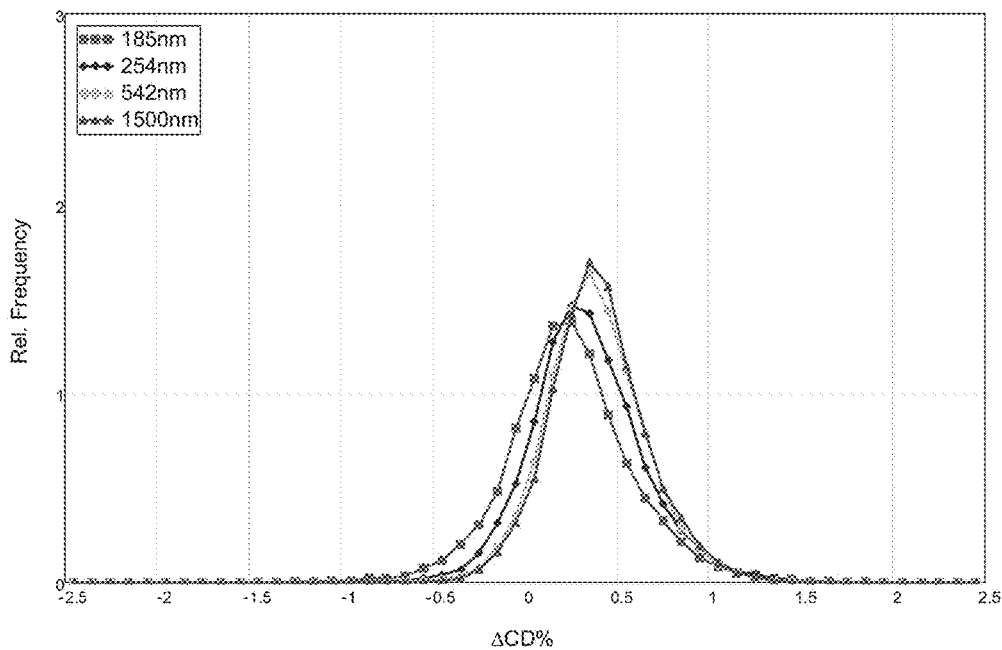
FIG. 32 shows Monte-Carlo results, beam errors+detector bias, rotate & average correction.

In dataset 3, shown in FIG. 32, the improvement in CD error due to rotate & average correction is shown when both beam errors and detector polarisation bias are in effect. The distributions have considerably narrowed compared with Monte-Carlo Set 2 (see supra), and there is now a positive offset which is slightly wavelength dependent. UV wavelengths also appear subject to slightly more broadening than those at the red end of the spectrum. The yield is close to 100% for all wavelengths.

Monte-Carlo Set 4: Beam Errors+Detector Bias, 3-angle Correction

Figure 33:
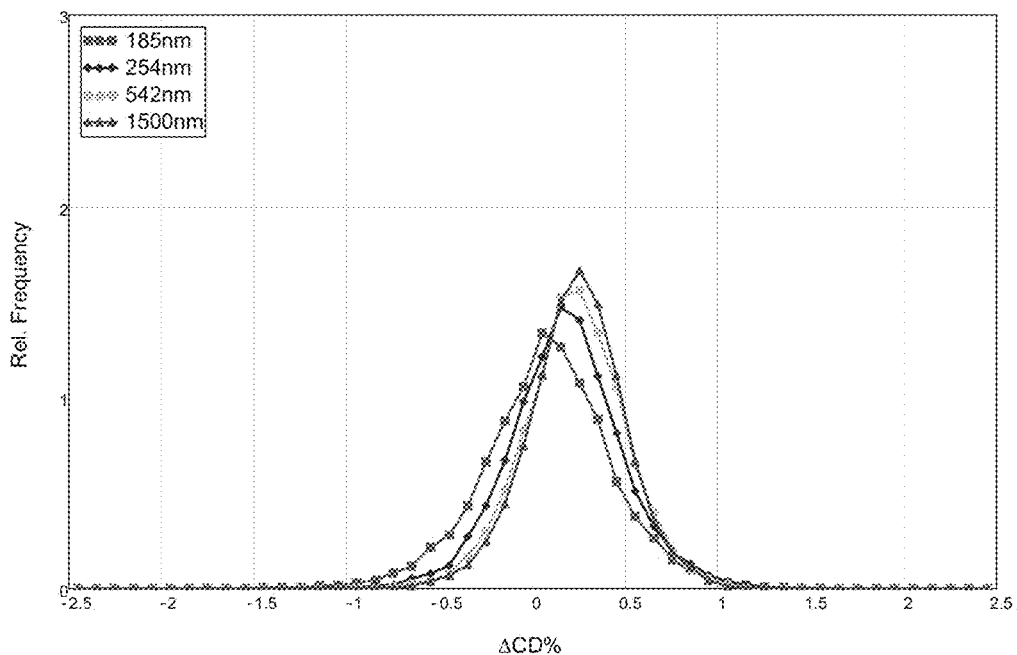
FIG. 33 shows Monte-Carlo results, beam errors+detector bias, 3-angle correction.

The final dataset shown in FIG. 33 shows the distributions resulting after 3-angle correction (version C) has been applied when both beam errors and detector polarisation bias are present. The effect of 3-angle correction, compared with rotate & average (Monte-Carlo Set 3) is to shift the errors to the left, leading to more centred distributions. The centering is not perfect since 3-angle correction cannot completely correct for beam divergence errors, as discussed supra.

The yield is now restored to nearly 100% at all wavelengths, indicating that the tolerance values defined in Table 3 are suitable for production of DichOS devices. These results apply to both of the preferred embodiments of the optical device specified supra.

Temperature Dependence

The majority of the parameters defining a DichOS device are angular construction values (see Table 6). Provided that the optical housing and mounted optical elements have no significant internal strains and can expand or contract freely without interferences being introduced, the angular parameters may be assumed to be independent of temperature. This results from the fact that isotropic linear expansions or contractions acting in three dimensions will in general be angle preserving. Hence in the analysis of the temperature dependence of the DichOS-6 device, there are only two factors which need to be considered:

Changes in the refractive index of the isoplates (n)
Changes in the phase retardance of the waveplates (Φ)

In the analyses which follow, a nominal temperature of 20° C. is assumed and the effect of +10° C. and −10° C. deviations from this value are considered (as specified in 'Performance Criteria', described herein above).

Change in Isoplate Refractive Index with Temperature

The effect of a change in n due to temperature change ΔT on the DichOS CD signal magnitude may be described by a simple modification to equation (29) as follows:

$$\Delta CD\ \% = \frac{\Delta CD}{CD} \times 100 = \frac{100}{LD_{plates}} \frac{dLD_{plates}}{dn} \cdot \frac{dn}{dT} \Delta T \quad (45)$$

Where the substitution $$\Delta n = \frac{dn}{dT}\Delta T$$

has been made.

Figure 34:
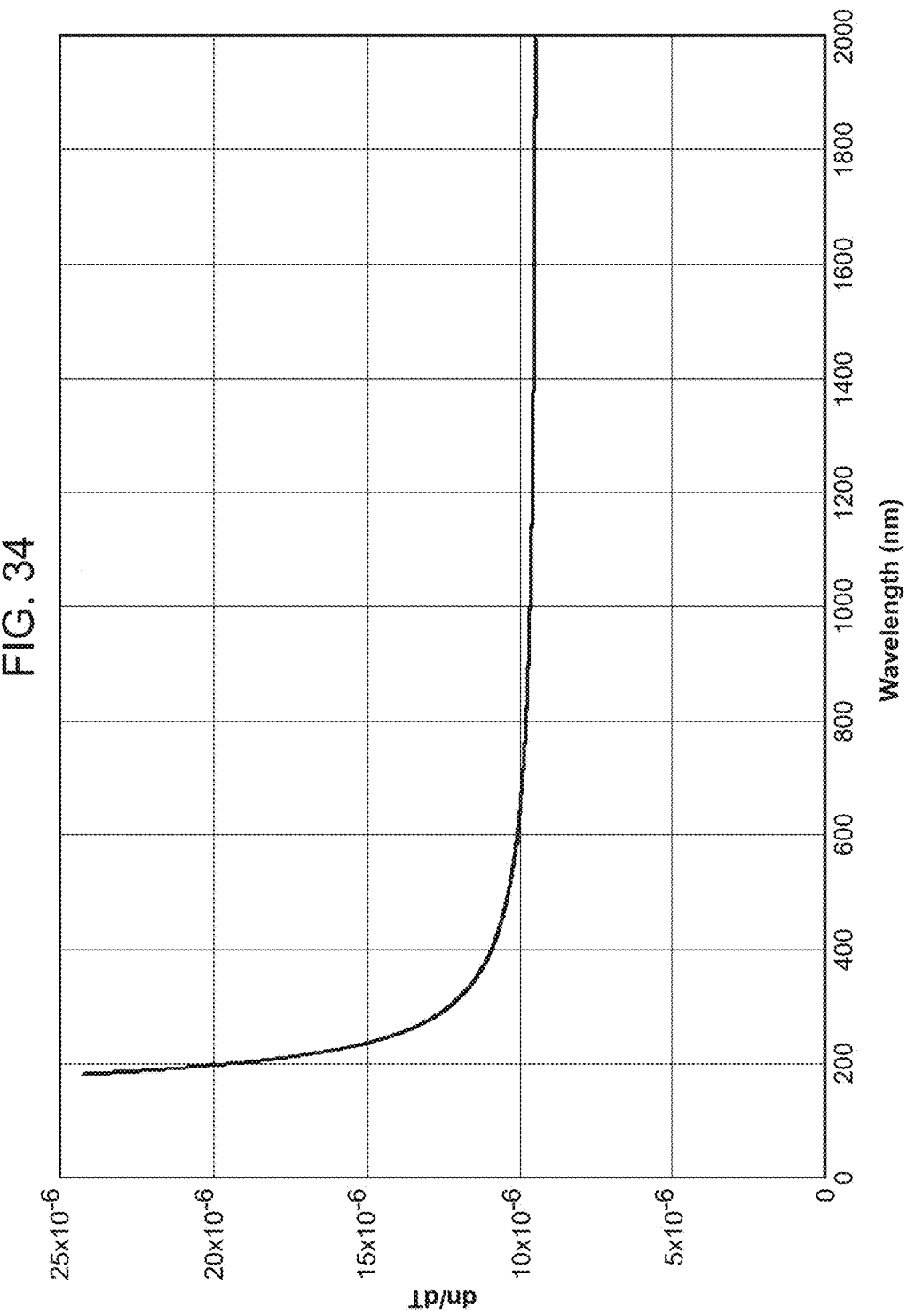
FIG. 34 is a graph that shows the temperature coefficient of fused silica refractive index (n).
Figure 35:
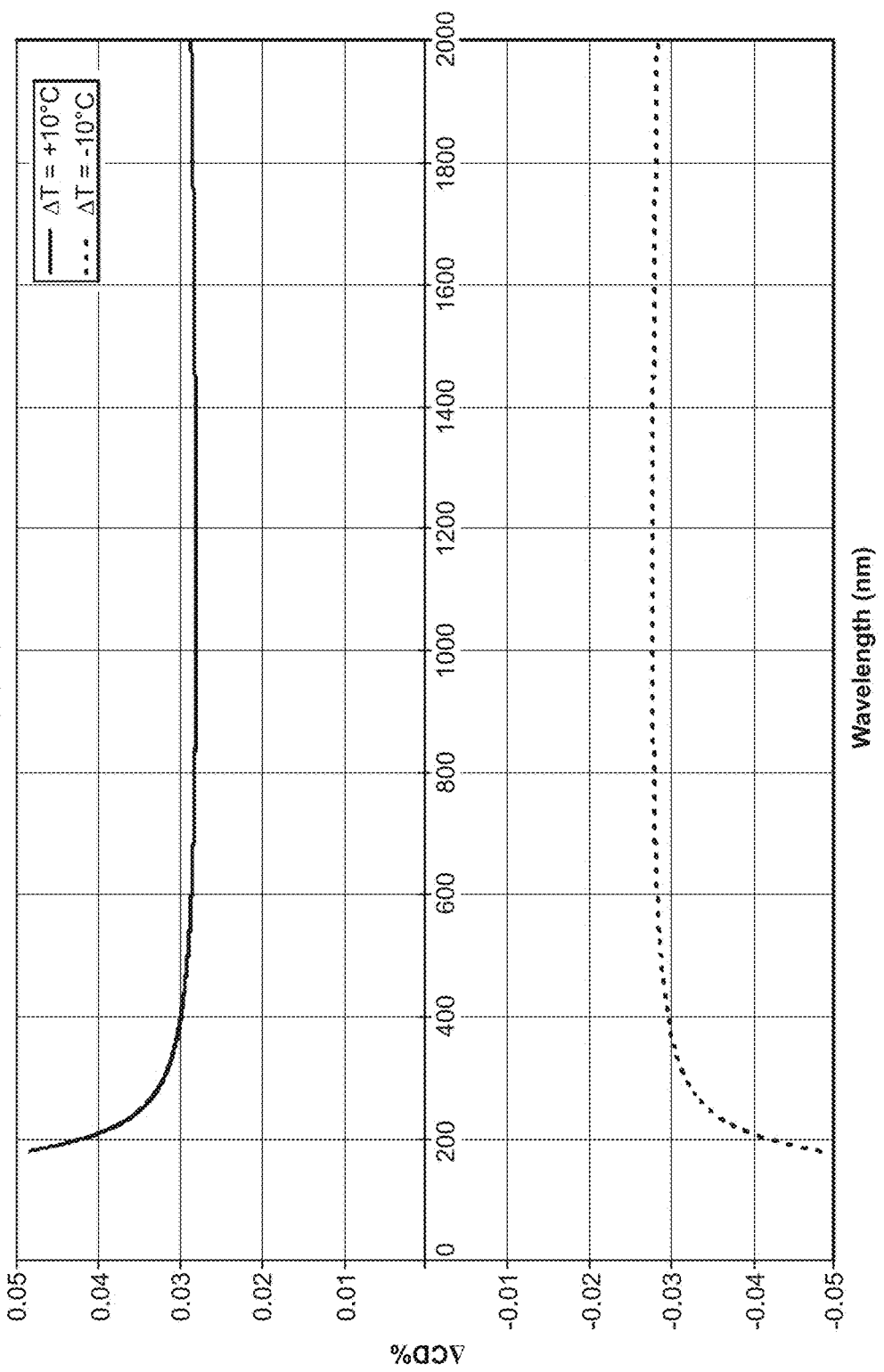
FIG. 35 is a graph that shows $\Delta CD$ % for a temperature change of $\pm 10°$ C.

For the temperature coefficient of refractive index of fused silica $$\left(\frac{dn}{dT}\right),$$

an empirical equation supplied by Corning Inc. ("HPFS Fused Silica ArF Grade", Company product brochure, 2003) is used, which is in good general agreement with earlier data due to Malitson (J. Opt. Soc. Am., 55, 1205 (1965) (the Malitson values are slightly lower in magnitude). The Corning curve for $$\left(\frac{dn}{dT}\right)$$

is plotted in FIG. 34 and allows equation (45) to be evaluated as a function of wavelength. The resulting CD error curve is shown in FIG. 35 for a temperature change of ±10° C., where we see that the error lies in a band just under ±0.05% at the UV end of the spectrum, and just under ±0.03% at the IR end.

Given that these errors are small fraction of the ±1% criterion for Δ% CD (see supra), it may be concluded that the DichOS signal magnitude will remain within specification over a temperature range of 20° C.±10° C.

Change in Waveplate Phase Retardance with Temperature

The effect of a change in waveplate retardance Φ due to temperature is to cause a wavelength shift in the DichOS spectrum, rather than a CD magnitude change. To calculate this the normalized temperature derivative of retardance ($\gamma$) is defined (P. D. Hale and G. W. Day, "Stability of birefringent linear retarders (waveplates)", Appl. Opt. 27, 5146 (1988)):

$$\gamma = \frac{1}{\Phi}\frac{d\Phi}{dT} = \frac{1}{t_{WP}}\frac{dt_{WP}}{dT} + \frac{1}{B}\frac{dB}{dT} \quad (46)$$

The left hand term on the right side of the equation is simply the thermal expansion coefficient of the waveplate material in the direction orthogonal to the C-axis ($\alpha_a$), which has an approximate value of $13 \times 10^{-6}/°$ C. at room temperature for quartz and $8.9 \times 10^{-6}/°$ C. at room temperature for magnesium fluoride.

$$\left(\frac{dB}{dT}\right)$$

is the temperature coefficient of the birefringence of quartz.

Figure 36A:
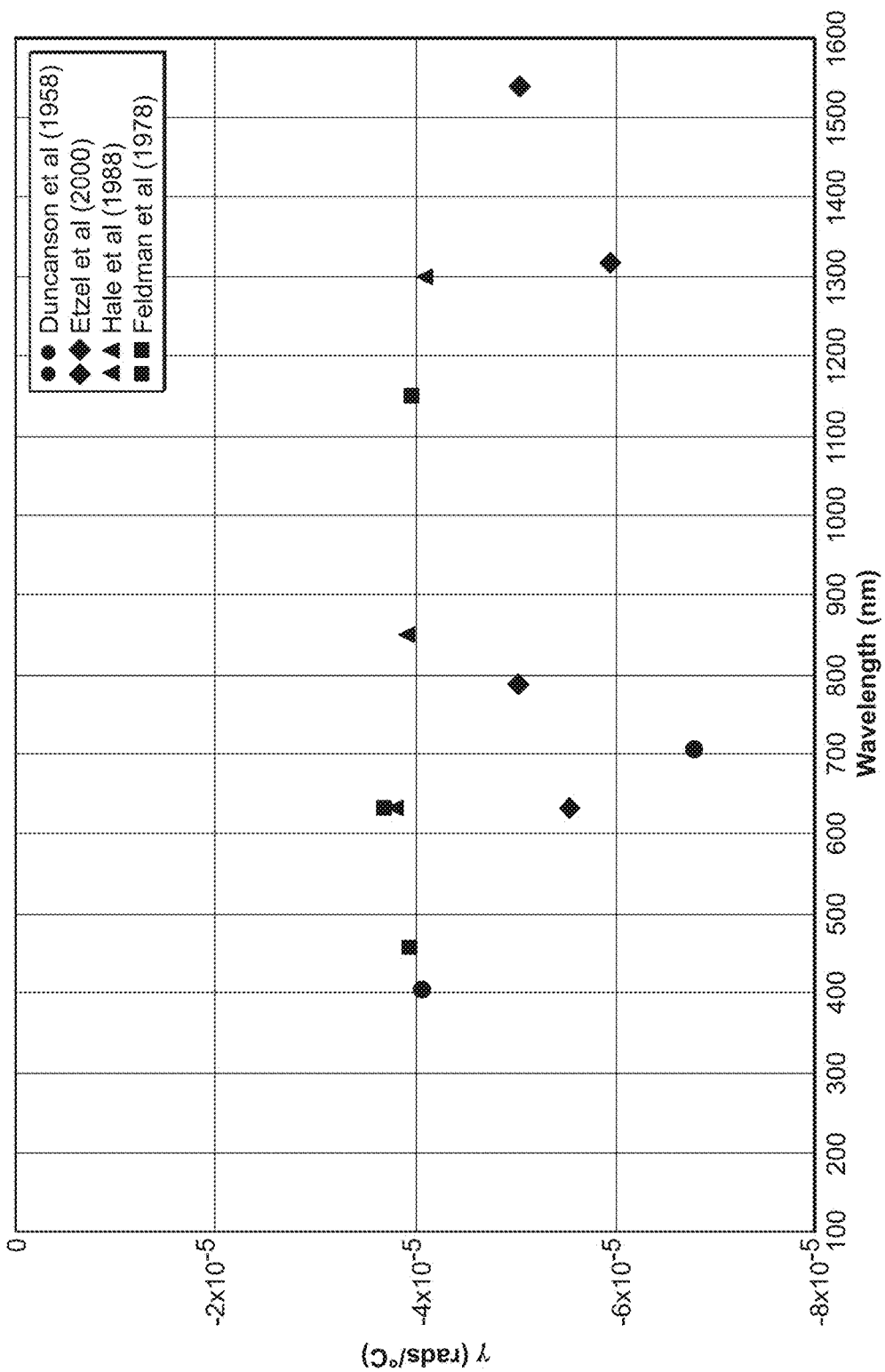
FIG. 36(a) is a graph that shows published measurements of γ (the normalized temperature derivative of retardation) for magnesium fluoride ($MgF_2$).

Some measurements of $\gamma$ for magnesium fluoride from four independent studies are shown plotted in FIG. 36(a). The literature sources for these datasets are: A. Duncanson and R. W. H. Stevenson, Proc. Phys. Soc. (Lond.), 72, 1001, (1958). S. M. Etzel, A. H. Rose and C. M. Wang, "Dispersion of the temperature dependence of the retardance in SiO2 and MgF2", Appl. Opt. 39, 5796 (2000). P. D. Hale and G. W. Day, "Stability of birefringent linear retarders (waveplates)", Appl. Opt. 27, 5146 (1988). A. Feldman, D. Horowitz, R. M. Waxler and M. J. Dodge, "Optical Materials Characterization", Natl. Bur. Stand. (U.S.) Tech. Note 993 (1979). Unfortunately, there are no data points below 400 nm in any of these studies.

While there is a fair amount of spread in the values from the various studies mentioned supra, the general consensus is that $\gamma$ is reasonably constant with wavelength. We therefore assume a fixed value of $\gamma=-5\times 10^{-5}$ for magnesium fluoride, on the basis that this will most likely overestimate $\gamma$ at wavelengths below 400 nm, and hence overestimate (rather than underestimate) the resulting wavelength errors caused by a temperature shift.

Some recent measurements of $\gamma$ for crystalline quartz (S. M. Etzel, A. H. Rose and C. M. Wang, "Dispersion of the temperature dependence of the retardance in SiO2 and MgF2", Appl. Opt. 39, 5796 (2000)) appear to be in good agreement with the data of Smartt & Steel (R. N. Smartt and W. H. Steel, "Birefringence of Quartz and Calcite", J. Opt. Soc. Am. 49, 710 (1959)), however neither of these studies provide data points in the UV region. Other recent studies appear to contain large errors and are not considered reliable. To obtain values of $\gamma$ below 400 nm we must therefore rely on the much older work of Micheli (Ann. Physik, 4, 7 (1902)) and Macé de Lépinay (J. Phys. I, 23 (1892)) who provided an empirical equation for the birefringence of quartz including its temperature dependence. Using the temperature derivative of Macé de Lépinay's equation we may determine a function for $\gamma$ versus wavelength as follows:

$$\gamma(\lambda) = \frac{(0.2\lambda^2 + 1.01)(900 + 2T)}{B(\lambda) \cdot 9 \times 10^8} + \alpha_a \quad (47)$$

Where $\lambda$ is the wavelength in microns, $\alpha_a \approx 13 \times 10^{-6}$ and $B(\gamma)$ is the model birefringence for quartz. T is the nominal temperature which here is assigned the value of 20° C.

The four literature sources for $\gamma$ of quartz mentioned above are plotted in FIG. 36(b), where it is clear that there is a drop in the absolute magnitude of $\gamma$ towards the UV end of the spectrum. The curve due to Macé de Lépinay appears to overestimate the magnitude of $\gamma$ below 300 nm and above 800 nm. Hence if we make use of this curve for our error calculations, it is likely that the errors will be overestimated, rather than underestimated in these regions. This was chosen as the safest approach given the lack of more recent data for $\gamma$. Furthermore, the fact that $\gamma$ is then in functional form rather than a discrete set of data points is of convenience in the calculations which follow.

Given a temperature change $\Delta T$, the wavelength shift may be defined as follows:

$$\Delta \lambda = \frac{d\lambda}{dT}\Delta T = \left(\frac{d\Phi}{dT} \middle/ \frac{d\Phi}{d\lambda}\right)\Delta T \quad (48)$$

Then we note from equation (46) that:

$$\frac{d\Phi}{dT} = \Phi \cdot \gamma \quad (49)$$

So the wavelength shift due to temperature change $\Delta T$ may be expressed as:

$$\Delta \lambda = \frac{\gamma(\lambda) \cdot \Phi(\lambda)}{\frac{d\Phi}{d\lambda}} \cdot \Delta T \quad (50)$$

Figure 37A:
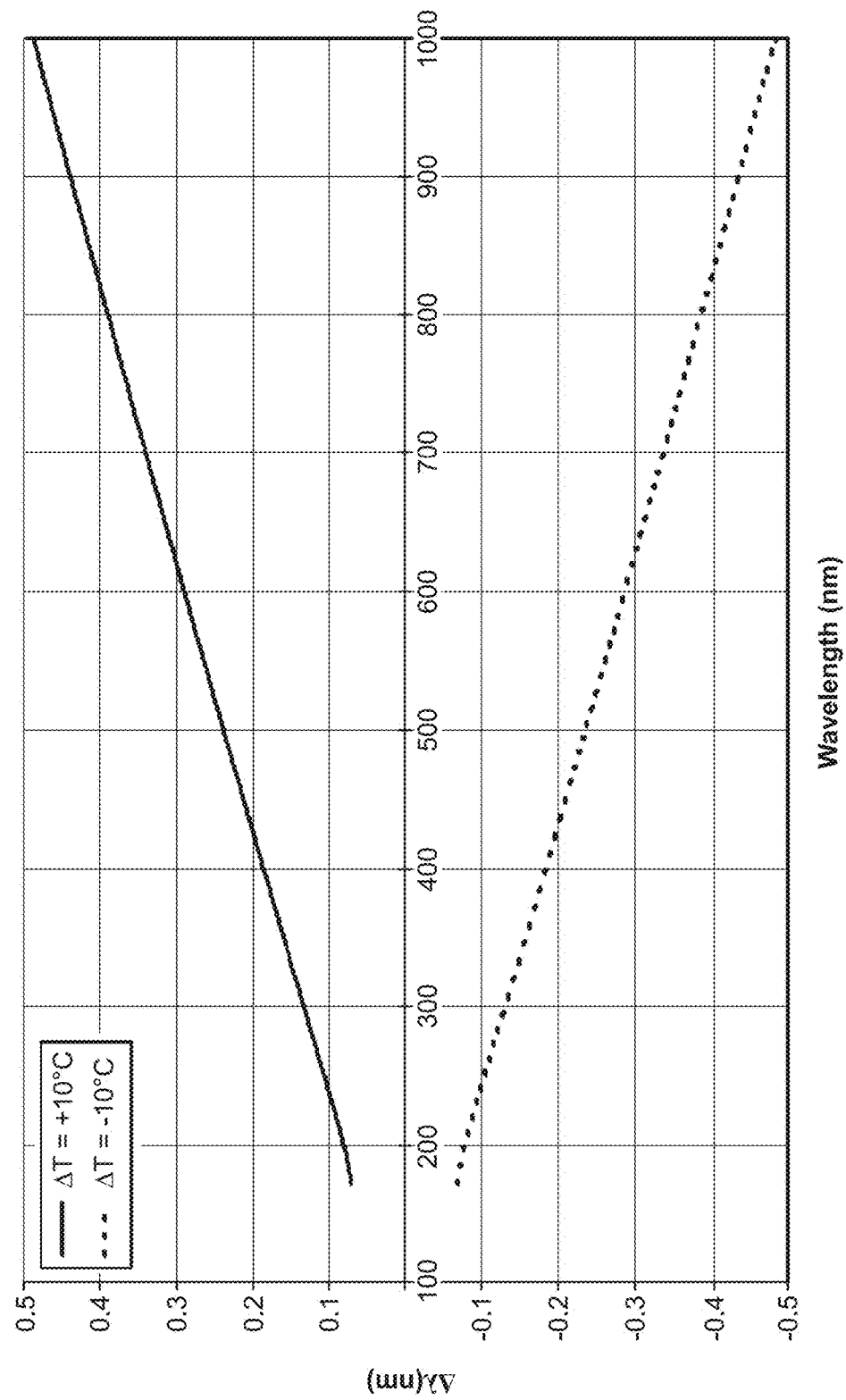
FIG. 37(a) is a graph that shows the wavelength shift for a temperature change of $\pm 10°$ C. for one preferred embodiment (with $MgF_2$ waveplates).
Figure 38A:
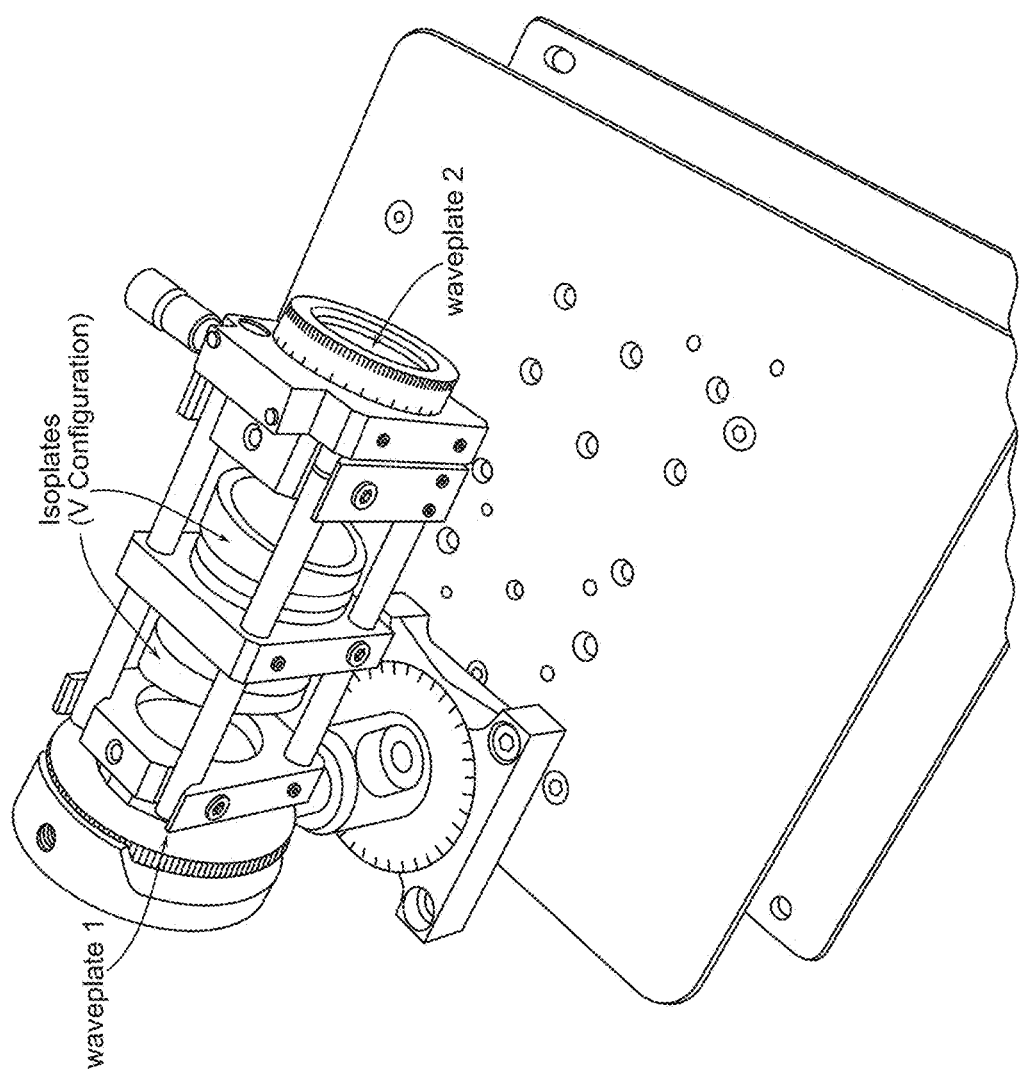
FIG. 38 (a) shows a prototype configuration for the optical device, (b) shows how the N-plates attach to the main assembly, (c) shows how the V-plates attach to the main assembly and (d) shows a production model of the optical device with integrated rotation actuation, based on one preferred embodiment of the device (with $MgF_2$ waveplates).
Figure 38B:
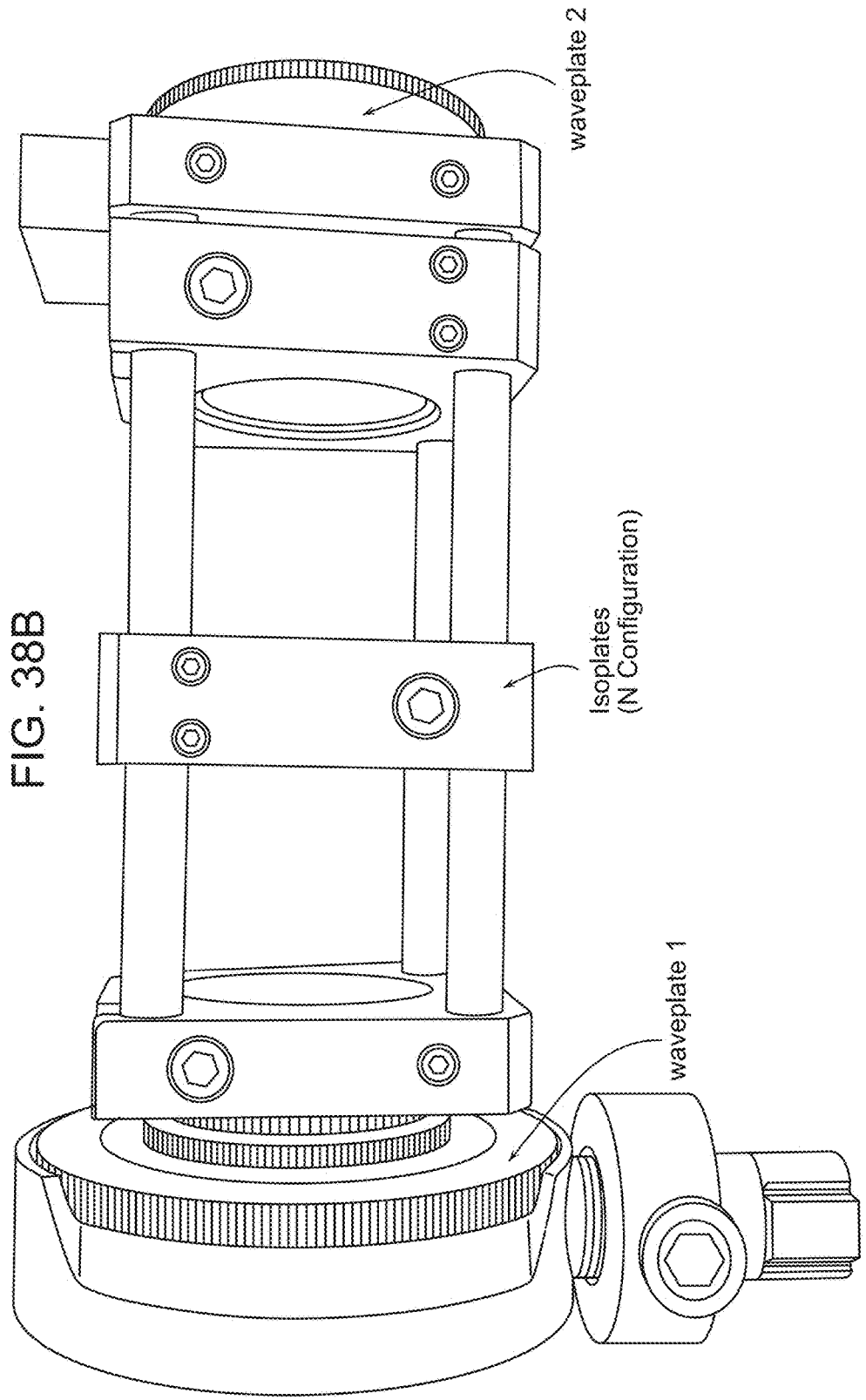
Figure 38C:
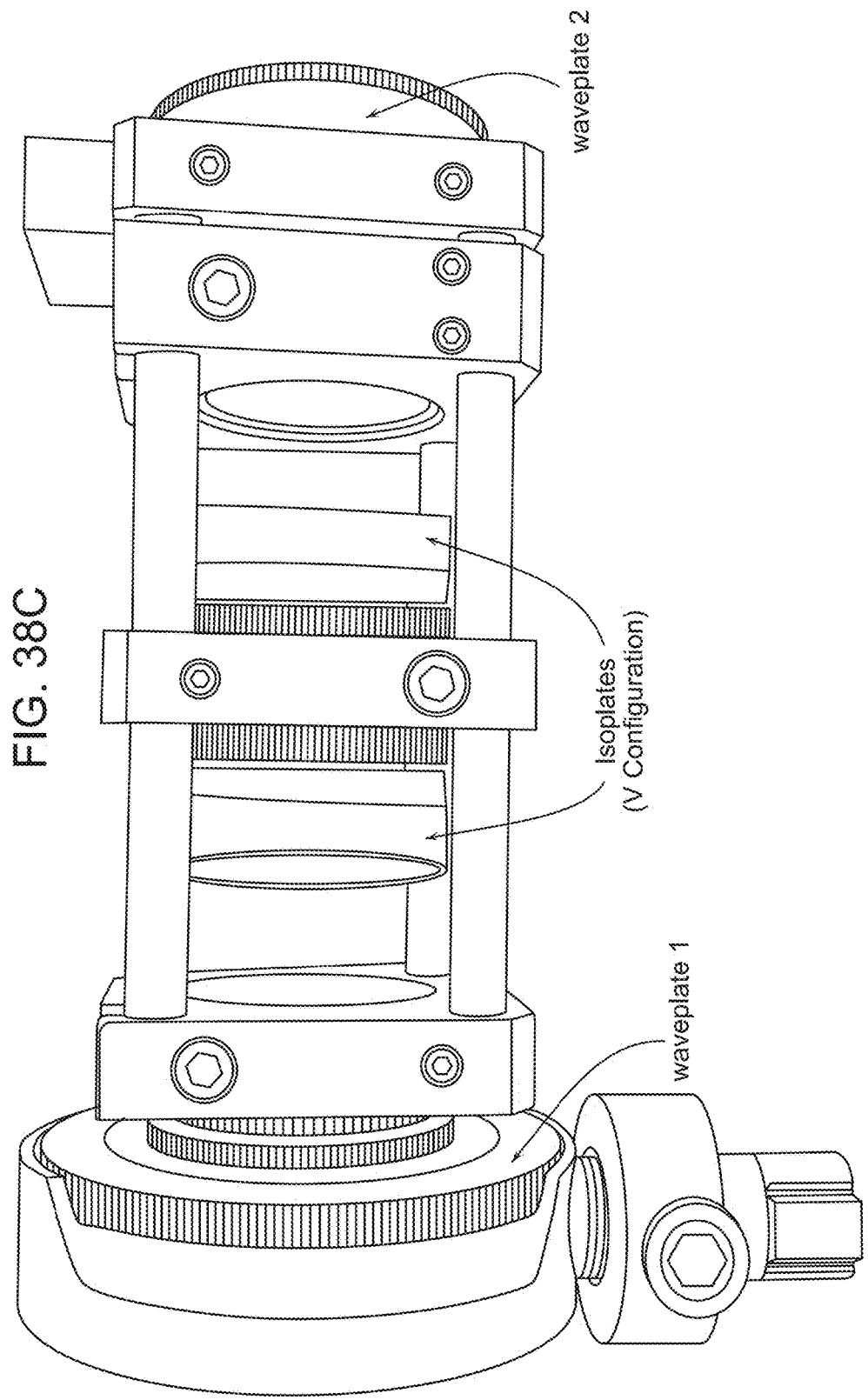
Figure 38D:
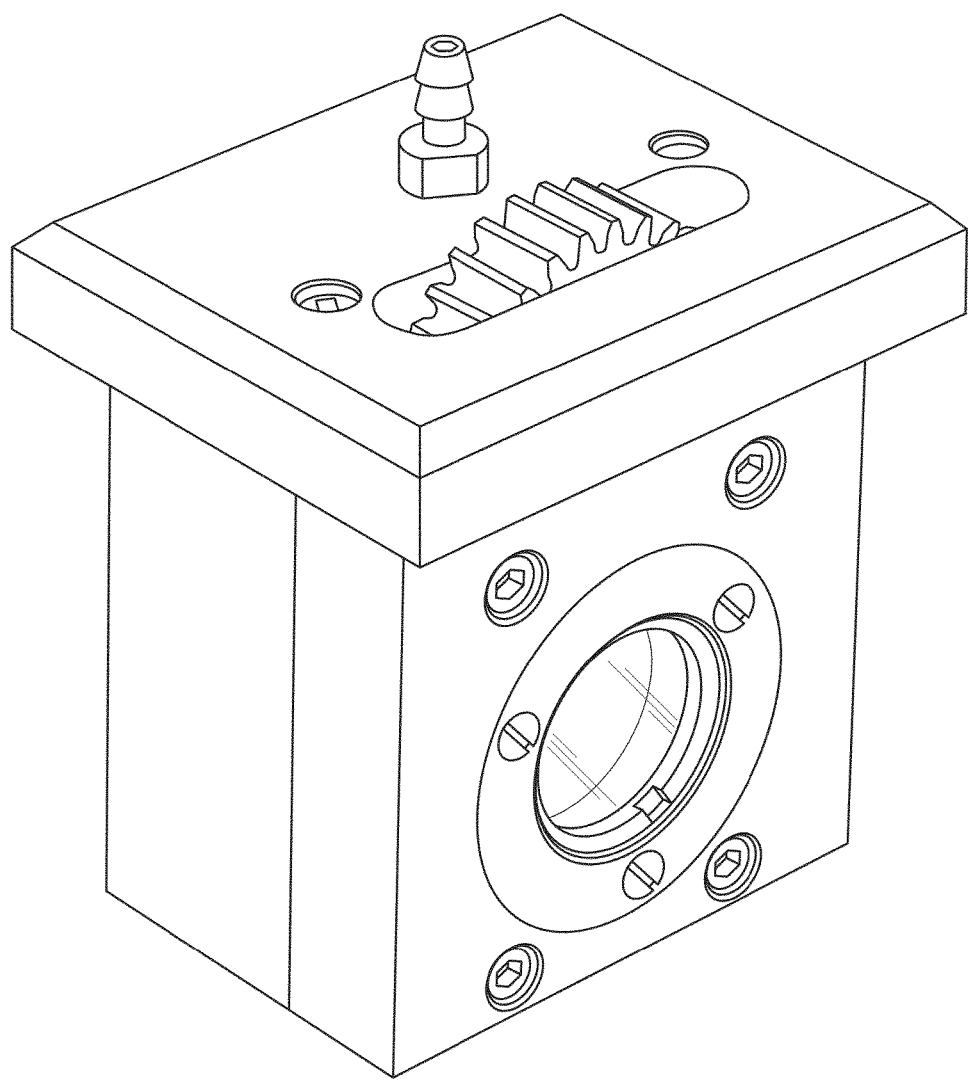

In FIG. 37(a), the wavelength shift corresponding to a temperature change of $\pm 10°$ C. is plotted against wavelength for one preferred embodiment (the proposed production specification) specified supra which incorporates MgF$_2$ waveplates. At 180 nm the shift lies in a band of approximately $\pm 0.07$ nm, while at 1000 nm it is within $\pm 0.5$ nm. The shift is a little outside of specification at 180 nm, but it is very likely that $\gamma$ has been overestimated here and that the actual shift will be lower. At 1000 nm the wavelength shift is comfortably inside required $\pm 1.0$ nm specification defined supra.

In FIG. 37(b), the wavelength shift corresponding to a temperature change of $\pm 10°$ C. is plotted against wavelength for another preferred embodiment specified supra which incorporates quartz waveplates. At 180 nm the shift lies in a band of approximately $\pm 0.044$ nm, while at 1000 nm it is within $\pm 1.22$ nm. This is only slightly out of the $\pm 1.0$ nm specification defined supra.

Given the known overestimations in the above calculations, we may fairly safely conclude that a DichOS device, in either of the two preferred embodiments analysed, will remain within its wavelength specification over a temperature range of 20° C.$\pm 10°$ C.

Conclusion

It has been demonstrated, through a series of Monte-Carlo simulations on an optical model of the DichOS-6 device, that if such a device is constructed according to the tolerances listed in Table 7, it will meet the performance criteria prescribed in this report. In particular, the percentage CD error ($\Delta$CD %) will lie within a $\pm 1\%$ of the nominal (calculated) value, provided that:

The measurement is performed using at least 'rotate & average' correction, and preferably '3-angle correction'.

The CD spectrometer being calibrated conforms to the instrument conditions specified in Table 8. It may also be noted that beam error and detector polarisation bias conditions utilized in this study are considered to represent the extremes of what is likely to be encountered in practice. A 'typical' system is expected to present less demanding instrument conditions.

Furthermore, it has been demonstrated that the device will remain within specification over a temperature range of 20° C.±10° C., where 20° C. is taken to be the nominal temperature of a typical laboratory environment.

The results presented above apply to both of the preferred embodiments defined supra, including the proposed production specification for the device. The Monte-Carlo analysis has been performed on both preferred embodiments (incorporating quartz and MgF2 waveplates) and found to give virtually identical results for the two embodiments.

Example 6—Prototype Test Results

In order to test the concept of the optical device, a prototype test rig was set up which could be fitted into a sample chamber (see FIG. 38: a, b & c). The prototype was constructed using mounting and rotation stage components mounted onto rails which were screwed to a standard cell-block mounting platform. To construct the V-plates, two 10° angled lens tubes were fitted into a cage-plate (for a $\theta_{IP}$ angle of 10°). Further testing was later performed on a production model of the device (see FIG. 38 (d)) built to one preferred configuration (with MgF$_2$ waveplates).

In the prototype device, the waveplates were uncoated quartz retarders specified as 2.5 waves at 532 nm, and are commercially available. The two fused-silica plates were 3 mm thick, and are also commercially available.

In the production device, the waveplates were uncoated magnesium fluoride retarders specified as 2.25 waves at 546.1 nm, and are commercially available as custom components. The two fused silica plates were 1 mm thick and are also commercially available as custom components.

Angular alignment of the prototype was performed, minimizing or maximising signal levels according to which element was being adjusted. This method of alignment was imperfect and better alignment is expected for the production device.

Angular alignment of the production model was performed using a specialized jig comprising precisely aligned calcite Glan-Taylor polarizers.

The CD instrument used for testing was carefully wavelength calibrated prior to running any tests. The CD scales (for PMT and LAAPD detectors) were calibrated using a freshly prepared CSA sample.

The parameter values which gave the best fit of experimental data with theory for the prototype device were as follows:

$\theta_{IP}=10.2°$ $t_{WP}=0.14395$ mm     (51)

The parameter values giving the best experimental fit for the production device were equivalent to the design specification values, namely:

$\theta_{IP}=20.0°$ $t_{WP}=0.1037$ mm     (52)

The departure of the $\theta_{IP}$ from 10° for the prototype device can easily be explained by setup tolerances in the Thorlabs mounting components. Also this parameter would compensate for any error in the instrument CD calibration values. The waveplate thickness value was in excellent agreement with the measured values provided by the supplier, which were 0.1433 mm and 0.1439 mm. The thickness value above corresponds to a retardation of approximately 2.49 waves at 532 nm.

Measured vs Calculated Results

Figure 39A:
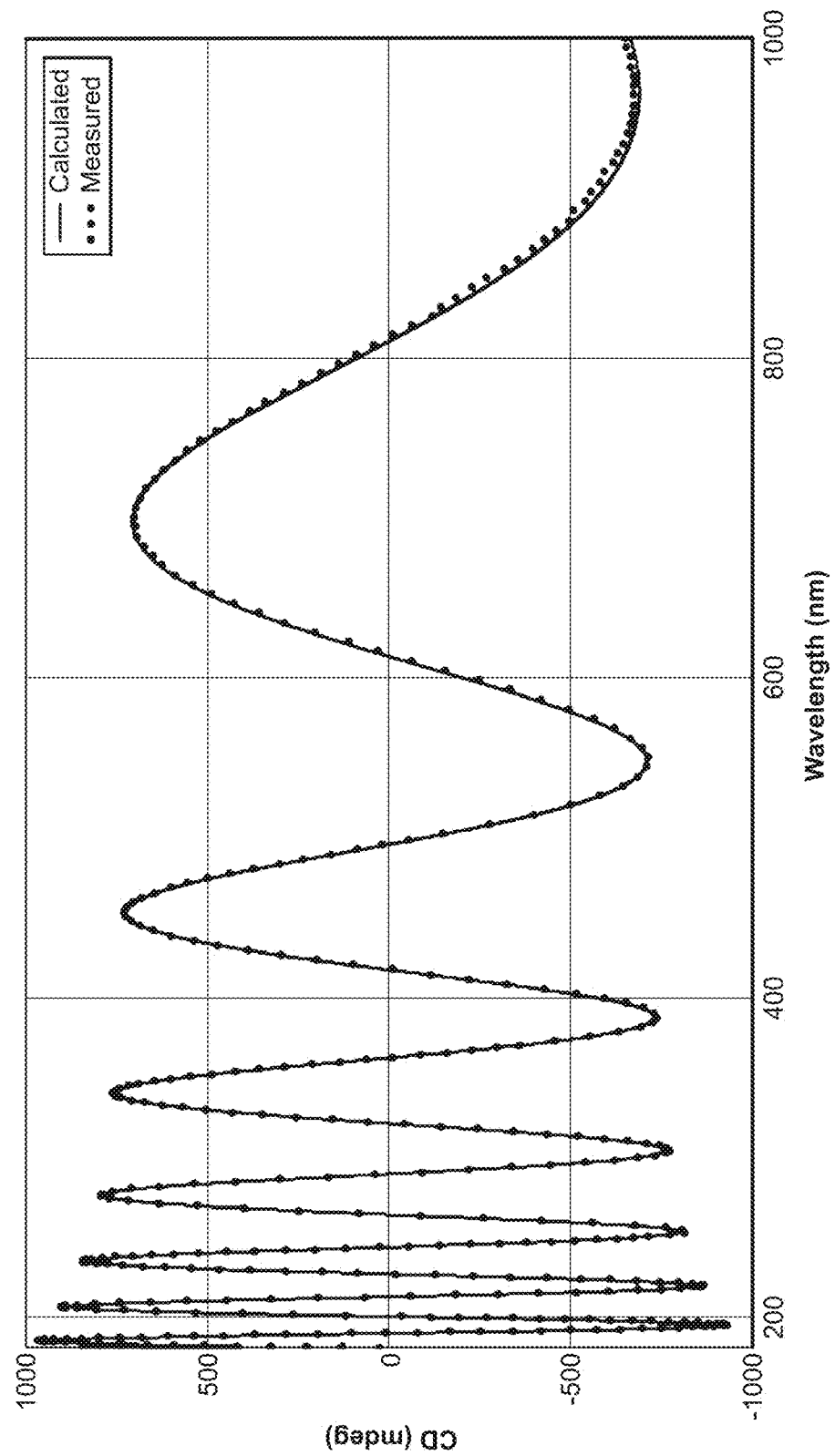
FIG. 39(a) is a graph that shows the spectrum of one preferred embodiment of the optical device (with $MgF_2$ waveplates) measured with an LAAPD detector and using R&A correction, overlaid with the calculated spectrum, covering the wavelength range 200 nm to 900 nm.
Figure 39B:
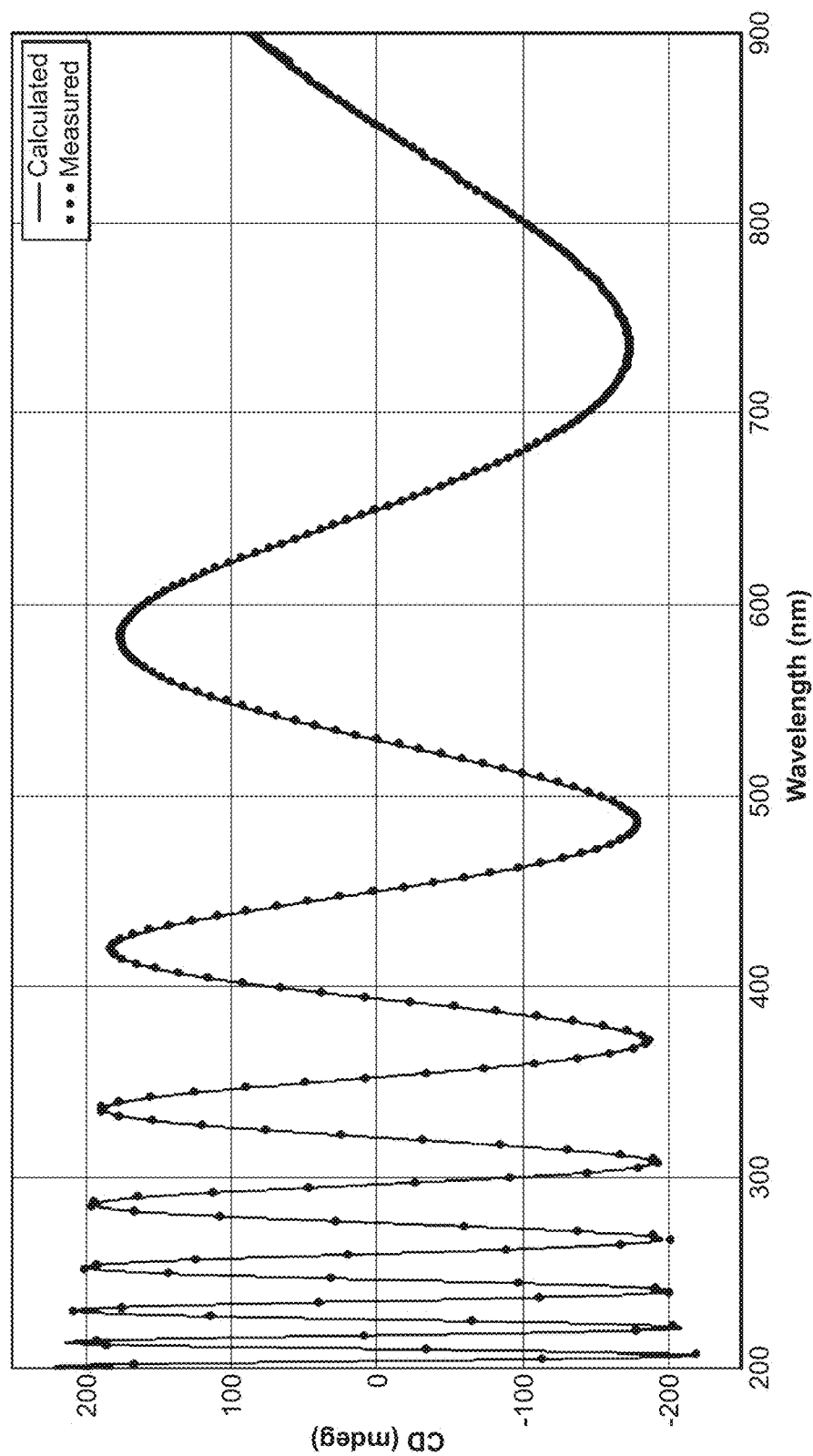
FIG. 39(b) is a graph that shows the spectrum of a prototype configuration of the optical device (with quartz waveplates) measured with an LAAPD detector and using R&A correction, overlaid with the calculated spectrum, covering the wavelength range 200 nm to 900 nm.
Figure 40A:
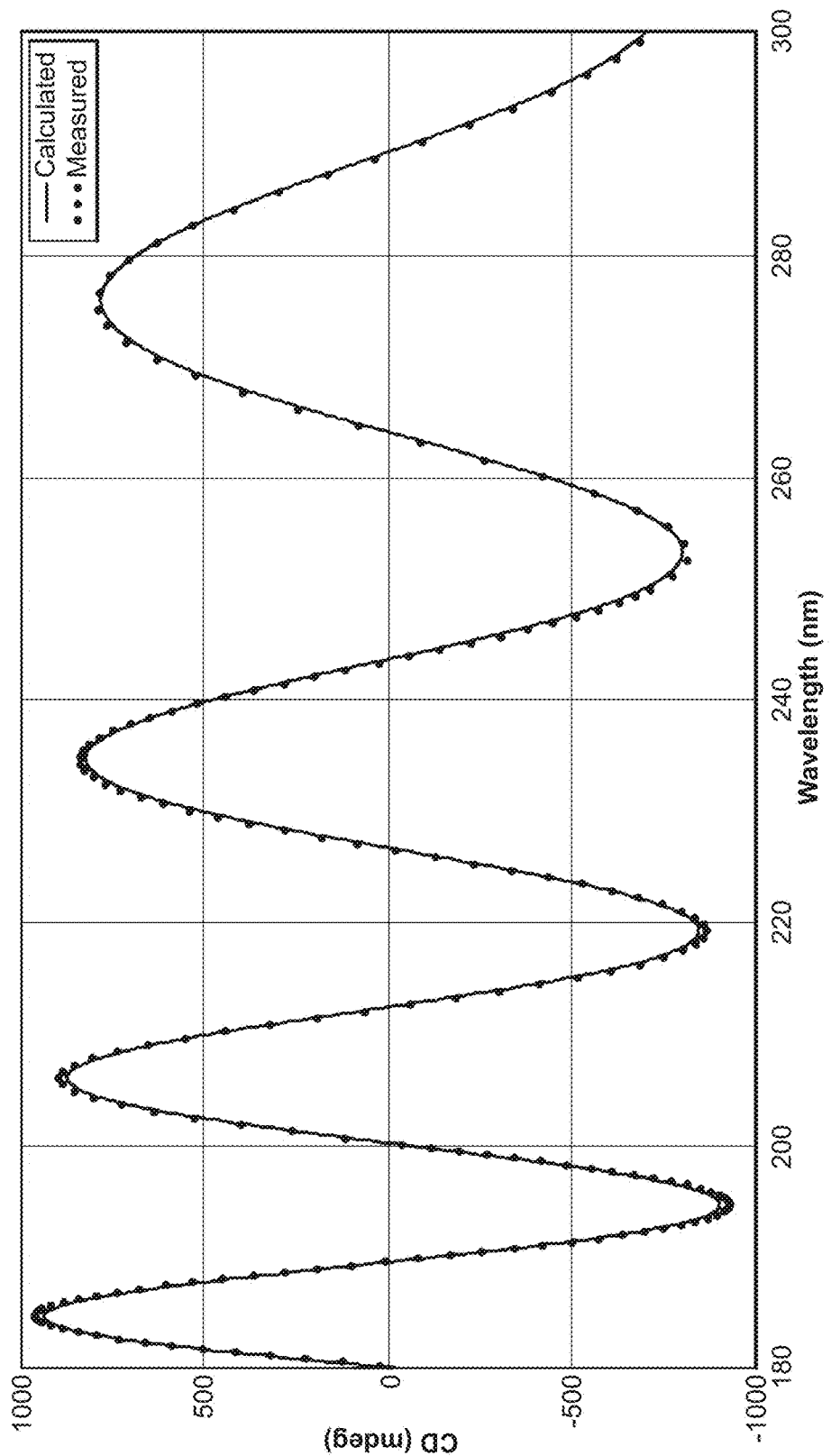
FIG. 40(a) is a graph that shows the spectrum of one preferred embodiment of the optical device (with $MgF_2$ waveplates) measured with an LAAPD detector and using R&A correction, overlaid with the calculated spectrum, covering the wavelength range 180 nm to 300 nm.

The overlay of the measured spectrum with the calculated spectrum is shown in FIG. 39(a) for the production device and FIG. 39(b) for the prototype device, with a close-up of the UV region shown in FIG. 40 (a and b). The measured spectra were recorded using an LAAPD detector and corrected for beam errors using rotate & average correction. Baselines were also measured and subtracted.

There is evidence of some mismatch of peak heights in the UV part of the spectrum (see FIG. 40). These discrepancies are very likely indicative of instrumental CD errors exposed by the DichOS optical device.

Figure 40B:
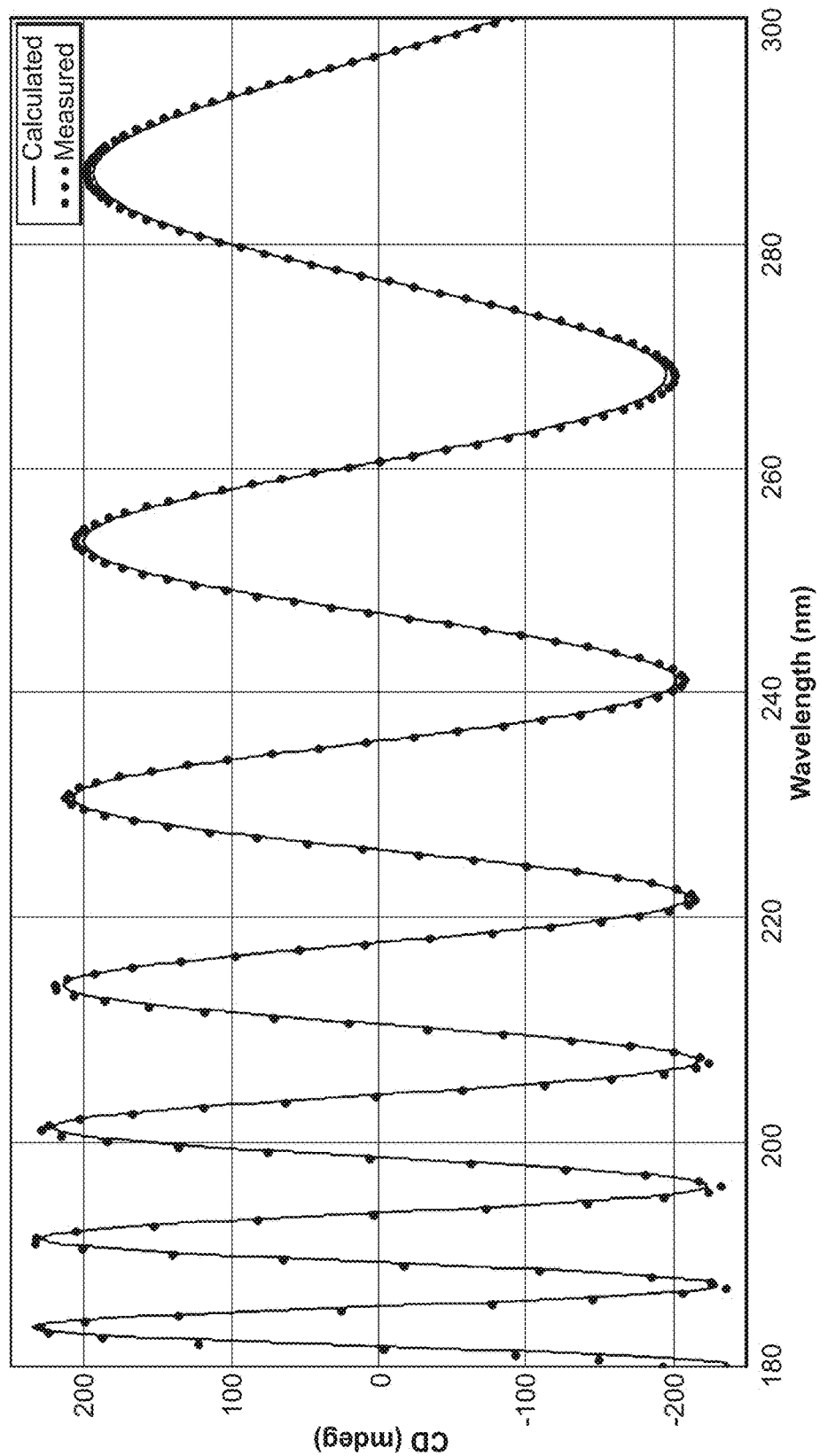
FIG. 40(b) is a graph that shows the spectrum of a prototype configuration of the optical device (with quartz waveplates) measured with an LAAPD detector and using R&A correction) overlaid with the calculated spectrum, covering the wavelength range 180 nm to 300 nm.

In the VUV region towards 180 nm (FIG. 40(b)), a small mismatch in the peak and crossover points is observed. This is suggestive of possible inaccuracies in the refractive index model for the quartz comprising the waveplates, as discussed supra. The mismatch is less obvious for the production device (FIG. 40(a)) suggesting that the refractive index model for magnesium fluoride is more accurate.

PMT Angle Dependence

Figure 41:
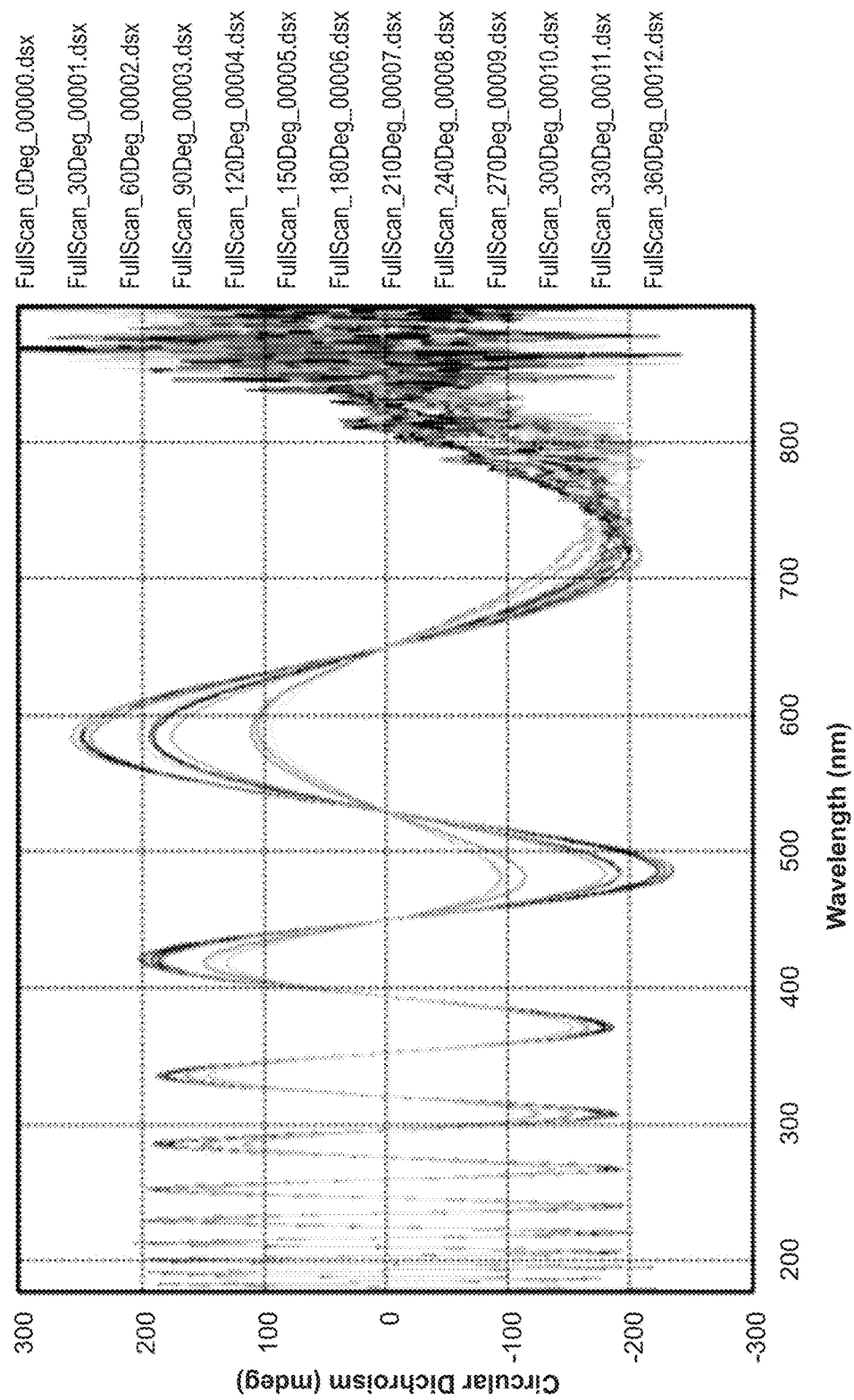
FIG. 41 is a graph that shows the PMT detector rotation angle effect when the second waveplate is removed, for a prototype configuration of the optical device (with quartz waveplates).

FIG. 41 shows the effect of rotating the PMT when the second waveplate is removed from the device, for the prototype device. In this configuration the polarisation bias of the detector contributes to the overall signal, leading to a substantial variation in CD magnitude with PMT angle. This configuration of the device is clearly not viable as a CD standard if used with polarisation sensitive detectors such as PMTs.

Figure 42A:
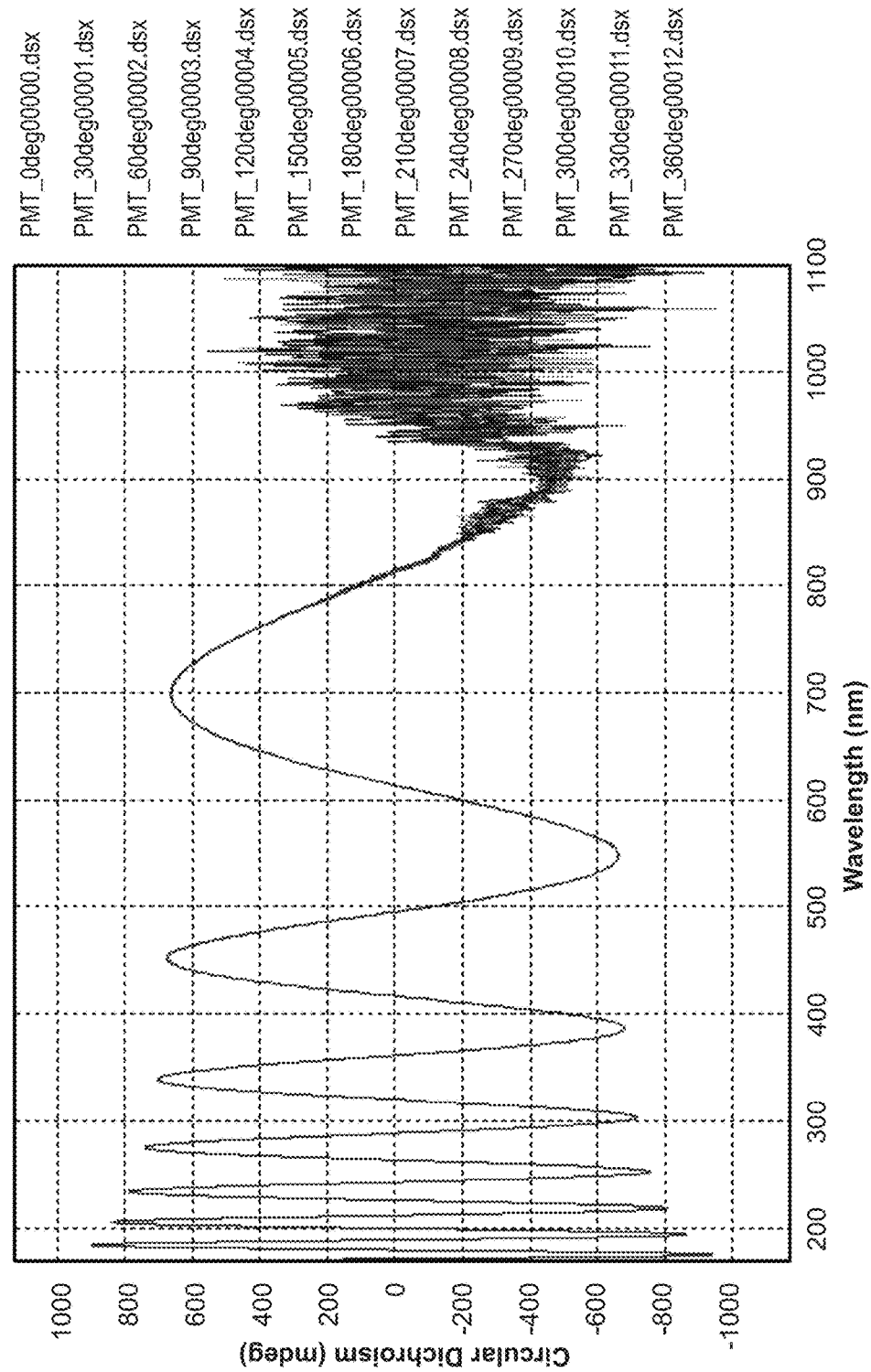
FIG. 42(a) is a graph that shows the PMT detector rotation angle effect when the second waveplate is in place, for one preferred configuration of the device (with $MgF_2$ waveplates) in a production model.
Figure 42B:
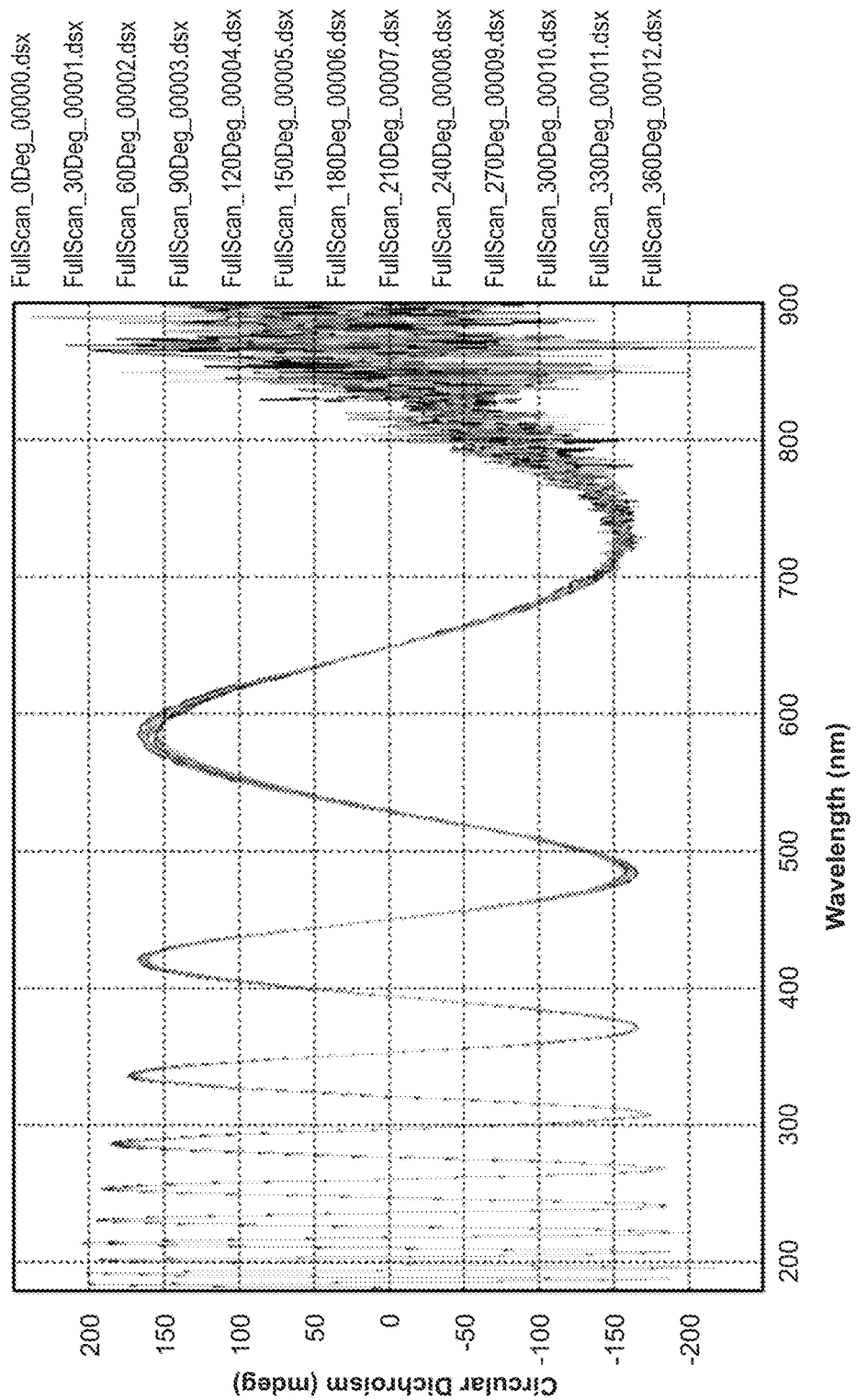
FIG. 42(b) is a graph that shows the PMT detector rotation angle effect when the second waveplate is in place, for a prototype configuration of the device (with quartz waveplates).

When the second waveplate was replaced, most of the CD variation was removed (see FIG. 42 (b)), but a small amount of variation (~±5%) remains. This is probably attributable to a non-perfect alignment of the second waveplate with respect to the first. In the production version (FIG. 42(a)) it is clear that the overlay of the spectra is substantially better, as is expected due to the more precise alignment of the waveplates in the production version of the device.

LAAPD Angle Dependence

Figure 43A:
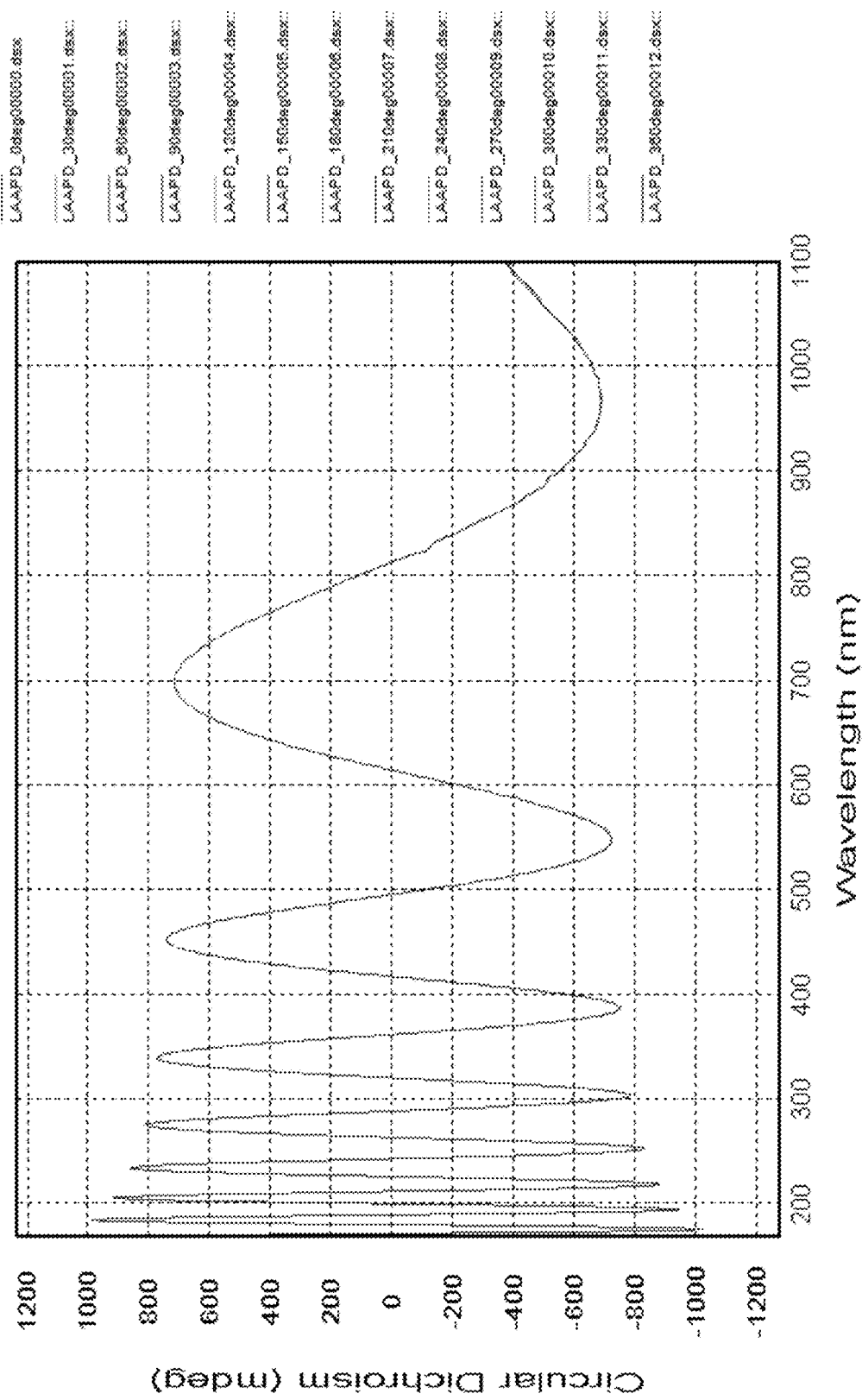
FIG. 43(a) is a graph that shows the LAAPD detector rotation angle effect when the second waveplate is in place for one preferred configuration of the optical device (with $MgF_2$ waveplates) in a production format.
Figure 43B:
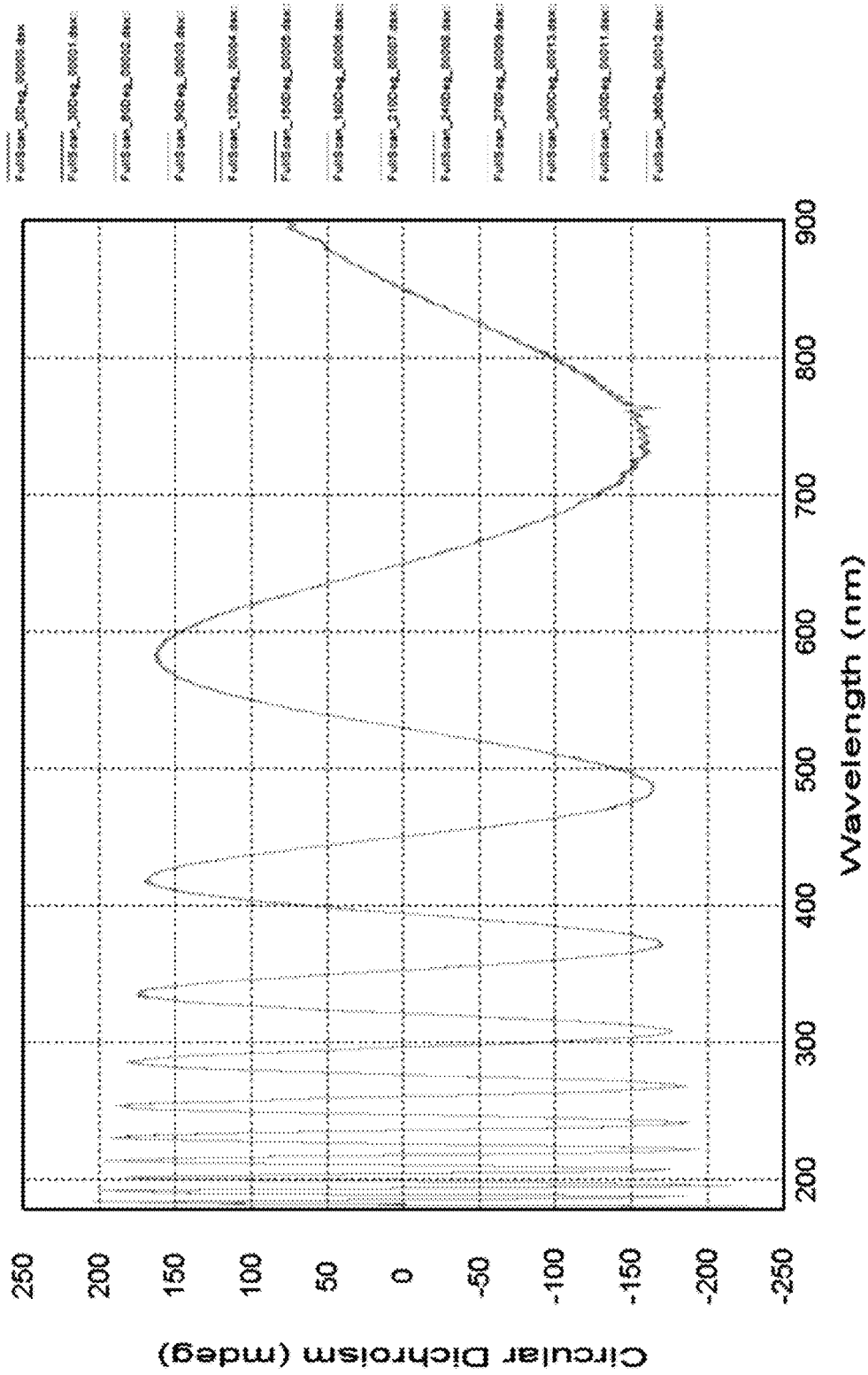
FIG. 43(b) is a graph that shows the LAAPD detector rotation angle effect when the second waveplate is in place for a prototype configuration of the optical device (with quartz waveplates).

The effect of detector angle on the measured spectrum is shown in FIG. 43(a) for the production device. There is very little variation in spectrum magnitude observable, highlighting the very low polarisation bias of the LAAPD detector. A similar result is seen for the prototype device (FIG. 43(b)).

Angular Sensitivity Measurements

In order to test the accuracy of the angular parameter sensitivities described supra, a number of sensitivity measurements were carried out on a few of the key parameters, using the prototype device. This was done by making a controlled deviation to the parameter in question and measuring the resulting change in spectrum magnitude. The results are presented in Table 8, along with the corresponding calculated values. The correspondence is good although measured values are slightly higher than the calculated values.

TABLE 8

| Parameter | Description | Angular Deviation | Measured CD Error | Calculated CD Error |
|---|---|---|---|---|
| $\theta_{IP}$ | Isoplates tilt angle | 3° | 39.95% | 34.37% |
| $\theta_{V\_Y}$ | V-plates group horizontal tilt | 2° | 5.82% | 4.24% |
| $\theta_{V\_Y}$ | V-plates group horizontal tilt | 4° | 21.3% | 17.0% |
| $\theta_{WP1\_Y}$ | Waveplate 1 Horizontal tilt | 3° | 0.94% | 0.7° |
| $\theta_{WP1\_Z}$ | Waveplate 1 Axial tilt | 4° | −1.19% | −0.97° |

As described herein, a mathematical investigation and series of experimental tests have been performed on a revised version of the optical CD calibration standard (DichOS-6). The results show that the defects of the original and simpler device (DichOS-3) have been either greatly reduced or eliminated completely. The results improved further on measuring the production device in which the waveplates and isoplates are more precisely aligned. The device described in the example herein shows excellent promise as a multi-wavelength wideband CD calibration device.

Further Adaptions, Design and Manufacturing Considerations

Aside from the configuration variants discussed above, there are other ways in which the device can be modified, some of which are described infra.

In certain exemplary embodiments, tilted plates may in be replaced with linearly dichroic samples or polarizers. However, this will in general produce signals which are too large and saturate the AC channel.

In other exemplary embodiments, tilted plates could be coated (either with dielectric or metal coatings) to change the magnitude characteristic of the CD spectrum. In the case of a metal coatings (e.g. Al), this could be used to provide attenuation (i.e. change in absorbance) in addition to changing the spectrum profile.

In still other exemplary embodiments, tilted isoplates may be replaced by pairs of opposing wedge prisms. The prisms have to be paired to avoid deflecting the beam. This idea was investigated earlier in the project and found to be less effective than plates. Its only advantage is that the tilt angle is effectively held on the prism apex angle and can thus be very stable and accurately manufactured.

In certain exemplary embodiments, the device could be augmented with neutral density filters, allowing the effective absorbance to be controlled independently. The present inventors have found that the best location for such filters is either at the front or rear of the device to reduce tilt sensitivity. There is a problem with finding absorptive type ND filters which cover the entire spectrum range. Reflective filters are available but earlier work suggest that the reflections can give rise to artifacts. An advantage of having the metal coating on a tilted surface, as mentioned above, is that the reflected beam is also deflected out of the light path.

In certain exemplary embodiments, the device could be augmented with a mechanical light attenuator (MLA) in the form of a grid, comb, aperture or similar device which causes one portion of the beam to be interrupted while another portion of the beam is allowed to propagate. A mechanical attenuator may be disposed at any position with respect to the other optical components comprising the device and has the advantage that it is effective over the entire wavelength range and is not sensitive to tilt angle.

In other exemplary embodiments, in those devices which have a central ½ waveplate, the crystal axis of this waveplate can be rotated 90°. This results in either a modified CD spectrum or modified error residual. The crystal axis orientations defined above are the preferred ones.

In still other exemplary embodiments, the broadband waveplates could be replaced with single wavelength zero order retarders (compound with VAR coatings) for accurate calibration at a single wavelength with minimal temperature related errors.

In certain exemplary embodiments, the broadband waveplates could be replaced with achromatic retarders, providing in effect a flat CD spectrum over a limited wavelength range. This might be useful for example if accurate calibration was required at a set of closely spaced wavelengths over a limited spectrum range.

In other exemplary embodiments, axial rotation of the device could be effected by means of a motor, enabling complete automation of the calibration procedure.

In still other exemplary embodiments, the device could be rotated continuously using a motor, in effect providing a way to mechanically average and allow the 'rotate & average' or '3-angle' corrected measurement to be obtained in a single pass rather than two.

Consideration should be given to sealing or purging the device to allow transmission of short wavelength (VUV) radiation. In the preferred embodiments, a manifold or bypass system would be employed to ensure that oxygen and other absorbing gases are purged from the spaces in between the plates. In preferred embodiments, some form of manifold or bypass system will be employed to ensure that nitrogen can flow through the device and clear air from the spaces in between the plates. Alternatively a means of sealing the optical housing of the device so as to enclose a nitrogen atmosphere may be employed, with a system to equalize internal and external pressure if required. In the absence of such features, the device will not function as well in the VUV region (i.e. below 200 nm).

Preferably, it must be ensured that deflected rays are trapped or absorbed within the device and cannot find a path to the detector, as this would lead to signal errors. Accordingly, in other exemplary embodiments, some form of baffle system and/or use of absorbing paint will be used.

In certain exemplary embodiments, beam angle errors could be corrected by angle tuning of the device while monitoring a live display of the CD signal. The error is minimized at the point where the CD signal is minimal. The angle tuning can be about a horizontal (X) axis, a vertical (Y) axis, or both.

In other exemplary embodiments, as an alternative to controlling accuracy by means of manufacturing tolerances, by axially rotating the tilted components with respect to the normal components the CD signal could be in effect 'dialed down' to a pre-determined value. The adjustment would then be locked once the desired signal magnitude had been achieved. This would require a specially designed jig to be used during manufacture.

The zero crossings of the CD spectrum can serve as wavelength markers, in principle allowing the device to provide a wavelength calibration in addition to CD calibration.

The device also functions as a linear dichroism (LD) standard, where the LD peaks correspond to the zero crossings of the CD spectrum (see FIG. 14).

Of the nine DichOS variants investigated, a preferred configuration is DichOS-6 with 'rotate & average' or '3-angle' correction to reduce the effect of beam errors. In the first instance, this involves making two measurements with the axial orientation of the device rotated 90° between the two. In the second instance, this involves making three measurements with the device rotated 45° between each measurement.

If measurements are restricted to peak wavelengths, then DichOS-9 allows a corrected measurement to be obtained in a single pass. The convenience of this comes at the cost of increased complexity (and expense) of the device. DichOS-9 has good correction at all wavelengths (similar to DichOS-6) if used with rotate & average correction, but the extra complexity for no apparent performance gain does not appear to be justified.

Having found solutions to correct beam error, and having performed extensive tolerance analyses, it is believed that the devices of the present invention can be configured so as to have <1% accuracy.

It has been discovered that when the DichOS device is used in an instrument having a reflective detector surface, that the reflection of the measuring beam from the detector can pass back into the DichOS device, whereupon an attenuated beam may subsequently be returned to the detector after reflection from any of the normally oriented optical surfaces (e.g. the waveplates) within the DichOS device. This process results in a signal artifact, causing the measured CD or LD signal to differ from that which is predicted from theory (as described supra). It is therefore preferable to eliminate or reduce this artifact as much as possible. Several methods have been tested and demonstrated to reduce this artifact, including moving the detector a further distance from the DichOS device, placing a diffusing optical element close to the detector surface to scatter the reflected light, placing a negative lens close to the detector surface to disperse the reflected light, tilting the detector or the DichOS device so that the reflected beam is deflected away from the normal light path, and placing a neutral density filter (in either a normal or tilted orientation to the beam) between the DichOS device and the detector so as to reduce the intensity of the reflected beam which returns to the detector. Other methods which are also expected to reduce or eliminate the artifact include placing a mechanical light attenuator between the DichOS device and the detector to attenuate the reflected light, and applying a calculated correction based on the known reflectance profile of the detector and DichOS optical elements and the known geometry of the instrument measuring beam. Any of the above methods are contemplated by the present invention.

In certain exemplary embodiments, further steps in the development of the device may be carried out, such as stray light analysis to confirm that, with a suitable blacking or trapping system, deflected rays do not reach the detector.

In other embodiments, the isoplates within the device have to be exceptionally clean in order to avoid generating signal artifacts, especially in the UV region of the spectrum. As such, isoplates are preferably subjected to a rigorous cleaning protocol prior to being installed in the device.

It has further been discovered that the presence of internal stress in the isoplates can introduce signal artifacts, especially in the UV part of the spectrum. As such, it is imperative to specify a high purity and low stress grade of fused silica for fabrication of the isoplates. Furthermore, the isoplates may be subjected to one or more annealing treatments in order to further reduce any residual stresses which may exist in the material.

In the UV region of the spectrum, the DichOS peaks become narrower and as such become more susceptible to broadening and flattening as a result of convolution with the instrument line function, which typically has a bandwidth (FWHM) of 1 nm. In order to maintain accuracy of the calibration, it has been discovered that the calculated DichOS spectrum must first be convolved with the known instrument line function at the defined measurement bandwidth (typically 1 nm). This results in slightly reduced heights of the calculated peaks in the UV region. A smaller correction is required for one preferred embodiment based on $MgF_2$ waveplates, since the peak density in the UV is lower for this design.

It has been discovered that, on measuring DichOS spectra at 0° and 90° rotation angles, a small wavelength shift is often observed which can be accurately measured by fitting straight lines at the zero crossing points of the spectrum. These wavelength shifts can subsequently be converted into a secondary calibration parameter (C2) which quantifies the imperfect polarization state of the beam prior to the photoelastic modulator (PEM). This second calibration parameter may be stored along with the primary calibration value (C1) and used in the calibration correction. The effect of C2 on CD spectra is generally extremely small, but it may be of more utility when measuring LD (linear dichroism) where signal magnitudes are often considerably larger.

All publications cited herein are incorporated by reference in their entirety. In case of conflict, the present specification, including definitions, will control. In addition, the materials, methods, and examples throughout the specification are illustrative only and not intended to be limiting in any way.

What is claimed is:

1. A device for calibrating circular dichroism or linear dichroism spectrometers or other photoelastic modulator based devices or instruments comprising: at least one waveplate (Q) providing (n±¼) waves of retardation at a defined set of wavelengths, wherein the waveplate (Q) has a thickness (t); comprising at least one waveplate (H) providing (N±½) waves of retardation at the same wavelengths where Q provides (n±¼) waves of retardation, wherein the waveplate (H) has a thickness (2+4m)t, where m is zero or a positive integer; and at least one isotropic plate (P).

2. The device of claim 1, wherein the waveplate (H) has a thickness (2t).

3. The device of claim 1, wherein the waveplate (Q) or the waveplate (H) is oriented with its surface normal to a direction of light propagation (Z axis).

4. The device of claim 1, wherein the waveplate (Q) or the waveplate (H) is oriented with its crystal axis at an angle about a Z axis, measured from the positive X axis direction.

5. The device of claim 4, wherein the angle is 45°.

6. The device of claim 3, wherein the waveplate (Q) or the waveplate (H) is subsequently rotated at an angle about a Y axis.

7. The device of claim 6, wherein the angle is between 1° and 90° about the Y axis.

8. The device of claim 3, wherein the waveplate (Q) or the waveplate (H) is subsequently rotated at an angle about an X axis.

9. The device of claim 8, wherein the angle is between 1° and 90° about the X axis.

10. The device of claim 1, wherein the isotropic plate (P) is oriented at an angle about a Y axis.

11. The device of claim 10, wherein the angle is between 1° and 90° about the Y axis.

12. The device of claim 1, wherein the isotropic plate (P) is oriented at an angle about an X axis.

13. The device of claim 12, wherein the angle is between 1° and 90° about the X axis.

14. The device of claim 1, wherein two isotropic plates (P) are oriented at equal and opposite angles about the X or Y axis.

15. The device of claim 1, wherein the isotropic plate (P) is oriented normal to a direction of light propagation (Z axis).

16. A method of calibrating circular dichroism spectrometers or linear dichroism spectrometers with the device of claim 1.

17. The device of claim 1, comprising two waveplates (Q) providing (n±¼) waves of retardation.

18. A device for calibrating circular dichroism or linear dichroism spectrometers or other photoelastic modulator based devices or instruments comprising:
- at least one waveplate (Q) providing (n±¼) waves of retardation at a defined set of wavelengths, wherein the waveplate (Q) has a thickness (t); and
- at least one isotropic plate (P), wherein a first isotropic plate (P) is oriented at a first angle about an axis;
- wherein a second isotropic plate (P) is oriented at a second angle about an axis;
- and wherein the first and second isotropic plates (P) are oriented at equal and opposite angles about the axis.

19. The device of claim 18, wherein the axis is an X axis.

20. The device of claim 18, wherein the axis is a Y axis.

21. The device of claim 19, wherein the angle is between 1° and 90° about the X axis.

22. The device of claim 20, wherein the angle is between 1° and 90° about the Y axis.

23. The device of claim 18, comprising two waveplates (Q) providing (n±¼) waves of retardation.

\* \* \* \* \*